(12) United States Patent
Vasdev et al.

(10) Patent No.: US 10,781,178 B2
(45) Date of Patent: Sep. 22, 2020

(54) 8-HYDROXYQUINOLINE DERIVATIVES AS DIAGNOSTIC AND THERAPEUTIC AGENTS

(71) Applicant: The General Hospital Corporation, Boston, MA (US)

(72) Inventors: Neil Vasdev, Cambridge, MA (US); Huan Steven Liang, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/751,778

(22) PCT Filed: Feb. 9, 2016

(86) PCT No.: PCT/US2016/017156
§ 371 (c)(1),
(2) Date: Feb. 9, 2018

(87) PCT Pub. No.: WO2017/027064
PCT Pub. Date: Feb. 16, 2017

(65) Prior Publication Data
US 2018/0327362 A1    Nov. 15, 2018

Related U.S. Application Data

(60) Provisional application No. 62/204,237, filed on Aug. 12, 2015.

(51) Int. Cl.
| | |
|---|---|
| *C07D 215/28* | (2006.01) |
| *C07D 401/12* | (2006.01) |
| *A61K 31/4709* | (2006.01) |
| *C07D 215/26* | (2006.01) |
| *A61K 45/06* | (2006.01) |
| *A61P 25/28* | (2006.01) |
| *A61P 35/00* | (2006.01) |
| *A61K 51/04* | (2006.01) |
| *C07B 59/00* | (2006.01) |

(52) U.S. Cl.
CPC ............ *C07D 215/28* (2013.01); *A61K 45/06* (2013.01); *A61K 51/0455* (2013.01); *A61P 25/28* (2018.01); *A61P 35/00* (2018.01); *C07B 59/002* (2013.01); *C07D 215/26* (2013.01); *C07D 401/12* (2013.01); *A61K 2123/00* (2013.01)

(58) Field of Classification Search
CPC .. C07D 215/26; C07D 215/28; C07D 401/12; A61K 31/4707; A61K 31/4709
See application file for complete search history.

(56) References Cited

U.S. PATENT DOCUMENTS

| | | | |
|---|---|---|---|
| 4,670,427 A | 6/1987 | Annen et al. | |
| 5,102,892 A | 4/1992 | Geiss et al. | |
| 7,692,011 B2 | 4/2010 | Barnham et al. | |
| 8,084,459 B2 | 12/2011 | Kok et al. | |
| 8,389,506 B2 | 3/2013 | Barnham et al. | |
| 8,889,695 B2 | 11/2014 | Huggins et al. | |
| 8,920,775 B2 | 12/2014 | Petersen et al. | |
| 8,975,278 B2 | 3/2015 | Barnham et al. | |
| 2006/0074104 A1 | 4/2006 | Bush et al. | |
| 2007/0038127 A1 | 2/2007 | Goldstein et al. | |
| 2008/0063599 A1 | 3/2008 | Quinquer et al. | |
| 2014/0088122 A1* | 3/2014 | Huggins ............ A61K 31/4375 514/264.1 |

FOREIGN PATENT DOCUMENTS

| | | |
|---|---|---|
| WO | WO 2001036395 | 5/2001 |
| WO | 2009/156737 | 12/2009 |

OTHER PUBLICATIONS

Steven H. Liang et al., Novel Fluorinated 8-Hydroxyquinoline Based Metal Ionophores for Exploring the Metal Hypothesis of Alzheimer's Disease, Med. Chem. Lett, 6, 1025-1029. (Year: 2015).*
'www.alzforum.org' [online]. "Therapeutics: Clioquinol," dated Mar. 9, 2014 [retrieved on Apr. 17, 2018]. Retrieved from the Internet: URL http://www.alzforum.org/therapeutics/clioquinol. 4 pages.
Abbott, "Dementia: A problem for our age," Nature, 2011, 475: S2-S4.
Agdeppa et al., "In Vitro Detection of (S)-Naproxen and Ibuprofen Binding to Plaques in the Alzheimer's Brain Using the Positron Emission Tomography Molecular Imaging Probe 2-(1-{6-[(2-[18f]Fluoroethyl)(Methyl)Amino]-2-Naphthyl}Ethylidene)Malononitrile," Neuroscience, 2003, 117: 723-730.
Bareggi and Cornelli, "Clioquinol: Review of its Mechanisms of Action and Clinical Uses in Neurodegenerative Disorders," CNS Neuroscience & Therapeutics, 2012, 18: 41-46.
Bush and Tanzi, "Therapeutics for Alzheimer's Disease Based on the Metal Hypothesis," Neurotherapeutics, 2008, 5: 421-432.
Bush, "Drug Development Based on the Metals Hypothesis of Alzheimer's Disease," J. Alzheimers Dis, 2008, 15: 223-240.
Carissimi et al, "IL Farmaco," Edizione Scientifica, 1969, 24(5): 478-99 (with English summary).
Cary et al., "Targeting Metal-Aβ Aggregates with Bifunctional Radioligand [11C]L2-b and a Fluorine-18 Analogue [18F]FL2-b," ACS Medicinal Chemistry Letters, 2015, 6: 112-116.

(Continued)

*Primary Examiner* — Michael G. Hartley
*Assistant Examiner* — Jagadishwar R Samala
(74) *Attorney, Agent, or Firm* — Fish & Richardson P.C.

(57) ABSTRACT

The present application provides compounds useful in methods of treating neurological disorders such as Alzheimer's disease, and cancer such as prostate cancer. Also provided herein are radiolabeled compounds useful for imaging techniques, and techniques for diagnosis and monitoring of treatment of neurological disorders and cancer. An exemplary radiolabeled compound provided herein is useful as a radiotracer for positron emission tomography or single-photon emission computed tomography. Methods for preparing radiolabeled compounds and methods for preparing unlabeled compounds are also provided.

13 Claims, 3 Drawing Sheets

(56) References Cited

OTHER PUBLICATIONS

CAS Registry No. 1244866-06-5, STN Entry Date Oct. 3, 2010, 1 page.
CAS Registry No. 1244880-39-4, STN Entry Date Oct. 3, 2010, 1 page.
CAS Registry No. 1244888-14-9, STN Entry Date Oct. 3, 2010, 1 page.
CAS Registry No. 1244938-32-6, STN Entry Date Oct. 3, 2010, 1 page.
CAS Registry No. 1309176-99-5, STN Entry Date Jun. 13, 2011, 1 page.
CAS Registry No. 1309227-70-0, STN Entry Date Jun. 13, 2011, 1 page.
CAS Registry No. 1309229-84-2, STN Entry Date Jun. 13, 2011, 1 page.
CAS Registry No. 1309246-98-7, STN Entry Date Jun. 13, 2011, 1 page.
CAS Registry No. 1309252-44-5, STN Entry Date Jun. 13, 2011, 1 page.
CAS Registry No. 1309255-92-2, STN Entry Date Jun. 13, 2011, 1 page.
CAS Registry No. 1309339-83-0, STN Entry Date Jun. 14, 2011, 1 page.
CAS Registry No. 1309346-24-4, STN Entry Date Jun. 14, 2011, 1 page.
CAS Registry No. 1347946-69-3, STN Entry Date Dec. 4, 2011, 1 page.
CAS Registry No. 1347946-70-6, STN Entry Date Dec. 4, 2011, 1 page.
Cherny et al., "Treatment with a Copper-Zinc Chelator Markedly and Rapidly Inhibits Aβ-Amyloid Accumulation in Alzheimer's Disease Transgenic Mice," Neuron, 2001, 30: 665-676.
Choi et al., "Design of small molecules that target metal-Aβ species and regulate metal-induced Aβ aggregation and neurotoxicity," PNAS, 2010, 107: 21990-21995.
Crouch and Barnham, "Therapeutic Redistribution of Metal Ions to Treat Alzheimer's Disease," Acc. Chem. Res, 2012, 45: 1604-1611.
Frederickson et al., "The neurobiology of zinc in health and disease," Nature Review Neuroscience, 2005, 6:, 449-462.
Hamley, "The Amyloid Beta Peptide: A Chemist's Perspective. Role in Alzheimer's and Fibrillization," Chem. Rev, 2012, 112: 5147-5192.
Hickey et al., "Diagnostic Imaging Agents for Alzheimer's Disease: Copper Radiopharmaceuticals that Target Aβ Plaques," J. Am. Chem. Soc, 2013, 135: 16120-16132.
Huntington Study Group Reach 2HD Investigators, "Safety, tolerability, and efficacy of PBT2 in Huntington's disease: a phase 2, randomised, double-blind, placebo-controlled trial," The Lancet Neurology, 2015, 14: 39-47.
International Preliminary Report on Patentability in International Application No. PCT/US2016/017156, dated Feb. 22, 2018, 22 pages.
Jakob-Roetne and Jacobsen, "Alzheimer's Disease: From Pathology to Therapeutic Approaches," Angew. Chem. Int. Ed, 2009, 48: 3030-3059.
Koehler et al., "Iodine-124: A Promising Positron Emitter for Organic PET Chemistry," Molecules, 2010, 15: 2686-2718.
Lannfelt,et al., "Safety, efficacy, and biomarker findings of PBT2 in targeting Aβ as a modifying therapy for Alzheimer's disease: a phase IIa, double-blind, randomised, placebo-controlled trial," The Lancet Neurology, Sep. 2008, 7: 779-786.
Lee et al., "Histochemically Reactive Zinc in Plaques of the Swedish Mutant β-Amyloid Precursor Protein Transgenic Mice," The Journal of Neuroscience, 1999, 19: RC10.
Liang et al., "Novel fluorinated 8-hydroxyquinoline based metal ionophores for exploring the metal hypothesis of Alzheimer's disease," ACS Med Chem Lett, Aug. 2015, 6 pages.
Liang et al., "PET Neuroimaging Studies of [18F]CABS13 in a Double Transgenic Mouse Model of Alzheimer's Disease and Nonhuman Primates," ACS Chemical Neuroscience, 2015, 6: 535-541.
Liang et al., "Rapid microfluidic flow hydrogenation for reduction or deprotection of 18F-labeled compounds," Chem. Commun, 2013, 49: 8755-8757.
Lovell et al., "Copper, iron and zinc in Alzheimer's disease senile plaques," J. Neurol. Sci, 2007. 158: 47-52.
Opazo et al., "Radioiodinated clioquinol as a biomarker for β-amyloid: Zn2+ complexes in Alzheimer's disease," Aging Cell, 2006, 5: 69-79.
Papazian et al., "The preparation of 123/125I-clioquinol for the study of Aβ protein in Alzheimer's disease," J. Labelled Compd. Radiopharm, 2005, 48: 473-484.
Rodríguez-Rodríguez et al., "The art of building multifunctional metal-binding agents from basic molecular scaffolds for the potential application in neurodegenerative diseases," Coord. Chem. Rev, 2012, 256: 2308-2332.
Suh et al., "Histochemically-reactive zinc in amyloid plaques, angiopathy, and degenerating neurons of Alzheimer's diseased brains," Brain Res, 2000, 852: 274-278.
Vasdev et al., "Synthesis and PET imaging studies of [18F]2-fluoroquinolin-8-ol ([18F]CABS13) in transgenic mouse models of Alzheimer's disease," MedChemComm, 2012, 3: 1228-1230.
Watt et al., "The Role of Zinc in Alzheimer's Disease," International Journal of Alzheimer's Disease, 2011, Article ID 971021.
International Search Report and Written Opinion dated Jun. 24, 2016 in international application No. PCT/US2016/017156, 26 pgs.
Sonino el al., "Quality of life of hirsute women," Postgraduate Medical Journal 69:186-189 (1993).
PUBCHEM. CID 13507847. Feb. 8, 2007, pp. 1-12; [online], [retrieved on Mar. 22, 2016]. Retrieved from the Internet <URL: https://pubchem.ncbi.nlm.nih.gov/compound/13507847#section=Top>.
PUBCHEM. CID 80694161. Oct. 20, 2014; [online], [retrieved on Mar. 22, 2016). Retrieved from the Internet <URL: https://pubchem.ncbi.nlm.nih.gov/compound/80694161#section=Top>.
PUBCHEM. AKOS012051146. Oct. 22, 2012, pp. 1-10; [online], [retrieved on Mar. 22, 2016]. Retrieved from the Internet <URL: https://pubchem.ncbi.nlm. nih.gov/compound/62757566>.
Hongmanee et al., "In Vitro Activities of Cloxyquin (5-Chloroquinolin-8-ol) against Mycobacterium tuberculosis," Antimicrobial Agents and Chemotherapy, pp. 1105-1106 (Mar. 2007).

\* cited by examiner

8-HYDROXYQUINOLINE DERIVATIVES AS DIAGNOSTIC AND THERAPEUTIC AGENTS

CLAIM OF PRIORITY

This application is a § 371 National Stage Application of PCT/US2016/017156, filed Feb. 9, 2016, which claims priority to U.S. Provisional Patent Application Ser. No. 62/204,237, filed on Aug. 12, 2015, the entire contents of which are hereby incorporated by reference.

TECHNICAL FIELD

The present application relates to metal-chelating heterocyclic compounds, and more particularly to 8-hydroxyquinoline derivatives which are useful for diagnosis and treatment of neurological disorders such as Alzheimer's disease, and cancers such as prostate cancer.

BACKGROUND

Alzheimer's disease (AD), a neurodegenerative disorder that affects approximately 44 million people world-wide, is the sixth leading cause of death with an estimated socio-economic burden of more than $200 billion. There is no cure for the debilitating disease with only few symptom-alleviating treatments. AD is characterized by extracellular amyloid plaques containing Cu and Zn, and which is accompanied by neuronal Cu deficiency and Zn dys-homeostasis. Zn and Cu ions are involved in the Aβ deposition and stabilization. Therefore, metal chelating agents may lead to the dissolution of Aβ deposits by preventing metal-Aβ interaction.

Accordingly, there is a need for compounds that can act as metal chelators for modulating metal-Aβ interaction, and can be used to treat and diagnose neurological disorders such as Alzheimer's disease. Accordingly, the present application provides compounds useful in the treatment of neurological disorders, in addition to methods of treatment of such disorders, and diagnostic methods.

SUMMARY

The present application provides, inter alia, a compound of Formula (I):

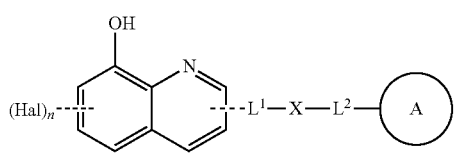

(I)

or a pharmaceutically acceptable salt thereof, wherein:

Hal is selected from the group consisting of Cl, F, Br, and I;

n is 1, 2, or 3;

X is selected from the group consisting of O, S, S(O), $S(O)_2$, C(O), and $NR^N$;

$L^1$ is selected from the group consisting of —$C_{1-6}$ alkylene-, —Y—$C_{1-6}$ alkylene-, —$C_{1-4}$ alkylene-Y—$C_{1-4}$ alkylene-, and —(O—$C_{1-4}$ alkylene)$_m$-, wherein m is an integer from 1 to 5, and wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

$L^2$ is selected from the group consisting of —$C_{1-6}$ alkylene-, —$C_{1-6}$ alkylene-Y—, —$C_{1-4}$ alkylene-Y—$C_{1-4}$ alkylene-, and —($C_{1-4}$ alkylene-O—)$_m$—, wherein m is an integer from 1 to 5, and wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

each Y is independently selected from the group consisting of O, S, S(O), $S(O)_2$, C(O), C(O)$NR^f$, $NR^fC(O)$, $S(O)_2NR^f$, $NR^fS(O)_2$, and $NR^f$;

each $R^f$ is independently selected from the group consisting of H and $C_{1-3}$ alkyl;

$R^N$ is selected from the group consisting of H, $C_{1-6}$ alkyl, $C_{2-6}$ alkenyl, $C_{2-6}$ alkynyl, $C_{1-4}$ haloalkyl, $C_{3-10}$ cycloalkyl, and 4-10 membered heterocycloalkyl, wherein said $C_{1-6}$ alkyl, $C_{2-6}$ alkenyl, $C_{2-6}$ alkynyl, $C_{1-4}$ haloalkyl, $C_{3-10}$ cycloalkyl, and 4-10 membered heterocycloalkyl are each optionally substituted by 1, 2, 3, or 4 independently selected $R^g$ groups;

group A is selected from the group consisting of a 5-10 membered heteroaryl and 4-10 membered heterocycloalkyl, each of which is optionally substituted by 1, 2, 3, or 4 independently selected $R^A$ groups;

alternatively, group A is H;

with the proviso that when X is $NR^N$, $L^1$ is —$C_{1-6}$ alkylene-, $L^2$ is —$C_{1-6}$ alkylene-, and $R^N$ is $C_{1-6}$ alkyl, group A is not H;

each $R^A$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^g$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula I is a compound of Formula Ia:

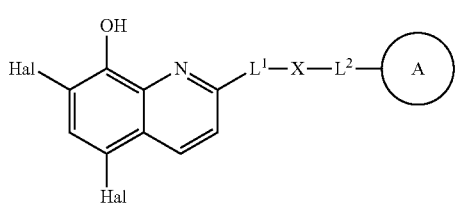

(Ia)

or a pharmaceutically acceptable salt thereof, wherein:

Hal is selected from the group consisting of Cl, F, Br, and I;

X is selected from the group consisting of O, S, S(O), S(O)$_2$, C(O), and NR$^N$;

L$^1$ is selected from the group consisting of —C$_{1-6}$ alkylene-, —Y—C$_{1-6}$ alkylene-, —C$_{1-4}$ alkylene-Y—C$_{1-4}$ alkylene-, or —(O—C$_{1-4}$ alkylene)$_m$-, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

L$^2$ is selected from the group consisting of —C$_{1-6}$ alkylene-, —C$_{1-6}$ alkylene-Y—, —C$_{1-4}$ alkylene-Y—C$_{1-4}$ alkylene-, and —(C$_{1-4}$ alkylene-O—)$_m$—, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

each Y is independently selected from the group consisting of O, S, S(O), S(O)$_2$, C(O), C(O)NR$^f$, NR$^f$C(O), S(O)$_2$NR$^f$, NR$^f$S(O)$_2$, and NR$^f$;

each R$^f$ is independently selected from the group consisting of H and C$_{1-3}$ alkyl;

R$^N$ is selected from the group consisting of H, C$_{1-6}$ alkyl, C$_{2-6}$ alkenyl, C$_{2-6}$ alkynyl, C$_{1-4}$ haloalkyl, C$_{3-10}$ cycloalkyl, 4-10 membered heterocycloalkyl, wherein said C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl are each optionally substituted by 1, 2, 3, or 4 independently selected R$^g$ groups;

group A is selected from the group consisting of a 5-10 membered heteroaryl and 4-10 membered heterocycloalkyl, each of which is optionally substituted by 1, 2, 3, or 4 independently selected R$^A$ groups;

alternatively, group A is H;

with the proviso that when X is NR$^N$, L$^1$ is —C$_{1-6}$ alkylene-, L$^2$ is —C$_{1-6}$ alkylene-, and R$^N$ is C$_{1-6}$ alkyl, group A is not H;

each R$^A$ is independently selected from the group consisting of OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl) carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and each R$^g$ is independently selected from the group consisting of OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl) carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, Hal is selected from the group consisting of Cl, F, and I. In some embodiments, Hal is Cl.

In some embodiments, X is selected from the group consisting of O, S, and NR$^N$.

In some embodiments, X is selected from the group consisting of O and NR$^N$.

In some embodiments, X is selected from the group consisting of O and —N(C$_{1-6}$ alkyl)-.

In some embodiments, X is selected from the group consisting of O and —N(CH$_3$)—.

In some embodiments, L$^1$ is selected from the group consisting of —C$_{1-6}$ alkylene-, —Y—C$_{1-6}$ alkylene-, and —C$_{1-4}$ alkylene-Y—C$_{1-4}$ alkylene-, wherein said alkylene groups are each optionally substituted with 1, 2, or 3 substituents independently selected from halo, CN, OH, C$_{1-3}$ alkoxy, amino, C$_{1-3}$ alkylamino, and di(C$_{1-3}$ alkyl)amino.

In some embodiments, L$^1$ is selected from the group consisting of —C$_{1-6}$ alkylene-, and —Y—C$_{1-6}$ alkylene-, wherein said alkylene groups are each optionally substituted with 1, 2, or 3 substituents independently selected from halo, CN, OH, C$_{1-3}$ alkoxy, and amino.

In some embodiments, L$^1$ is —C$_{1-6}$ alkylene-, wherein said alkylene group is optionally substituted with 1, 2, or 3 substituents independently selected from halo, CN, OH, C$_{1-3}$ alkoxy, and amino;

In some embodiments, L$^1$ is methylene.

In some embodiments, L$^2$ is selected from the group consisting of —C$_{1-6}$ alkylene-, —C$_{1-6}$ alkylene-Y—, and —C$_{1-4}$ alkylene-Y—C$_{1-4}$ alkylene-, wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino.

In some embodiments, L$^2$ is selected from the group consisting of —C$_{1-6}$ alkylene- and —C$_{1-6}$ alkylene-Y—, wherein said alkylene groups are each optionally substituted with 1, 2, or 3 substituents independently selected from halo, CN, OH, C$_{1-3}$ alkoxy, and amino.

In some embodiments, L$^2$ is —C$_{1-6}$ alkylene-, wherein said alkylene group is optionally substituted with 1, 2, or 3 substituents independently selected from halo, CN, OH, C$_{1-3}$ alkoxy, and amino.

In some embodiments, L$^2$ is selected from the group consisting of methylene, ethylene, and butylene.

In some embodiments, Y is selected from the group consisting of O, C(O), C(O)NR$^f$, NR$^f$C(O), and NR$^f$.

In some embodiments, Y is selected from the group consisting of O, C(O), —C(O)NH—, —NHC(O)—, NH, and —N(CH$_3$)—.

In some embodiments, R$^N$ is selected from the group consisting of H, C$_{1-6}$ alkyl, C$_{2-6}$ alkenyl, C$_{2-6}$ alkynyl, C$_{1-4}$ haloalkyl.

In some embodiments, R$^N$ is selected from the group consisting of H and C$_{1-6}$ alkyl.

In some embodiments, $R^N$ is —CH$_3$.

In some embodiments, X is selected from the group consisting of O, S, S(O), S(O)$_2$, and C(O); and group A is H.

In some embodiments, X is selected from the group consisting of O and S; and group A is H.

In some embodiments, X is O; and group A is H.

In some embodiments, $L^1$ is selected from the group consisting of —C$_{1-6}$ alkylene-, and —Y—C$_{1-6}$ alkylene-, wherein said alkylene groups are each optionally substituted with 1, 2, or 3 substituents independently selected from halo, CN, OH, C$_{1-3}$ alkoxy, and amino.

In some embodiments, $L^1$ is —C$_{1-6}$ alkylene-, wherein said alkylene group is optionally substituted with 1, 2, or 3 substituents independently selected from halo, CN, OH, C$_{1-3}$ alkoxy, and amino.

In some embodiments, $L^1$ is methylene.

In some embodiments, $L^2$ is —C$_{1-6}$ alkylene-, wherein said alkylene group is optionally substituted with 1, 2, or 3 substituents independently selected from halo, CN, OH, C$_{1-3}$ alkoxy, amino, C$_{1-3}$ alkylamino, and di(C$_{1-3}$ alkyl)amino.

In some embodiments, $L^2$ is selected from the group consisting of ethylene and butylene, each of which is optionally substituted with 1, 2, or 3 substituents independently selected from the group consisting of halo, CN, OH, C$_{1-3}$ alkoxy, amino, methylamino, and dimethylamino.

In some embodiments, $L^2$ is selected from the group consisting of ethylene and butylene, each of which is optionally substituted with 1, 2, or 3 halogen substituents independently selected from Cl, F, and I.

In some embodiments, $L^2$ is selected from the group consisting of ethylene and butylene, each of which is optionally substituted with one F.

In some embodiments, X is NR$^N$; and group A is selected from the group consisting of a 5 or 6 membered heteroaryl and 4-10 membered heterocycloalkyl, each of which is optionally substituted by 1, 2, 3, or 4 independently selected $R^4$ groups.

In some embodiments, X is NR$^N$; and group A is a 5 or 6 membered heteroaryl, which is optionally substituted by 1, 2, or 3 independently selected $R^4$ groups.

In some embodiments, X is —N(C$_{1-6}$ alkyl)-; and group A is a 5 or 6 membered heteroaryl, which is optionally substituted by 1, 2, or 3 independently selected $R^4$ groups.

In some embodiments, X is —N(C$_{1-6}$ alkyl)-; and group A is triazolyl, which is optionally substituted by 1, 2, or 3 independently selected $R^4$ groups.

In some embodiments, X is —N(CH$_3$)—; and group A is triazolyl, which is optionally substituted by 1, 2, or 3 independently selected $R^4$ groups.

In some embodiments, X is —N(CH$_3$)—; and group A is a triazolyl of Formula A-1:

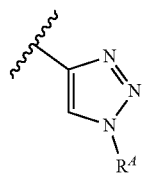

(A-1)

In some embodiments, $L^1$ is —C$_{1-6}$ alkylene-, wherein said alkylene group is optionally substituted with 1, 2, or 3 substituents independently selected from halo, CN, OH, C$_{1-3}$ alkoxy, and amino.

In some embodiments, $L^1$ is methylene.

In some embodiments, $L^2$ is —C$_{1-6}$ alkylene-, wherein said alkylene group is optionally substituted with 1, 2, or 3 substituents independently selected from halo, CN, OH, C$_{1-3}$ alkoxy, amino, C$_{1-3}$ alkylamino, and di(C$_{1-3}$ alkyl)amino.

In some embodiments, $L^2$ is methylene.

In some embodiments, $R^4$ is selected from the group consisting of OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments, $R^4$ is selected from the group consisting of halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments, $R^4$ is C$_{1-6}$ haloalkyl.

In some embodiments, $R^4$ is selected from the group consisting of 2-fluoroethyl, 3-fluoropropyl, and 4-fluorobutyl.

In some embodiments,

Hal is selected from the group consisting of Cl, F, and I;

X is selected from the group consisting of O, S, and NR$^N$;

$L^1$ is selected from the group consisting of —C$_{1-6}$ alkylene-, —Y—C$_{1-6}$ alkylene-, and —C$_{1-4}$ alkylene-Y—C$_{1-4}$ alkylene-, wherein said alkylene groups are each optionally substituted with 1, 2, or 3 substituents independently selected from halo, CN, OH, C$_{1-3}$ alkoxy, amino, C$_{1-3}$ alkylamino, and di(C$_{1-3}$ alkyl)amino;

$L^2$ is selected from the group consisting of —C$_{1-6}$ alkylene-, —C$_{1-6}$ alkylene-Y—, and —C$_{1-4}$ alkylene-Y—C$_{1-4}$ alkylene-, wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

Y is selected from the group consisting of O, C(O), C(O)NR$^f$, NR$^f$C(O), and NR$^f$;

each R$^f$ is independently selected from the group consisting of H and C$_{1-3}$ alkyl;

R$^N$ is selected from the group consisting of H, C$_{1-6}$ alkyl, C$_{2-6}$ alkenyl, C$_{2-6}$ alkynyl, and C$_{1-4}$ haloalkyl;

group A is selected from the group consisting of a 5-10 membered heteroaryl and 4-10 membered heterocycloalkyl, each of which is optionally substituted by 1, 2, 3, or 4 independently selected $R^4$ groups;

alternatively, group A is H;

with the proviso that when X is NR$^N$, $L^1$ is —C$_{1-6}$ alkylene-, $L^2$ is —C$_{1-6}$ alkylene-, and R$^N$ is C$_{1-6}$ alkyl, group A is not H; and each $R^4$ is independently selected from the group consisting of OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments,

Hal is Cl;

X is selected from the group consisting of O and NR$^N$;

$L^1$ is —C$_{1-6}$ alkylene-, wherein said alkylene group is optionally substituted with 1, 2, or 3 substituents independently selected from halo, CN, OH, C$_{1-3}$ alkoxy, and amino;

$L^2$ is —C$_{1-6}$ alkylene-, wherein said alkylene group is optionally substituted with 1, 2, or 3 substituents independently selected from halo, CN, OH, C$_{1-3}$ alkoxy, and amino;

R$^N$ is selected from the group consisting of H and C$_{1-6}$ alkyl;

group A is 5 or 6 membered heteroaryl, which is optionally substituted by 1, 2, or 3 independently selected $R^4$ groups;

alternatively, group A is H;

with the proviso that when X is $NR^N$, $L^1$ is $-C_{1-6}$ alkylene-, $L^2$ is $-C_{1-6}$ alkylene-, and $R^N$ is $C_{1-6}$ alkyl, group A is not H; and each $R^A$ is independently selected from the group consisting of OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino In some embodiments, Hal is selected from the group consisting of Cl, F, and I;

X is selected from the group consisting of O, S, S(O), $S(O)_2$, and C(O);

$L^1$ is selected from the group consisting of $-C_{1-6}$ alkylene- and $-Y-C_{1-6}$ alkylene-, wherein said alkylene groups are each optionally substituted with 1, 2, or 3 substituents independently selected from halo, CN, OH, $C_{1-3}$ alkoxy, and amino;

Y is selected from the group consisting of O, C(O), —C(O)NH—, —NHC(O)—, NH, and —N($CH_3$)—;

$L^2$ is $-C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

group A is selected from the group consisting of a 5-6 membered heteroaryl and 4-8 membered heterocycloalkyl, each of which is optionally substituted by 1, 2, 3, or 4 independently selected $R^A$ groups; and each $R^A$ is independently selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is selected from the group consisting of O and S;

$L^1$ is $-C_{1-6}$ alkylene-, wherein said alkylene group is optionally substituted with 1, 2, or 3 substituents independently selected from halo, CN, OH, $C_{1-3}$ alkoxy, and amino;

$L^2$ is $-C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

group A is 5-6 membered heteroaryl, which is optionally substituted by 1, 2, or 3 independently selected $R^A$ groups; and each $R^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, the compound of Formula Ia is a compound of Formula Ib:

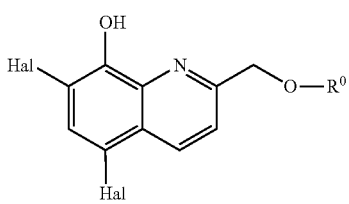

(Ib)

or a pharmaceutically acceptable salt thereof, wherein:

Hal is selected from the group consisting of Cl, F, and I; and $R^0$ is $-C_{1-6}$ alkyl, which is optionally substituted with 1, 2, or 3 substituents independently selected from halo, CN, OH, $C_{1-3}$ alkoxy, amino, $C_{1-3}$ alkylamino, and di($C_{1-3}$ alkyl)amino.

In some embodiments, $R^0$ is $C_{1-6}$ haloalkyl.

In some embodiments, $R^0$ is 2-fluoroethyl or 4-fluorobutyl.

In some embodiments,

Hal is selected from the group consisting of Cl, F, and I;

X is $NR^N$;

$L^1$ is $-C_{1-6}$ alkylene-, wherein said alkylene group is optionally substituted with 1, 2, or 3 substituents independently selected from halo, CN, OH, $C_{1-3}$ alkoxy, and amino;

$L^2$ is $-C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$R^N$ is selected from the group consisting of H and $C_{1-6}$ alkyl;

group A is selected from the group consisting of a 5 or 6 membered heteroaryl and 4-10 membered heterocycloalkyl, each of which is optionally substituted by 1, 2, 3, or 4 independently selected $R^A$ groups; and $R^A$ is selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is $NR^N$;

$L^1$ is $-C_{1-3}$ alkylene-, wherein said alkylene group is optionally substituted with 1, 2, or 3 substituents independently selected from halo, CN, OH, $C_{1-3}$ alkoxy, and amino;

$L^2$ is $-C_{1-3}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$R^N$ is selected from the group consisting of H and $C_{1-3}$ alkyl;

group A is 5 or 6 membered heteroaryl, which is optionally substituted by 1, 2, or 3 independently selected $R^A$ groups; and $R^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, the compound of Formula Ia is a compound of Formula Ic:

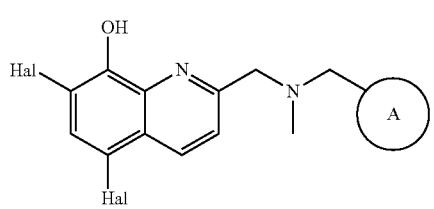

(Ic)

or a pharmaceutically acceptable salt thereof, wherein:

Hal is selected from the group consisting of Cl, F, and I; and group A is selected from the group consisting of a 5-6 membered heteroaryl and 4-10 membered heterocycloalkyl, each of which is optionally substituted by 1, 2, 3, or 4 independently selected $R^A$ groups.

In some embodiments, group A is a 5 membered heteroaryl, which is optionally substituted by 1, 2, or 3 independently selected $R^A$ groups.

In some embodiments, group A is triazolyl, which is optionally substituted by 1, 2, or 3 independently selected $R^A$ groups.

In some embodiments, group A is a triazolyl of Formula A-1c:

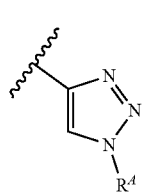

(A-1c)

In some embodiments, $R^A$ is selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, $R^A$ is selected from the group consisting of $C_{1-6}$ alkyl, $C_{1-6}$ haloalkyl, cyano-$C_{1-3}$ alkyl, and HO—$C_{1-3}$ alkyl.

In some embodiments, $R^A$ is $C_{1-6}$ haloalkyl.

In some embodiments, $R^A$ is 2-fluoroethyl, 3-fluoropropyl, or 4-fluorobutyl.

In some embodiments, the compound of Formula I is selected from the group consisting of:

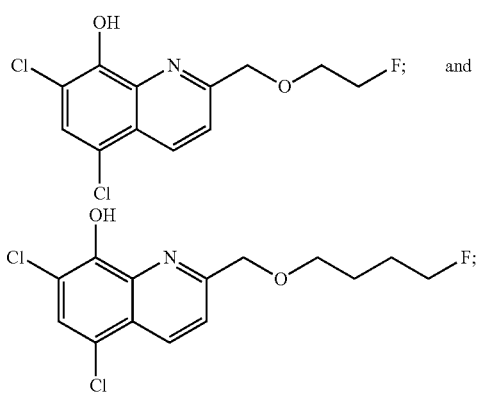

or a pharmaceutically acceptable salt of any of the aforementioned.

In some embodiments, compound of Formula I is selected from the group consisting of:

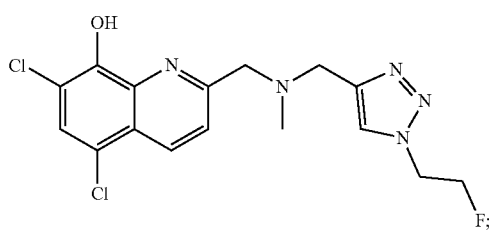

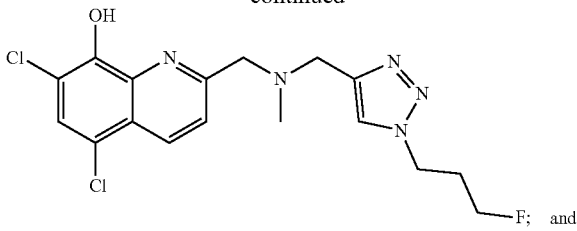

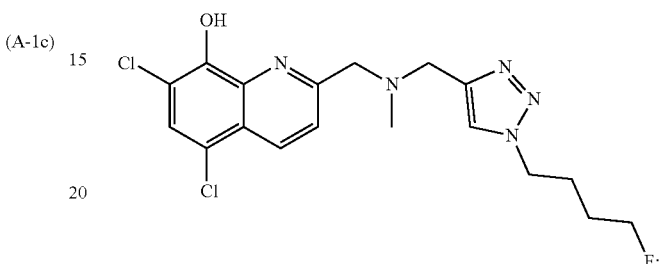

or a pharmaceutically acceptable salt thereof.

The present application further provides a pharmaceutical composition comprising a compound of any one of Formulae I, Ia, Ib and Ic, or a pharmaceutically acceptable salt thereof, and at least one pharmaceutically acceptable carrier.

The present application further provides a method of treating a neurological disorder in a subject in need thereof, the method comprising administering to the subject a therapeutically effective amount of a compound of any one of Formulae I, Ia, Ib and Ic, or a pharmaceutically acceptable salt thereof.

In some embodiments, the neurological disorder comprises a neurodegenerative disease.

In some embodiments, the neurological disorder is a neurodegenerative disease.

In some embodiments, neurodegenerative disease is selected from the group consisting of Alzheimer's disease (AD), Parkinson's disease (PD), Huntington's Disease (HD), motor neurone disease (MND), and Prion disease.

In some embodiments, neurodegenerative disease is Alzheimer's disease (AD).

In some embodiments, neurological disorder is selected from the group consisting of cerebral amyloid angiopathy, vascular cognitive impairment (VCI), dementia, dementia with Lewy bodies, frontotemporal dementia (FTD), amyotrophic lateral sclerosis (ALS), multiple sclerosis, hippocampal sclerosis, Binswanger's disease, and Creutzfeldt-Jakob disease.

The present application further provides a method of treating cancer in a subject in need thereof, the method comprising administering to the subject a therapeutically effective amount of a compound of Formulae I, Ia, Ib and Ic, or a pharmaceutically acceptable salt thereof.

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, the cancer is prostate cancer.

The present application further provides a compound of Formula II:

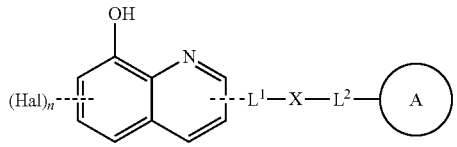
(II)

or a pharmaceutically acceptable salt thereof, wherein:

Hal is selected from the group consisting of Cl, F, Br, and I;

n is 1, 2, or 3;

X is selected from the group consisting of O, S, S(O), S(O)$_2$, C(O), and NR$^N$;

L$^1$ is selected from the group consisting of —C$_{1-6}$ alkylene-, —Y—C$_{1-6}$ alkylene-, —C$_{1-4}$ alkylene-Y—C$_{1-4}$ alkylene-, and —(O—C$_{1-4}$ alkylene)$_m$-, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

L$^2$ is selected from the group consisting of —C$_{1-6}$ alkylene-, —C$_{1-6}$ alkylene-Y—, —C$_{1-4}$ alkylene-Y—C$_{1-4}$ alkylene-, and —(C$_{1-4}$ alkylene-O—)$_m$—, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

each Y is independently selected from the group consisting of O, S, S(O), S(O)$_2$, C(O), C(O)NR$^f$, NR$^f$C(O), S(O)$_2$NR$^f$, NR$^f$S(O)$_2$, and NR$^f$;

each R$^f$ is independently selected from the group consisting of H and C$_{1-3}$ alkyl;

R$^N$ is selected from the group consisting of H, C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl, wherein said C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl are each optionally substituted by 1, 2, 3, or 4 independently selected R$^g$ groups;

group A is selected from the group consisting of a 5-10 membered heteroaryl and 4-10 membered heterocycloalkyl, each of which is optionally substituted by 1, 2, 3, or 4 independently selected R$^A$ groups;

alternatively, group A is H;

with the proviso that when X is NR$^N$, L$^1$ is —C$_{1-6}$ alkylene-, L$^2$ is —C$_{1-6}$ alkylene-, and R$^N$ is C$_{1-6}$ alkyl, group A is not H;

each R$^A$ is independently selected from the group consisting of OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^g$ is independently selected from the group consisting of OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and wherein the compound of Formula (II) comprises at least one radioisotope.

In some embodiments, the compound of Formula II is a compound of Formula IIa:

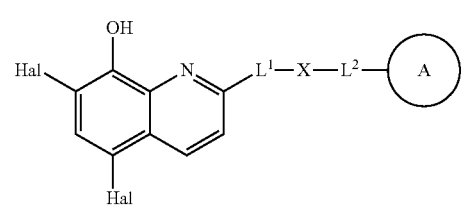
(IIa)

or a pharmaceutically acceptable salt thereof, wherein:

Hal is selected from the group consisting of Cl, F, Br, and I;

X is selected from the group consisting of O, S, S(O), S(O)$_2$, C(O), and NR$^N$;

L$^1$ is selected from the group consisting of —C$_{1-6}$ alkylene-, —Y—C$_{1-6}$ alkylene-, —C$_{1-4}$ alkylene-Y—C$_{1-4}$ alkylene-, and —(O—C$_{1-4}$ alkylene)$_m$-, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

L$^2$ is selected from the group consisting of —C$_{1-6}$ alkylene-, —C$_{1-6}$ alkylene-Y—, —C$_{1-4}$ alkylene-Y—C$_{1-4}$ alkylene-, or —(C$_{1-4}$ alkylene-O—)$_m$—, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

each Y is independently selected from the group consisting of O, S, S(O), S(O)$_2$, C(O), C(O)NR$^f$, NR$^f$C(O), S(O)$_2$NR$^f$, NR$^f$S(O)$_2$, and NR$^f$;

each R$^f$ is independently selected from the group consisting of H and C$_{1-3}$ alkyl;

R$^N$ is selected from the group consisting of H, C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl, wherein said C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl are each optionally substituted by 1, 2, 3, or 4 independently selected R$^g$ groups;

group A is selected from the group consisting of a 5-10 membered heteroaryl and 4-10 membered heterocycloalkyl, each of which is optionally substituted by 1, 2, 3, or 4 independently selected $R^A$ groups;

alternatively, group A is H;

with the proviso that when X is $NR^N$, $L^1$ is —$C_{1-6}$ alkylene-, $L^2$ is —$C_{1-6}$ alkylene-, and $R^N$ is $C_{1-6}$ alkyl, group A is not H;

each $R^A$ is independently selected from the group consisting of OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^g$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and wherein the compound of Formula (IIa) comprises at least one radioisotope.

In some embodiments, Hal is selected from the group consisting of Cl, F, and I. In some embodiments, Hal is Cl.

In some embodiments, X is selected from the group consisting of O, S, and $NR^N$.

In some embodiments, X is selected from the group consisting of O and $NR^N$.

In some embodiments, X is selected from the group consisting of O and —N($C_{1-6}$ alkyl)-.

In some embodiments, X is selected from the group consisting of O and —N($CH_3$)—.

In some embodiments, $L^1$ is selected from the group consisting of —$C_{1-6}$ alkylene-, —Y—$C_{1-6}$ alkylene-, and —$C_{1-4}$ alkylene-Y—$C_{1-4}$ alkylene-, wherein said alkylene groups are each optionally substituted with 1, 2, or 3 substituents independently selected from halo, CN, OH, $C_{1-3}$ alkoxy, amino, $C_{1-3}$ alkylamino, and di($C_{1-3}$ alkyl)amino.

In some embodiments, $L^1$ is selected from the group consisting of —$C_{1-6}$ alkylene-, and —Y—$C_{1-6}$ alkylene-, wherein said alkylene groups are each optionally substituted with 1, 2, or 3 substituents independently selected from halo, CN, OH, $C_{1-3}$ alkoxy, and amino.

In some embodiments, $L^1$ is —$C_{1-6}$ alkylene-, wherein said alkylene group is optionally substituted with 1, 2, or 3 substituents independently selected from halo, CN, OH, $C_{1-3}$ alkoxy, and amino;

In some embodiments, $L^1$ is methylene.

In some embodiments, $L^2$ is selected from the group consisting of —$C_{1-6}$ alkylene-, —$C_{1-6}$ alkylene-Y—, and —$C_{1-4}$ alkylene-Y—$C_{1-4}$ alkylene-, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments, $L^2$ is selected from the group consisting of —$C_{1-6}$ alkylene- and —$C_{1-6}$ alkylene-Y—, wherein said alkylene groups are each optionally substituted with 1, 2, or 3 substituents independently selected from halo, CN, OH, $C_{1-3}$ alkoxy, and amino.

In some embodiments, $L^2$ is —$C_{1-6}$ alkylene-, wherein said alkylene group is optionally substituted with 1, 2, or 3 substituents independently selected from halo, CN, OH, $C_{1-3}$ alkoxy, and amino.

In some embodiments, $L^2$ is selected from the group consisting of methylene, ethylene, and butylene.

In some embodiments, Y is selected from the group consisting of O, C(O), C(O)$NR^f$, $NR^f$C(O), and $NR^f$.

In some embodiments, Y is selected from the group consisting of O, C(O), —C(O)NH—, —NHC(O)—, NH, and —N($CH_3$)—.

In some embodiments, $R^N$ is selected from the group consisting of H, $C_{1-6}$ alkyl, $C_{2-6}$ alkenyl, $C_{2-6}$ alkynyl, and $C_{1-4}$ haloalkyl.

In some embodiments, $R^N$ is selected from the group consisting of H and $C_{1-6}$ alkyl.

In some embodiments, $R^N$ is —$CH_3$.

In some embodiments, X is selected from the group consisting of O, S, S(O), S(O)$_2$, and C(O); and group A is H.

In some embodiments, X is selected from the group consisting of O and S; and group A is H.

In some embodiments, X is O; and group A is H.

In some embodiments, $L^1$ is selected from the group consisting of —$C_{1-6}$ alkylene-, and —Y—$C_{1-6}$ alkylene-, wherein said alkylene groups are each optionally substituted with 1, 2, or 3 substituents independently selected from halo, CN, OH, $C_{1-3}$ alkoxy, and amino.

In some embodiments, $L^1$ is —$C_{1-6}$ alkylene-, wherein said alkylene group is optionally substituted with 1, 2, or 3 substituents independently selected from halo, CN, OH, $C_{1-3}$ alkoxy, and amino.

In some embodiments, $L^1$ is methylene.

In some embodiments, $L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino.

In some embodiments, $L^2$ is selected from the group consisting of ethylene and butylene, each of which is optionally substituted with 1, 2, or 3 substituents independently selected from the group consisting of halo, CN, OH, $C_{1-3}$ alkoxy, amino, methylamino, and dimethylamino.

In some embodiments, $L^2$ is selected from the group consisting of ethylene and butylene, each of which is optionally substituted with 1, 2, or 3 halogen substituents independently selected from Cl, F, and I.

In some embodiments, $L^2$ is selected from the group consisting of ethylene and butylene, each of which is optionally substituted with one F.

In some embodiments, X is $NR^N$; and group A is selected from the group consisting of a 5 or 6 membered heteroaryl and 4-10 membered heterocycloalkyl, each of which is optionally substituted by 1, 2, 3, or 4 independently selected $R^A$ groups.

In some embodiments, X is $NR^N$; and group A is a 5 or 6 membered heteroaryl, which is optionally substituted by 1, 2, or 3 independently selected $R^A$ groups.

In some embodiments, X is —N($C_{1-6}$ alkyl)-; and group A is triazolyl, which is optionally substituted by 1, 2, or 3 independently selected $R^A$ groups.

In some embodiments, X is —N($CH_3$)—; and group A is triazolyl, which is optionally substituted by 1, 2, or 3 independently selected $R^A$ groups.

In some embodiments, X is —N(CH₃)—; and group A is a triazolyl of Formula A-1:

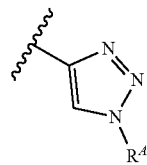

(A-1)

In some embodiments, L¹ is —C$_{1-6}$ alkylene-, wherein said alkylene group is optionally substituted with 1, 2, or 3 substituents independently selected from halo, CN, OH, C$_{1-3}$ alkoxy, and amino.

In some embodiments, L¹ is methylene.

In some embodiments, L² is —C$_{1-6}$ alkylene-, wherein said alkylene group is optionally substituted with 1, 2, or 3 substituents independently selected from halo, CN, OH, C$_{1-3}$ alkoxy, amino, C$_{1-3}$ alkylamino, and di(C$_{1-3}$ alkyl)amino.

In some embodiments, L² is methylene.

In some embodiments, R$^A$ is selected from the group consisting of OH, NO₂, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments, R$^A$ is selected from the group consisting of halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments, R$^A$ is C$_{1-6}$ haloalkyl.

In some embodiments, R$^A$ is 2-fluoroethyl, 3-fluoropropyl, or 4-fluorobutyl.

In some embodiments,

Hal is selected from the group consisting of Cl, F, and I;

X is selected from the group consisting of O, S, and NR$^N$;

L¹ is selected from the group consisting of —C$_{1-6}$ alkylene-, —Y—C$_{1-6}$ alkylene-, and —C$_{1-4}$ alkylene-Y—C$_{1-4}$ alkylene-, wherein said alkylene groups are each optionally substituted with 1, 2, or 3 substituents independently selected from halo, CN, OH, C$_{1-3}$ alkoxy, amino, C$_{1-3}$ alkylamino, and di(C$_{1-3}$ alkyl)amino;

L² is selected from the group consisting of —C$_{1-6}$ alkylene-, —C$_{1-6}$ alkylene-Y—, and —C$_{1-4}$ alkylene-Y—C$_{1-4}$ alkylene-, wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

Y is selected from the group consisting of O, C(O), C(O)NR$^f$, NR$^f$C(O), and NR$^f$;

each R$^f$ is independently selected from the group consisting of H and C$_{1-3}$ alkyl;

R$^N$ is selected from the group consisting of H, C$_{1-6}$ alkyl, C$_{2-6}$ alkenyl, C$_{2-6}$ alkynyl, C$_{1-4}$ haloalkyl;

group A is selected from the group consisting of a 5-10 membered heteroaryl and 4-10 membered heterocycloalkyl, each of which is optionally substituted by 1, 2, 3, or 4 independently selected R$^A$ groups;

alternatively, group A is H;

with the proviso that when X is NR$^N$, L¹ is —C$_{1-6}$ alkylene-, L² is —C$_{1-6}$ alkylene-, and R$^N$ is C$_{1-6}$ alkyl, group A is not H; and each R$^A$ is independently selected from the group consisting of OH, NO₂, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments,

Hal is Cl;

X is selected from the group consisting of O and NR$^N$;

L¹ is —C$_{1-6}$ alkylene-, wherein said alkylene group is optionally substituted with 1, 2, or 3 substituents independently selected from halo, CN, OH, C$_{1-3}$ alkoxy, and amino;

L² is —C$_{1-6}$ alkylene-, wherein said alkylene group is optionally substituted with 1, 2, or 3 substituents independently selected from halo, CN, OH, C$_{1-3}$ alkoxy, and amino;

R$^N$ is selected from the group consisting of H and C$_{1-6}$ alkyl;

group A is 5 or 6 membered heteroaryl, which is optionally substituted by 1, 2, or 3 independently selected R$^A$ groups;

alternatively, group A is H;

with the proviso that when X is NR$^N$, L¹ is —C$_{1-6}$ alkylene-, L² is —C$_{1-6}$ alkylene-, and R$^N$ is C$_{1-6}$ alkyl, group A is not H; and each R$^A$ is independently selected from the group consisting of OH, NO₂, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments,

Hal is selected from the group consisting of Cl, F, and I;

X is selected from the group consisting of O, S, S(O), S(O)₂, and C(O);

L¹ is selected from the group consisting of —C$_{1-6}$ alkylene-, and —Y—C$_{1-6}$ alkylene-, wherein said alkylene groups are each optionally substituted with 1, 2, or 3 substituents independently selected from halo, CN, OH, C$_{1-3}$ alkoxy, and amino;

Y is selected from the group consisting of O, C(O), —C(O)NH—, —NHC(O)—, NH, and —N(CH₃)—;

L² is —C$_{1-6}$ alkylene-, wherein said alkylene group is optionally substituted with 1, 2, or 3 substituents independently selected from halo, CN, OH, C$_{1-3}$ alkoxy, amino, C$_{1-3}$ alkylamino, and di(C$_{1-3}$ alkyl)amino;

group A is selected from the group consisting of a 5-6 membered heteroaryl and 4-8 membered heterocycloalkyl, each of which is optionally substituted by 1, 2, 3, or 4 independently selected R$^A$ groups; and each R$^A$ is independently selected from the group consisting of OH, NO₂, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments,

Hal is selected from the group consisting of Cl, F, and I;

X is selected from the group consisting of O and S;

L¹ is —C$_{1-6}$ alkylene-, wherein said alkylene group is optionally substituted with 1, 2, or 3 substituents independently selected from halo, CN, OH, C$_{1-3}$ alkoxy, and amino;

L² is —C$_{1-6}$ alkylene-, wherein said alkylene group is optionally substituted with 1, 2, or 3 substituents independently selected from halo, CN, OH, C$_{1-3}$ alkoxy, amino, C$_{1-3}$ alkylamino, and di(C$_{1-3}$ alkyl)amino;

group A is 5-6 membered heteroaryl, which is optionally substituted by 1, 2, or 3 independently selected R$^A$ groups; and each R$^A$ is selected from the group consisting of halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino.

In some embodiments, the compound of Formula IIa is a compound of Formula IIb:

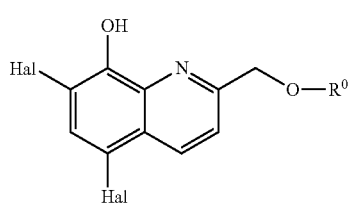

(IIb)

or a pharmaceutically acceptable salt thereof, wherein:

Hal is selected from the group consisting of Cl, F, and I; and $R^0$ is —$C_{1-6}$ alkyl, which is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

wherein the compound of Formula (IIb) comprises at least one radioisotope.

In some embodiments, $R^0$ is $C_{1-6}$ haloalkyl.

In some embodiments, $R^0$ is 2-fluoroethyl or 4-fluorobutyl.

In some embodiments, $R^0$ comprises at least one radioisotope.

In some embodiments, $R^0$ comprises one radioisotope.

In some embodiments,

Hal is selected from the group consisting of Cl, F, and I;

X is $NR^N$;

$L^1$ is —$C_{1-6}$ alkylene-, wherein said alkylene group is optionally substituted with 1, 2, or 3 substituents independently selected from halo, CN, OH, $C_{1-3}$ alkoxy, and amino;

$L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$R^N$ is selected from the group consisting of H and $C_{1-6}$ alkyl;

group A is selected from the group consisting of a 5 or 6 membered heteroaryl and 4-10 membered heterocycloalkyl, each of which is optionally substituted by 1, 2, 3, or 4 independently selected $R^A$ groups; and $R^A$ is selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is $NR^N$;

$L^1$ is —$C_{1-3}$ alkylene-, wherein said alkylene group is optionally substituted with 1, 2, or 3 substituents independently selected from halo, CN, OH, $C_{1-3}$ alkoxy, and amino;

$L^2$ is —$C_{1-3}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$R^N$ is selected from the group consisting of H and $C_{1-3}$ alkyl;

group A is 5 or 6 membered heteroaryl, which is optionally substituted by 1, 2, or 3 independently selected $R^A$ groups; and $R^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, the compound of Formula IIa is a compound of Formula IIc:

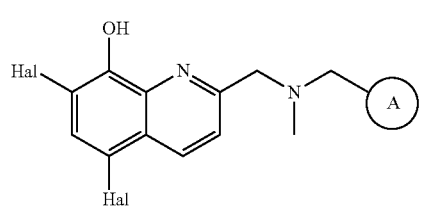

(IIc)

or a pharmaceutically acceptable salt thereof, wherein:

Hal is selected from the group consisting of Cl, F, and I;

group A is selected from the group consisting of a 5-6 membered heteroaryl and 4-10 membered heterocycloalkyl, each of which is optionally substituted by 1, 2, 3, or 4 independently selected $R^A$ groups; and wherein the compound of Formula (IIc) comprises at least one radioisotope.

In some embodiments, group A is a 5 membered heteroaryl, which is optionally substituted by 1, 2, or 3 independently selected $R^A$ groups.

In some embodiments, group A is triazolyl, which is optionally substituted by 1, 2, or 3 independently selected $R^A$ groups.

In some embodiments, group A is a triazolyl of Formula A-1c:

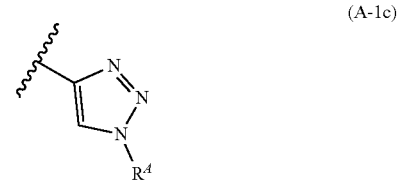

(A-1c)

In some embodiments, $R^A$ is selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, $R^A$ is selected from the group consisting of $C_{1-6}$ alkyl, $C_{1-6}$ haloalkyl, cyano-$C_{1-3}$ alkyl, and HO—$C_{1-3}$ alkyl.

In some embodiments, $R^A$ is $C_{1-6}$ haloalkyl.

In some embodiments, $R^A$ is 2-fluoroethyl, 3-fluoropropyl, or 4-fluorobutyl.

In some embodiments, $R^A$ comprises at least one radioisotope.

In some embodiments, $R^A$ comprises one radioisotope.

In some embodiments, $R^N$ comprises at least one radioisotope.

In some embodiments, $R^N$ comprises one radioisotope.

In some embodiments, $L^2$ comprises at least one radioisotope.

In some embodiments, $L^2$ comprises one radioisotope.

In some embodiments, at least one Hal is a radioisotope.

In some embodiments, one Hal is a radioisotope.

In some embodiments, the at least one radioisotope is a positron emitter.

In some embodiments, the positron emitter is selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$T, $^{110m}$In, $^{118}$Sb, $^{120}$I, $^{121}$I, $^{122}$I, and $^{124}$I.

In some embodiments, the positron emitter is $^{11}$C or $^{18}$F.

In some embodiments, the at least one radioisotope is a gamma emitter.

In some embodiments, the gamma emitter is selected from the group consisting of $^{99m}$Tc, $^{123}$I, $^{125}$I, $^{131}$I, and $^{123}$I.

In some embodiments, the compound comprises one radioisotope.

In some embodiments, the compound of Formula II is selected from the group consisting of:

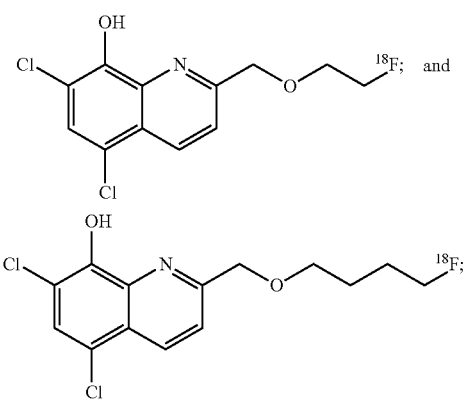

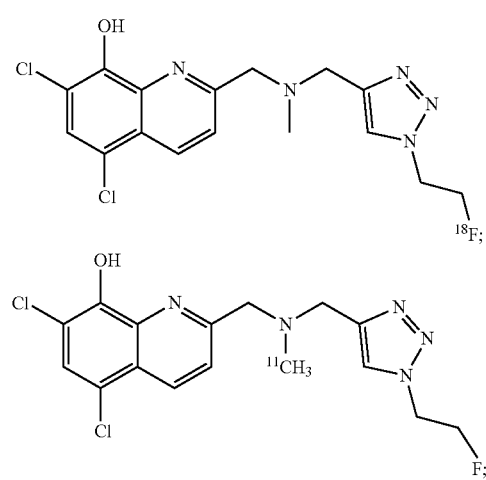

or a pharmaceutically acceptable salt thereof.

In some embodiments, the compound of Formula II is selected from the group consisting of:

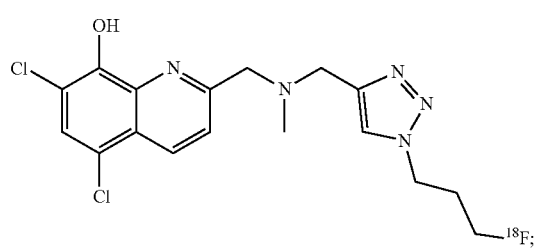

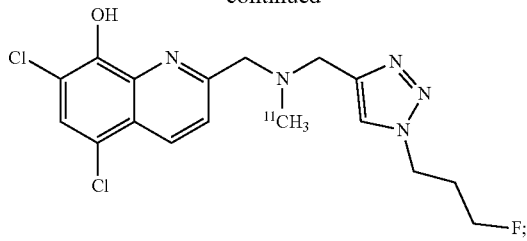

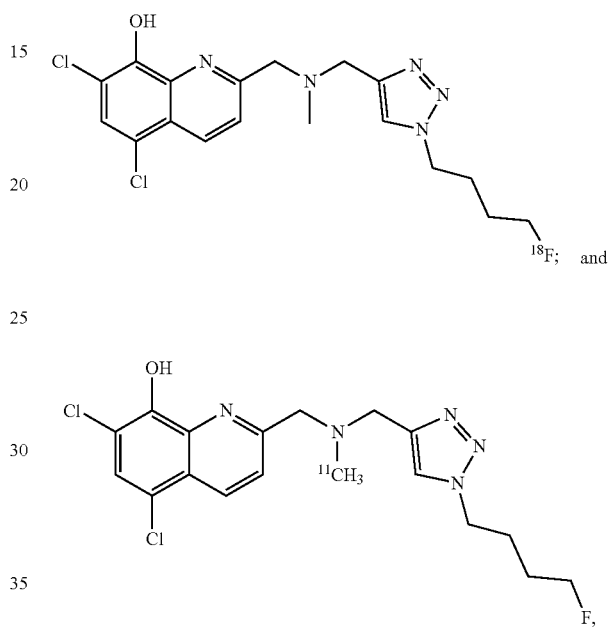

or a pharmaceutically acceptable salt thereof.

The present application further provides a pharmaceutical composition comprising a compound of any one of Formulae II, IIa, IIb, and IIc, or a pharmaceutically acceptable salt thereof, and at least one pharmaceutically acceptable carrier.

The present application further provides a method of imaging the brain of a subject, the method comprising:
i. administering to the subject an effective amount of a compound of any one of Formulae II, IIa, IIb, and IIc, or a pharmaceutically acceptable salt thereof;
ii. waiting a time sufficient to allow the compound to accumulate in the brain to be imaged; and
iii. imaging the brain with an imaging technique.

The present application further provides a method of diagnosing a neurological disorder in a subject, the method comprising:
i. administering to the subject a compound of any one of Formulae II, IIa, IIb, and IIc;
ii. waiting a time sufficient to allow the compound to accumulate at a tissue or cell site associated with the neurological disorder; and
iii. imaging the cell or tissue with an imaging technique.

The present application further provides a method of monitoring treatment of a neurological disorder in a subject, the method comprising:
i. imaging a cell or tissue with an imaging technique;
ii. administering to the subject a compound of any one of Formulae II, IIa, IIb, and IIc in an effective amount of to treat the neurological disorder;

iii. waiting a time sufficient to allow the compound to accumulate at a tissue or cell site associated with the neurological disorder;
iv. imaging the cell or tissue with an imaging technique; and
v. comparing the image of step i) and the image of step iv).

In some embodiments, the imaging technique is selected from the group consisting of magnetic resonance imaging, optical imaging, single-photon emission computer tomography, positron emission tomography imaging, positron emission tomography with computer tomography imaging, and positron emission tomography with magnetic resonance imaging.

In some embodiments, the imaging technique is selected from the group consisting of positron emission tomography (PET) and single-photon emission computer tomography (SPECT).

In some embodiments, the neurological disorder comprises a neurodegenerative disease.

In some embodiments, the neurological disorder is a neurodegenerative disease.

In some embodiments, neurodegenerative disease is selected from the group consisting of Alzheimer's disease (AD), Parkinson's disease (PD), Huntington's Disease (HD), motor neurone disease (MND), and Prion disease.

In some embodiments, neurodegenerative disease is Alzheimer's disease (AD).

In some embodiments, neurological disorder is selected from the group consisting of cerebral amyloid angiopathy, vascular cognitive impairment (VCI), dementia, dementia with Lewy bodies, frontotemporal dementia (FTD), amyotrophic lateral sclerosis (ALS), multiple sclerosis, hippocampal sclerosis, Binswanger's disease, and Creutzfeldt-Jakob disease.

The present application further provides a method of diagnosing a cancer in a subject, the method comprising:
 i. administering to the subject a compound of any one of Formulae II, IIa, IIb;
 ii. waiting a time sufficient to allow the compound to accumulate at a tissue or cell site associated with the cancer; and
 iii. imaging the cell or tissue with an imaging technique.

The present application further provides a method of monitoring treatment of a cancer in a subject, the method comprising:
 i. imaging a cell or tissue with an imaging technique;
 ii. administering to the subject a compound of any one of Formulae II, IIa, IIb in an effective amount of to treat the cancer;
 iii. waiting a time sufficient to allow the compound to accumulate at a tissue or cell site associated with the cancer;
 iv. imaging the cell or tissue with an imaging technique; and
 v. comparing the image of step i) and the image of step iv).

In some embodiments, the imaging technique is selected from the group consisting of magnetic resonance imaging, optical imaging, single-photon emission computer tomography, positron emission tomography imaging, positron emission tomography with computer tomography imaging, and positron emission tomography with magnetic resonance imaging.

In some embodiments, the imaging technique is selected from the group consisting of positron emission tomography (PET) and single-photon emission computer tomography (SPECT).

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, the cancer is prostate cancer.

The present application further provides a compound of Formula III:

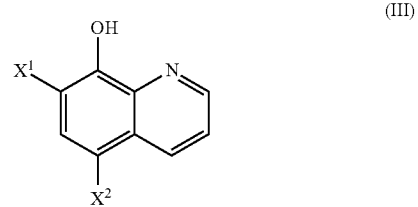

or a pharmaceutically acceptable salt thereof, wherein:
each $X^1$ and $X^2$ is independently selected from the group consisting of F, Cl, Br, and I;
wherein at least one of $X^1$ and $X^2$ comprises a radioisotope; and
wherein:
when $X^1$ is I or F, then $X^2$ is not Cl; and
when $X^1$ is I, then $X^2$ is not F.

In some embodiments, $X^1$ is F and $X^2$ is Br.
In some embodiments, $X^1$ is F and $X^2$ is I.
In some embodiments, $X^1$ is Cl and $X^2$ is F.
In some embodiments, $X^1$ is Br and $X^2$ is F.
In some embodiments, $X^1$ is F and $X^2$ is F.
In some embodiments, $X^1$ is I and $X^2$ is Br.

In some embodiments, the compound of Formula III is selected from the group consisting of:

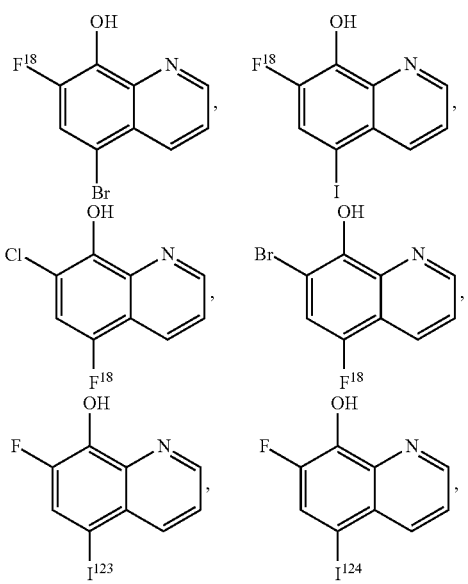

-continued

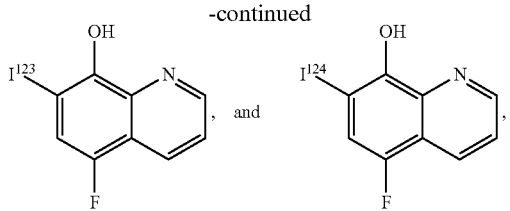

or a pharmaceutically acceptable salt thereof.

The present application further provides a pharmaceutical composition comprising a compound of any one of Formula III, or a pharmaceutically acceptable salt thereof, and at least one pharmaceutically acceptable carrier.

The present application further provides a method of imaging the brain of a subject, the method comprising:
 i. administering to the subject an effective amount of a compound of any one of Formula III, or a pharmaceutically acceptable salt thereof;
 ii. waiting a time sufficient to allow the compound to accumulate the brain to be imaged; and
 iii. imaging the brain with an imaging technique.

The present application further provides a method of diagnosing a neurological disorder in a subject, the method comprising:
 i. administering to the subject a compound of any one of Formula III;
 ii. waiting a time sufficient to allow the compound to accumulate at a tissue or cell site associated with the neurological disorder; and
 iii. imaging the cell or tissue with an imaging technique.

The present application further provides a method of monitoring treatment of a neurological disorder in a subject, the method comprising:
 i. imaging a cell or tissue with an imaging technique;
 ii. administering to the subject a compound of any one of Formula III in an effective amount of to treat the neurological disorder;
 iii. waiting a time sufficient to allow the compound to accumulate at a tissue or cell site associated with the neurological disorder;
 iv. imaging the cell or tissue with an imaging technique; and
 v. comparing the image of step i) and the image of step iv).

In some embodiments, the imaging technique is selected from the group consisting of magnetic resonance imaging, optical imaging, single-photon emission computer tomography, positron emission tomography imaging, positron emission tomography with computer tomography imaging, and positron emission tomography with magnetic resonance imaging.

In some embodiments, the imaging technique is selected from the group consisting of positron emission tomography (PET) and single-photon emission computer tomography (SPECT).

In some embodiments, the neurological disorder comprises a neurodegenerative disease.

In some embodiments, the neurological disorder is a neurodegenerative disease.

In some embodiments, neurodegenerative disease is selected from the group consisting of Alzheimer's disease (AD), Parkinson's disease (PD), Huntington's Disease (HD), motor neurone disease (MND), and Prion disease.

In some embodiments, neurodegenerative disease is Alzheimer's disease (AD).

In some embodiments, neurological disorder is selected from the group consisting of cerebral amyloid angiopathy, vascular cognitive impairment (VCI), dementia, dementia with Lewy bodies, frontotemporal dementia (FTD), amyotrophic lateral sclerosis (ALS), multiple sclerosis, hippocampal sclerosis, Binswanger's disease, and Creutzfeldt-Jakob disease.

The present application further provides a method of diagnosing a cancer in a subject, the method comprising:
 i. administering to the subject a compound of any one of Formula III;
 ii. waiting a time sufficient to allow the compound to accumulate at a tissue or cell site associated with the cancer; and
 iii. imaging the cell or tissue with an imaging technique.

The present application further provides a method of monitoring treatment of a cancer in a subject, the method comprising:
 i. imaging a cell or tissue with an imaging technique;
 ii. administering to the subject a compound of any one of Formula III in an effective amount of to treat the cancer;
 iii. waiting a time sufficient to allow the compound to accumulate at a tissue or cell site associated with the cancer;
 iv. imaging the cell or tissue with an imaging technique; and
 v. comparing the image of step i) and the image of step iv).

In some embodiments, the imaging technique is selected from the group consisting of magnetic resonance imaging, optical imaging, single-photon emission computer tomography, positron emission tomography imaging, positron emission tomography with computer tomography imaging, and positron emission tomography with magnetic resonance imaging.

In some embodiments, the imaging technique is selected from the group consisting of positron emission tomography (PET) and single-photon emission computer tomography (SPECT).

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, the cancer is prostate cancer.

DETAILED DESCRIPTION

Figure 1:
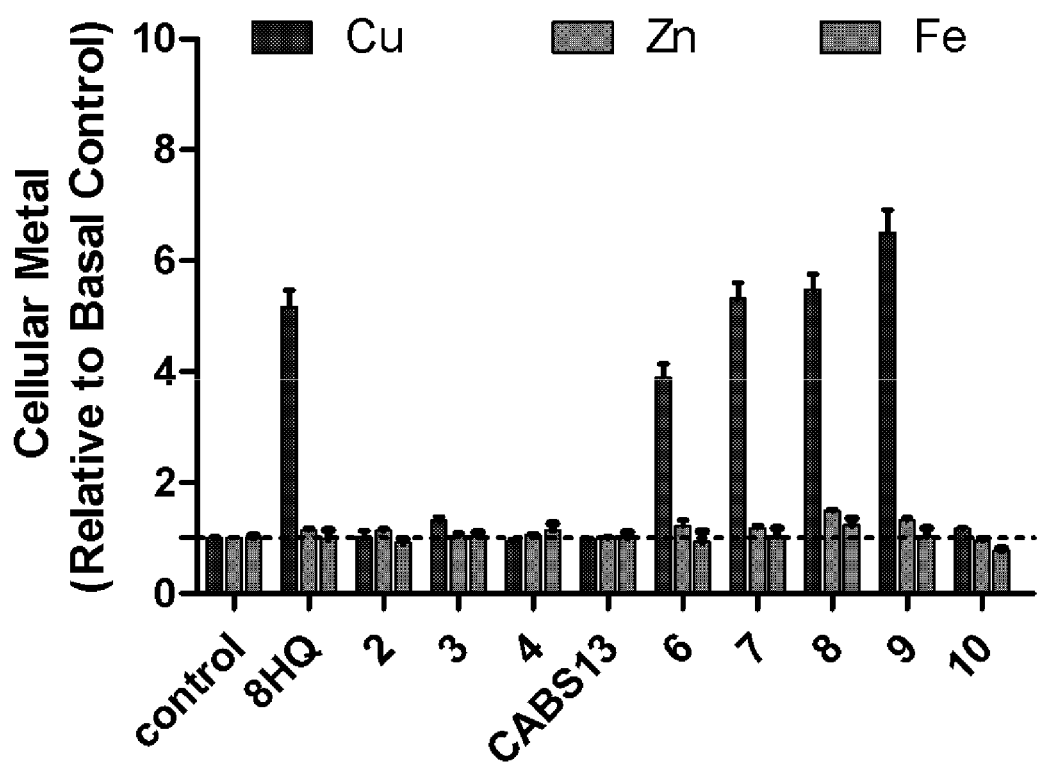
FIG. 1 shows an ionophore assay of 8HQ and 8HQ derivatives: Compounds 2-10.

A metal-chelating agent, 5-chloro-7-iodo-quinolin-8-ol (clioquinol; CQ), has been shown to prevent Aβ toxicity. CQ not only prevents or reverses extracellular Aβ aggregation, but also transports metal ions as membrane penetrating metal complexes to increase intracellular metal concentration, thereby initiating protective cell signaling events to degrade Aβ and prevent toxicity. In a pilot phase II clinical trial, CQ was well tolerated and attenuated the rate of cognitive decline in AD patients, however further development was halted due to a contaminant during the manufacturing process. Another metal chelator, PBT2 (5,7-Dichloro-2-((dimethylamino)methyl) 8-quinolinol) has shown benefits in patients with Huntington's disease and patients with AD in phase II clinical trials.

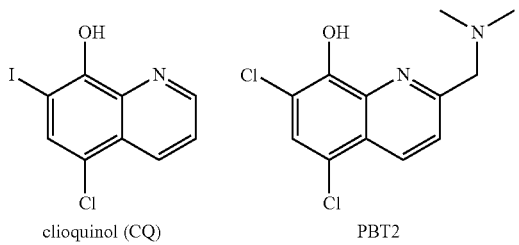

clioquinol (CQ)     PBT2

To identify a suitable metal chelator for AD drug development, a radiopharmaceutical based on a metal chelator would be useful to determine metal concentration and distribution in the living brain by positron emission tomography (PET) or single-photon emission computed tomography (SPECT). Development of such agents could advance the understanding of AD etiology that is affected by dysregulation of metal functions, and could prove useful in monitoring therapeutic response and disease progression for patients with AD.

Accordingly, the present application provides a series of 8-hydroxyquinoline derivatives and identifies several potent and metal selective chelators for therapeutic applications that are also amenable for labeling with radionuclides such as $^{18}F$ and/or $^{11}C$ as potential PET ligands or with $^{123}I$ as potential SPECT ligands. The present application describes compounds that showed superior binding affinity, metal selectivity, and Cu and Zn ionophore activity over the agents CQ and PBT2. The compounds of the present application are useful as drug candidates and/or as PET or SPECT ligands to diagnose and/or treat neurological disorders such as Alzheimer's disease.

Compounds

The present application provides, inter alia, a compound of Formula (I):

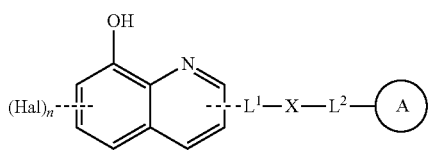

or a pharmaceutically acceptable salt thereof, wherein:

Hal is selected from the group consisting of Cl, F, Br, and I;

n is 1, 2, or 3;

X is selected from the group consisting of O, S, S(O), $S(O)_2$, C(O), and $NR^N$;

$L^1$ is selected from the group consisting of —$C_{1-6}$ alkylene-, —Y—$C_{1-6}$ alkylene-, —$C_{1-4}$ alkylene-Y—$C_{1-4}$ alkylene-, and —(O—$C_{1-4}$ alkylene)$_m$-, wherein m is an integer from 1 to 5, and wherein the alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

$L^2$ is selected from the group consisting of —$C_{1-6}$ alkylene-, —$C_{1-6}$ alkylene-Y—, —$C_{1-4}$ alkylene-Y—$C_{1-4}$ alkylene-, and —($C_{1-4}$ alkylene-O—)$_m$—, wherein m is an integer from 1 to 5, and wherein the alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

each Y is independently selected from the group consisting of O, S, S(O), $S(O)_2$, C(O), C(O)$NR^f$, $NR^f$C(O), $S(O)_2NR^f$, $NR^fS(O)_2$, and $NR^f$;

each $R^f$ is independently selected from the group consisting of H and $C_{1-3}$ alkyl;

$R^N$ is selected from the group consisting of H, $C_{1-6}$ alkyl, $C_{2-6}$ alkenyl, $C_{2-6}$ alkynyl, $C_{1-4}$ haloalkyl, $C_{3-10}$ cycloalkyl, and 4-10 membered heterocycloalkyl, wherein the $C_{1-6}$ alkyl, $C_{2-6}$ alkenyl, $C_{2-6}$ alkynyl, $C_{1-4}$ haloalkyl, $C_{3-10}$ cycloalkyl, and 4-10 membered heterocycloalkyl are each optionally substituted by 1, 2, 3, or 4 independently selected $R^g$ groups;

group A is selected from the group consisting of a 5-10 membered heteroaryl and 4-10 membered heterocycloalkyl, each of which is optionally substituted by 1, 2, 3, or 4 independently selected $R^A$ groups;

alternatively, group A is H;

with the proviso that when X is $NR^N$, $L^1$ is —$C_{1-6}$ alkylene-, $L^2$ is —$C_{1-6}$ alkylene-, and $R^N$ is $C_{1-6}$ alkyl, group A is not H;

each $R^A$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^g$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, Hal is selected from the group consisting of Cl, F, and I. In some embodiments, Hal is Cl. In some embodiments, Hal is F. In some embodiments, Hal is I. In some embodiments, both Hal groups are Cl. In some embodiments, both Hal groups are F. In some embodiments, both Hal groups are I. In some embodiments, one of the Hal groups is Cl and another Hal group is F. In some embodiments, one of the Hal groups is Cl and another Hal group is I. In some embodiments, one of the Hal groups is F and another Hal group is I.

In some embodiments, X is selected from the group consisting of O, S, and $NR^N$. In some embodiments, X is selected from the group consisting of O and $NR^N$. In some embodiments, X is selected from the group consisting of O and $—N(C_{1-6}$ alkyl)-. In some embodiments, X is selected from the group consisting of O and $—N(CH_3)—$. In some embodiments, X is O. In some embodiments, X is $NR^N$. In some embodiments, $—N(C_{1-6}$ alkyl)-. In some embodiments, $—N(CH_3)—$.

In some embodiments, $L^1$ is selected from the group consisting of $—C_{1-6}$ alkylene-, $—Y—C_{1-6}$ alkylene-, and $—C_{1-4}$ alkylene-Y—$C_{1-4}$ alkylene-, wherein the alkylene groups are each optionally substituted with 1, 2, or 3 substituents independently selected from halo, CN, OH, $C_{1-3}$ alkoxy, amino, $C_{1-3}$ alkylamino, and di($C_{1-3}$ alkyl)amino.

In some embodiments, $L^1$ is selected from the group consisting of $—C_{1-6}$ alkylene-, and $—Y—C_{1-6}$ alkylene-, wherein the alkylene groups are each optionally substituted with 1, 2, or 3 substituents independently selected from halo, CN, OH, $C_{1-3}$ alkoxy, and amino.

In some embodiments, $L^1$ is $—C_{1-6}$ alkylene-, wherein the alkylene group is optionally substituted with 1, 2, or 3 substituents independently selected from halo, CN, OH, $C_{1-3}$ alkoxy, and amino. In some embodiments, $L^1$ is methylene.

In some embodiments, $L^2$ is selected from the group consisting of $—C_{1-6}$ alkylene-, $—C_{1-6}$ alkylene-Y—, and $—C_{1-4}$ alkylene-Y—$C_{1-4}$ alkylene-, wherein the alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments, $L^2$ is selected from the group consisting of $—C_{1-6}$ alkylene- and $—C_{1-6}$ alkylene-Y—, wherein the alkylene groups are each optionally substituted with 1, 2, or 3 substituents independently selected from halo, CN, OH, $C_{1-3}$ alkoxy, and amino.

In some embodiments, $L^2$ is $—C_{1-6}$ alkylene-, wherein the alkylene group is optionally substituted with 1, 2, or 3 substituents independently selected from halo, CN, OH, $C_{1-3}$ alkoxy, and amino. In some embodiments, $L^2$ is selected from the group consisting of methylene, ethylene, and butylene.

In some embodiments, Y is selected from the group consisting of O, C(O), C(O)$NR^f$, $NR^f$C(O), and $NR^f$. In some embodiments, Y is selected from the group consisting of O, C(O), —C(O)NH—, —NHC(O)—, NH, and —N(CH$_3$)—.

In some embodiments, $R^N$ is selected from the group consisting of H, $C_{1-6}$ alkyl, $C_{2-6}$ alkenyl, $C_{2-6}$ alkynyl, $C_{1-4}$ haloalkyl. In some embodiments, $R^N$ is selected from the group consisting of H and $C_{1-6}$ alkyl. In some embodiments, $R^N$ is H. In some embodiments, $R^N$ is $C_{1-6}$ alkyl. In some embodiments, $R^N$ is $C_{1-4}$ haloalkyl. In some embodiments, $R^N$ is —CH$_3$.

In some embodiments, X is selected from the group consisting of O, S, S(O), S(O)$_2$, and C(O); and group A is H. In some embodiments, X is selected from the group consisting of O and S; and group A is H. In some embodiments, X is O; and group A is H. In some aspects of these embodiments, $L^1$ is selected from the group consisting of $—C_{1-6}$ alkylene-, and $—Y—C_{1-6}$ alkylene-, wherein the alkylene groups are each optionally substituted with 1, 2, or 3 substituents independently selected from halo, CN, OH, $C_{1-3}$ alkoxy, and amino. In some aspects of these embodiments, $L^1$ is $—C_{1-6}$ alkylene-, wherein the alkylene group is optionally substituted with 1, 2, or 3 substituents independently selected from halo, CN, OH, $C_{1-3}$ alkoxy, and amino.

In some aspects of these embodiments, $L^1$ is methylene. In some aspects of these embodiments, $L^2$ is $—C_{1-6}$ alkylene-, wherein the alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino. In some aspects of these embodiments, $L^2$ is selected from the group consisting of ethylene and butylene, each of which is optionally substituted with 1, 2, or 3 substituents independently selected from the group consisting of halo, CN, OH, $C_{1-3}$ alkoxy, amino, methylamino, and dimethylamino. In some aspects of these embodiments, $L^2$ is selected from the group consisting of ethylene and butylene, each of which is optionally substituted with 1, 2, or 3 halogen substituents independently selected from Cl, F, and I. In some aspects of these embodiments, $L^2$ is selected from the group consisting of ethylene and butylene, each of which is optionally substituted with one F. In some aspects of these embodiments, $L^2$ is fluoroethylene. In some aspects of these embodiments, $L^2$ is fluorobutylene.

In some embodiments, X is $NR^N$; and group A is selected from the group consisting of a 5 or 6 membered heteroaryl and 4-10 membered heterocycloalkyl, each of which is optionally substituted by 1, 2, 3, or 4 independently selected $R^A$ groups. In some embodiments, X is $NR^N$; and group A is a 5 or 6 membered heteroaryl, which is optionally substituted by 1, 2, or 3 independently selected $R^A$ groups. In some embodiments, X is $—N(C_{1-6}$ alkyl)-; and group A is a 5 or 6 membered heteroaryl, which is optionally substituted by 1, 2, or 3 independently selected $R^A$ groups. In some embodiments, X is $—N(C_{1-6}$ alkyl)-; and group A is triazolyl, which is optionally substituted by 1, 2, or 3 independently selected $R^A$ groups. In some embodiments, X is $—N(CH_3)—$; and group A is triazolyl, which is optionally substituted by 1, 2, or 3 independently selected $R^A$ groups. In some embodiments, X is $—N(CH_3)—$; and group A is a triazolyl of Formula A-1:

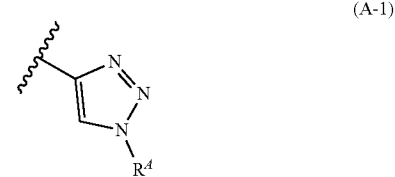

(A-1)

In some aspects of these embodiments, $L^1$ is $—C_{1-6}$ alkylene-, wherein the alkylene group is optionally substituted with 1, 2, or 3 substituents independently selected from halo, CN, OH, $C_{1-3}$ alkoxy, and amino. In some aspects of these embodiments, $L^1$ is methylene. In some aspects of these embodiments, $L^2$ is $—C_{1-6}$ alkylene-, wherein the alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino. In some aspects of these embodiments, $L^2$ is methylene. In some aspects of these embodiments, $R^A$ is selected from the group consisting of OH, NO$_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino. In some aspects of these embodiments, $R^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino. In some aspects of these embodiments, $R^A$ is $C_{1-6}$ haloalkyl. In some aspects of these embodiments, $R^A$ is selected from the group consisting of 2-fluoroethyl, 3-fluoropropyl, and 4-fluorobutyl. In some aspects of these embodiments, $R^A$ is 2-fluoroethyl. In some aspects of these embodiments, $R^A$ is 3-fluoropropyl. In some aspects of these embodiments, $R^A$ is 4-fluorobutyl.

In some embodiments, group A is H.

In some embodiments, group A is selected from the group consisting of a 5 or 6 membered heteroaryl and 4-10 membered heterocycloalkyl, each of which is optionally substituted by 1, 2, 3, or 4 independently selected $R^A$ groups.

In some embodiments, group A is 5 or 6 membered heteroaryl which is optionally substituted by 1, 2, 3, or 4 independently selected $R^A$ groups. In some embodiments, group A is 5 membered heteroaryl which is optionally substituted by 1, 2, or 3 independently selected $R^A$ groups. In some embodiments, group A is 6 membered heteroaryl which is optionally substituted by 1, 2, or 3 independently selected $R^A$ groups.

In some embodiments, group A is selected from the group consisting of pyridinyl, triazinyl, pyridazinyl, pyrimidinyl, and pyrazinyl, each of which is optionally substituted by 1, 2, 3, or 4 independently selected $R^A$ groups. In some embodiments, group A is selected from the group consisting of triazolyl, pyrazolyl, imidazolyl, isoxazolyl, oxazolyl, isothiazolyl, thiazolyl, furanyl, and thiophenyl, each of which is optionally substituted by 1, 2, 3, or 4 independently selected $R^A$ groups.

In some embodiments, group A is triazolyl, which is optionally substituted by 1, 2, 3, or 4 independently selected $R^A$ groups. In some embodiments, group A is triazolyl, which is optionally substituted by 1 $R^A$ group.

In some embodiments, group A is a triazolyl of Formula A-1:

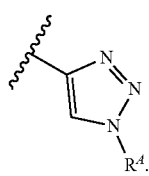

(A-1)

In some embodiments, group A is 4-10 membered heterocycloalkyl, which is optionally substituted by 1, 2, 3, or 4 independently selected $R^A$ groups In some embodiments, $R^A$ is $C_{1-6}$ haloalkyl. In some embodiments, $R^A$ is selected from the group consisting of 2-fluoroethyl, 3-fluoropropyl, and 4-fluorobutyl. In some embodiments, $R^A$ is 2-fluoroethyl. In some embodiments, $R^A$ is 3-fluoropropyl. In some embodiments, $R^A$ is 4-fluorobutyl.

In some embodiments,

Hal is selected from the group consisting of Cl, F, and I;

X is selected from the group consisting of O, S, and $NR^N$;

$L^1$ is selected from the group consisting of —$C_{1-6}$ alkylene-, —Y—$C_{1-6}$ alkylene-, and —$C_{1-4}$ alkylene-Y—$C_{1-4}$ alkylene-, wherein the alkylene groups are each optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$L^2$ is selected from the group consisting of —$C_{1-6}$ alkylene-, —$C_{1-6}$ alkylene-Y—, and —$C_{1-4}$ alkylene-Y—$C_{1-4}$ alkylene-, wherein the alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

Y is selected from the group consisting of O, C(O), C(O)$NR^f$, $NR^fC(O)$, and $NR^f$;

each $R^f$ is independently selected from the group consisting of H and $C_{1-3}$ alkyl;

$R^N$ is selected from the group consisting of H, $C_{1-6}$ alkyl, $C_{2-6}$ alkenyl, $C_{2-6}$ alkynyl, and $C_{1-4}$ haloalkyl;

group A is selected from the group consisting of a 5-10 membered heteroaryl and 4-10 membered heterocycloalkyl, each of which is optionally substituted by 1, 2, 3, or 4 independently selected $R^A$ groups;

alternatively, group A is H;

with the proviso that when X is $NR^N$, $L^1$ is —$C_{1-6}$ alkylene-, $L^2$ is —$C_{1-6}$ alkylene-, and $R^N$ is $C_{1-6}$ alkyl, group A is not H; and each $R^A$ is independently selected from the group consisting of OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is Cl;

X is selected from the group consisting of O and $NR^N$;

$L^1$ is —$C_{1-6}$ alkylene-, wherein the alkylene group is optionally substituted with 1, 2, or 3 substituents independently selected from halo, CN, OH, $C_{1-3}$ alkoxy, and amino;

$L^2$ is —$C_{1-6}$ alkylene-, wherein the alkylene group is optionally substituted with 1, 2, or 3 substituents independently selected from halo, CN, OH, $C_{1-3}$ alkoxy, and amino;

$R^N$ is selected from the group consisting of H and $C_{1-6}$ alkyl;

group A is 5 or 6 membered heteroaryl, which is optionally substituted by 1, 2, or 3 independently selected $R^A$ groups;

alternatively, group A is H;

with the proviso that when X is $NR^N$, $L^1$ is —$C_{1-6}$ alkylene-, $L^2$ is —$C_{1-6}$ alkylene-, and $R^N$ is $C_{1-6}$ alkyl, group A is not H; and each $R^A$ is independently selected from the group consisting of OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino In some embodiments, Hal is selected from the group consisting of Cl, F, and I;

X is selected from the group consisting of O, S, S(O), $S(O)_2$, and C(O);

$L^1$ is selected from the group consisting of —$C_{1-6}$ alkylene- and —Y—$C_{1-6}$ alkylene-, wherein the alkylene groups are each optionally substituted with 1, 2, or 3 substituents independently selected from halo, CN, OH, $C_{1-3}$ alkoxy, and amino;

Y is selected from the group consisting of O, C(O), —C(O)NH—, —NHC(O)—, NH, and —N(CH$_3$)—;

$L^2$ is —$C_{1-6}$ alkylene-, wherein the alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

group A is selected from the group consisting of a 5-6 membered heteroaryl and 4-8 membered heterocycloalkyl, each of which is optionally substituted by 1, 2, 3, or 4 independently selected $R^A$ groups; and each $R^A$ is independently selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is selected from the group consisting of O and S;

$L^1$ is —$C_{1-6}$ alkylene-, wherein the alkylene group is optionally substituted with 1, 2, or 3 substituents independently selected from halo, CN, OH, $C_{1-3}$ alkoxy, and amino;

$L^2$ is —$C_{1-6}$ alkylene-, wherein the alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

group A is 5-6 membered heteroaryl, which is optionally substituted by 1, 2, or 3 independently selected $R^A$ groups; and each $R^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is $NR^N$;

$L^1$ is —$C_{1-6}$ alkylene-, wherein the alkylene group is optionally substituted with 1, 2, or 3 substituents independently selected from halo, CN, OH, $C_{1-3}$ alkoxy, and amino;

$L^2$ is —$C_{1-6}$ alkylene-, wherein the alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$R^N$ is selected from the group consisting of H and $C_{1-6}$ alkyl;

group A is selected from the group consisting of a 5 or 6 membered heteroaryl and 4-10 membered heterocycloalkyl, each of which is optionally substituted by 1, 2, 3, or 4 independently selected $R^A$ groups; and $R^A$ is selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is $NR^N$;

$L^1$ is —$C_{1-3}$ alkylene-, wherein the alkylene group is optionally substituted with 1, 2, or 3 substituents independently selected from halo, CN, OH, $C_{1-3}$ alkoxy, and amino;

$L^2$ is —$C_{1-3}$ alkylene-, wherein the alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$R^N$ is selected from the group consisting of H and $C_{1-3}$ alkyl;

group A is 5 or 6 membered heteroaryl, which is optionally substituted by 1, 2, or 3 independently selected $R^A$ groups; and $R^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, the compound of Formula I is a compound of Formula Ia:

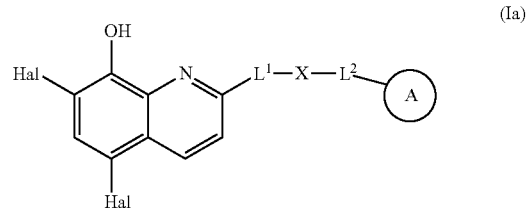

(Ia)

or a pharmaceutically acceptable salt thereof, wherein:

Hal is selected from the group consisting of Cl, F, Br, and I;

X is selected from the group consisting of O, S, S(O), $S(O)_2$, C(O), and $NR^N$;

$L^1$ is selected from the group consisting of —$C_{1-6}$ alkylene-, —Y—$C_{1-6}$ alkylene-, —$C_{1-4}$ alkylene-Y—$C_{1-4}$ alkylene-, or —(O—$C_{1-4}$ alkylene)$_m$-, wherein m is an integer from 1 to 5, and wherein the alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

$L^2$ is selected from the group consisting of —$C_{1-6}$ alkylene-, —$C_{1-6}$ alkylene-Y—, —$C_{1-4}$ alkylene-Y—$C_{1-4}$ alkylene-, and —($C_{1-4}$ alkylene-O—)$_m$—, wherein m is an integer from 1 to 5, and wherein the alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

each Y is independently selected from the group consisting of O, S, S(O), $S(O)_2$, C(O), C(O)$NR^f$, $NR^f$C(O), $S(O)_2NR^f$, $NR^fS(O)_2$, and $NR^f$;

each $R^f$ is independently selected from the group consisting of H and $C_{1-3}$ alkyl;

$R^N$ is selected from the group consisting of H, $C_{1-6}$ alkyl, $C_{2-6}$ alkenyl, $C_{2-6}$ alkynyl, $C_{1-4}$ haloalkyl, $C_{3-10}$ cycloalkyl, 4-10 membered heterocycloalkyl, wherein the $C_{1-6}$ alkyl, $C_{2-6}$ alkenyl, $C_{2-6}$ alkynyl, $C_{1-4}$ haloalkyl, $C_{3-10}$ cycloalkyl, and 4-10 membered heterocycloalkyl are each optionally substituted by 1, 2, 3, or 4 independently selected $R^g$ groups;

group A is selected from the group consisting of a 5-10 membered heteroaryl and 4-10 membered heterocycloalkyl, each of which is optionally substituted by 1, 2, 3, or 4 independently selected $R^A$ groups;

alternatively, group A is H;

with the proviso that when X is $NR^N$, $L^1$ is —$C_{1-6}$ alkylene-, $L^2$ is —$C_{1-6}$ alkylene-, and $R^N$ is $C_{1-6}$ alkyl, group A is not H;

each $R^A$ is independently selected from the group consisting of OH, $NO_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^g$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments of a compound of Formula Ia, Hal is selected from the group consisting of Cl, F, and I. In some embodiments of a compound of Formula Ia, Hal is Cl. In some embodiments of a compound of Formula Ia, Hal is F. In some embodiments of a compound of Formula Ia, Hal is I. In some embodiments of a compound of Formula Ia, both Hal groups are Cl. In some embodiments of a compound of Formula Ia, both Hal groups are F. In some embodiments of a compound of Formula Ia, both Hal groups are I. In some embodiments of a compound of Formula Ia, one of the Hal groups is Cl and another Hal group is F. In some embodiments of a compound of Formula Ia, one of the Hal groups is Cl and another Hal group is I. In some embodiments of a compound of Formula Ia, one of the Hal groups is F and another Hal group is I.

In some embodiments of a compound of Formula Ia, X is selected from the group consisting of O, S, and $NR^N$. In some embodiments of a compound of Formula Ia, X is selected from the group consisting of O and $NR^N$. In some embodiments of a compound of Formula Ia, X is selected from the group consisting of O and —N($C_{1-6}$ alkyl)-. In some embodiments of a compound of Formula Ia, X is selected from the group consisting of O and —N($CH_3$)—. In some embodiments of a compound of Formula Ia, X is O. In some embodiments of a compound of Formula Ia, X is $NR^N$. In some embodiments of a compound of Formula Ia, —N($C_{1-6}$ alkyl)-. In some embodiments of a compound of Formula Ia, —N($CH_3$)—.

In some embodiments of a compound of Formula Ia, $L^1$ is selected from the group consisting of —$C_{1-6}$ alkylene-, —Y—$C_{1-6}$ alkylene-, and —$C_{1-4}$ alkylene-Y—$C_{1-4}$ alkylene-, wherein the alkylene groups are each optionally substituted with 1, 2, or 3 substituents independently selected from halo, CN, OH, $C_{1-3}$ alkoxy, amino, $C_{1-3}$ alkylamino, and di($C_{1-3}$ alkyl)amino.

In some embodiments of a compound of Formula Ia, $L^1$ is selected from the group consisting of —$C_{1-6}$ alkylene-, and —Y—$C_{1-6}$ alkylene-, wherein the alkylene groups are each optionally substituted with 1, 2, or 3 substituents independently selected from halo, CN, OH, $C_{1-3}$ alkoxy, and amino.

In some embodiments of a compound of Formula Ia, $L^1$ is —$C_{1-6}$ alkylene-, wherein the alkylene group is optionally substituted with 1, 2, or 3 substituents independently selected from halo, CN, OH, $C_{1-3}$ alkoxy, and amino. In some embodiments of a compound of Formula Ia, $L^1$ is methylene.

In some embodiments of a compound of Formula Ia, $L^2$ is selected from the group consisting of —$C_{1-6}$ alkylene-, —$C_{1-6}$ alkylene-Y—, and —$C_{1-4}$ alkylene-Y—$C_{1-4}$ alkylene-, wherein the alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments of a compound of Formula Ia, $L^2$ is selected from the group consisting of —$C_{1-6}$ alkylene- and —$C_{1-6}$ alkylene-Y—, wherein the alkylene groups are each optionally substituted with 1, 2, or 3 substituents independently selected from halo, CN, OH, $C_{1-3}$ alkoxy, and amino.

In some embodiments of a compound of Formula Ia, $L^2$ is —$C_{1-6}$ alkylene-, wherein the alkylene group is optionally substituted with 1, 2, or 3 substituents independently selected from halo, CN, OH, $C_{1-3}$ alkoxy, and amino. In some embodiments of a compound of Formula Ia, $L^2$ is selected from the group consisting of methylene, ethylene, and butylene.

In some embodiments of a compound of Formula Ia, Y is selected from the group consisting of O, C(O), C(O)$NR^f$, $NR^fC(O)$, and $NR^f$. In some embodiments of a compound of Formula Ia, Y is selected from the group consisting of O, C(O), —C(O)NH—, —NHC(O)—, NH, and —N($CH_3$)—.

In some embodiments of a compound of Formula Ia, $R^N$ is selected from the group consisting of H, $C_{1-6}$ alkyl, $C_{2-6}$ alkenyl, $C_{2-6}$ alkynyl, $C_{1-4}$ haloalkyl. In some embodiments of a compound of Formula Ia, $R^N$ is selected from the group consisting of H and $C_{1-6}$ alkyl. In some embodiments of a compound of Formula Ia, $R^N$ is H. In some embodiments of a compound of Formula Ia, $R^N$ is $C_{1-6}$ alkyl. In some embodiments of a compound of Formula Ia, $R^N$ is $C_{1-4}$ haloalkyl. In some embodiments of a compound of Formula Ia, $R^N$ is —$CH_3$.

In some embodiments of a compound of Formula Ia, X is selected from the group consisting of O, S, S(O), $S(O)_2$, and C(O); and group A is H. In some embodiments of a compound of Formula Ia, X is selected from the group consisting of O and S; and group A is H. In some embodiments of a compound of Formula Ia, X is O; and group A is H. In some aspects of these embodiments, $L^1$ is selected from the group consisting of —$C_{1-6}$ alkylene-, and —Y—$C_{1-6}$ alkylene-, wherein the alkylene groups are each optionally substituted with 1, 2, or 3 substituents independently selected from halo, CN, OH, $C_{1-3}$ alkoxy, and amino. In some aspects of these embodiments, $L^1$ is —$C_{1-6}$ alkylene-, wherein the alkylene group is optionally substituted with 1, 2, or 3 substituents independently selected from halo, CN, OH, $C_{1-3}$ alkoxy, and amino. In some aspects of these embodiments, $L^1$ is methylene. In some aspects of these embodiments, $L^2$ is —$C_{1-6}$ alkylene-, wherein the alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino. In some aspects of these embodiments, $L^2$ is selected from the group consisting of ethylene and butylene, each of which is optionally substituted with 1, 2, or 3 substituents independently selected from the group consisting of halo, CN, OH, $C_{1-3}$ alkoxy, amino, methylamino, and dimethylamino. In some aspects of these embodiments, $L^2$ is selected from the group consisting of ethylene and butylene, each of which is optionally substituted with 1, 2, or 3 halogen substituents independently selected from Cl, F, and I. In some aspects of these embodiments, $L^2$ is selected from the group consisting of ethylene and butylene, each of which is optionally substituted with one F. In some aspects of these embodiments, $L^2$ is fluoroethylene. In some aspects of these embodiments, $L^2$ is fluorobutylene.

In some embodiments of a compound of Formula Ia, X is $NR^N$; and group A is selected from the group consisting of a 5 or 6 membered heteroaryl and 4-10 membered heterocycloalkyl, each of which is optionally substituted by 1, 2, 3, or 4 independently selected $R^A$ groups. In some embodiments of a compound of Formula Ia, X is $NR^N$; and group A is a 5 or 6 membered heteroaryl, which is optionally substituted by 1, 2, or 3 independently selected $R^A$ groups. In some embodiments of a compound of Formula Ia, X is —N(C$_{1-6}$ alkyl)-; and group A is a 5 or 6 membered heteroaryl, which is optionally substituted by 1, 2, or 3 independently selected $R^A$ groups. In some embodiments of a compound of Formula Ia, X is —N(C$_{1-6}$ alkyl)-; and group A is triazolyl, which is optionally substituted by 1, 2, or 3 independently selected $R^A$ groups. In some embodiments of a compound of Formula Ia, X is —N(CH$_3$)—; and group A is triazolyl, which is optionally substituted by 1, 2, or 3 independently selected $R^A$ groups. In some embodiments of a compound of Formula Ia, X is —N(CH$_3$)—; and group A is a triazolyl of Formula A-1:

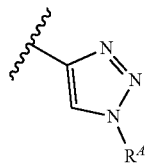

(A-1)

In some aspects of these embodiments, $L^1$ is —C$_{1-6}$ alkylene-, wherein the alkylene group is optionally substituted with 1, 2, or 3 substituents independently selected from halo, CN, OH, C$_{1-3}$ alkoxy, and amino. In some aspects of these embodiments, $L^1$ is methylene. In some aspects of these embodiments, $L^2$ is —C$_{1-6}$ alkylene-, wherein the alkylene group is optionally substituted with 1, 2, or 3 substituents independently selected from halo, CN, OH, C$_{1-3}$ alkoxy, amino, C$_{1-3}$ alkylamino, and di(C$_{1-3}$ alkyl)amino. In some aspects of these embodiments, $L^2$ is methylene. In some aspects of these embodiments, $R^A$ is selected from the group consisting of OH, NO$_2$, CN, halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino. In some aspects of these embodiments, $R^A$ is selected from the group consisting of halo, C$_{1-6}$ alkyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, and di(C$_{1-6}$ alkyl)amino. In some aspects of these embodiments, $R^A$ is C$_{1-6}$ haloalkyl. In some aspects of these embodiments, $R^A$ is selected from the group consisting of 2-fluoroethyl, 3-fluoropropyl, and 4-fluorobutyl. In some aspects of these embodiments, $R^A$ is 2-fluoroethyl. In some aspects of these embodiments, $R^A$ is 3-fluoropropyl. In some aspects of these embodiments, $R^A$ is 4-fluorobutyl.

In some embodiments of a compound of Formula Ia, group A is H.

In some embodiments of a compound of Formula Ia, group A is selected from the group consisting of a 5 or 6 membered heteroaryl and 4-10 membered heterocycloalkyl, each of which is optionally substituted by 1, 2, 3, or 4 independently selected $R^A$ groups.

In some embodiments of a compound of Formula Ia, group A is 5 or 6 membered heteroaryl which is optionally substituted by 1, 2, 3, or 4 independently selected $R^A$ groups. In some embodiments of a compound of Formula Ia, group A is 5 membered heteroaryl which is optionally substituted by 1, 2, or 3 independently selected $R^A$ groups. In some embodiments of a compound of Formula Ia, group A is 6 membered heteroaryl which is optionally substituted by 1, 2, or 3 independently selected $R^A$ groups.

In some embodiments of a compound of Formula Ia, group A is selected from the group consisting of pyridinyl, triazinyl, pyridazinyl, pyrimidinyl, and pyrazinyl, each of which is optionally substituted by 1, 2, 3, or 4 independently selected $R^A$ groups. In some embodiments of a compound of Formula Ia, group A is selected from the group consisting of triazolyl, pyrazolyl, imidazolyl, isoxazolyl, oxazolyl, isothiazolyl, thiazolyl, furanyl, and thiophenyl, each of which is optionally substituted by 1, 2, 3, or 4 independently selected $R^A$ groups.

In some embodiments of a compound of Formula Ia, group A is triazolyl, which is optionally substituted by 1, 2, 3, or 4 independently selected $R^A$ groups. In some embodiments of a compound of Formula Ia, group A is triazolyl, which is optionally substituted by 1 $R^A$ group.

In some embodiments of a compound of Formula Ia, group A is a triazolyl of Formula A-1:

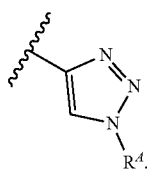

(A-1)

In some embodiments of a compound of Formula Ia, group A is 4-10 membered heterocycloalkyl, which is optionally substituted by 1, 2, 3, or 4 independently selected $R^A$ groups In some embodiments of a compound of Formula Ia, $R^A$ is C$_{1-6}$ haloalkyl. In some embodiments of a compound of Formula Ia, $R^A$ is selected from the group consisting of 2-fluoroethyl, 3-fluoropropyl, and 4-fluorobutyl. In some embodiments of a compound of Formula Ia, $R^A$ is 2-fluoroethyl. In some embodiments of a compound of Formula Ia, $R^A$ is 3-fluoropropyl. In some embodiments of a compound of Formula Ia, $R^A$ is 4-fluorobutyl.

In some embodiments, the compound of Formula Ia is a compound of Formula Ib:

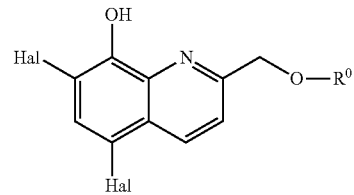

(Ib)

or a pharmaceutically acceptable salt thereof, wherein:
Hal is selected from the group consisting of Cl, F, and I; and
$R^0$ is —C$_{1-6}$ alkyl, which is optionally substituted with 1, 2, or 3 substituents independently selected from halo, CN, OH, C$_{1-3}$ alkoxy, amino, C$_{1-3}$ alkylamino, and di(C$_{1-3}$ alkyl) amino.

In some embodiments of a compound of Formula Ib, Hal is Cl. In some embodiments of a compound of Formula Ib, Hal is F. In some embodiments of a compound of Formula Ib, Hal is I. In some embodiments of a compound of Formula Ib, both Hal groups are Cl. In some embodiments of a compound of Formula Ib, both Hal groups are F. In some embodiments of a compound of Formula Ib, both Hal groups are I. In some embodiments of a compound of Formula Ib, one of the Hal groups is Cl and another Hal group is F. In some embodiments of a compound of Formula Ib, one of the Hal groups is Cl and another Hal group is I. In some embodiments of a compound of Formula Ib, one of the Hal groups is F and another Hal group is I.

In some embodiments of a compound of Formula Ib, $R^O$ is $C_{1-6}$ haloalkyl. In some embodiments of a compound of Formula Ib, $R^O$ is $C_{1-4}$ haloalkyl.

In some embodiments of a compound of Formula Ib, $R^O$ is 2-fluoroethyl or 4-fluorobutyl. In some embodiments of a compound of Formula Ib, $R^O$ is 2-fluoroethyl. In some embodiments of a compound of Formula Ib, $R^O$ is 4-fluorobutyl.

In some embodiments, the compound of Formula Ia is a compound of Formula Ic:

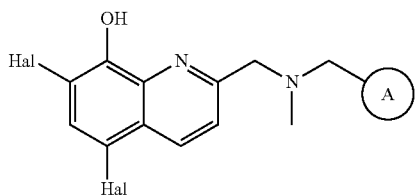

(Ic)

or a pharmaceutically acceptable salt thereof, wherein:
Hal is selected from the group consisting of Cl, F, and I; and
group A is selected from the group consisting of a 5-6 membered heteroaryl and 4-10 membered heterocycloalkyl, each of which is optionally substituted by 1, 2, 3, or 4 independently selected $R^A$ groups.

In some embodiments of a compound of Formula Ic, Hal is Cl. In some embodiments of a compound of Formula Ic, Hal is F. In some embodiments of a compound of Formula Ic, Hal is I. In some embodiments of a compound of Formula Ic, both Hal groups are Cl. In some embodiments of a compound of Formula Ic, both Hal groups are F. In some embodiments of a compound of Formula Ic, both Hal groups are I. In some embodiments of a compound of Formula Ic, one of the Hal groups is Cl and another Hal group is F. In some embodiments of a compound of Formula Ic, one of the Hal groups is Cl and another Hal group is I. In some embodiments of a compound of Formula Ic, one of the Hal groups is F and another Hal group is I.

In some embodiments of a compound of Formula Ic, group A is 5 or 6 membered heteroaryl which is optionally substituted by 1, 2, 3, or 4 independently selected $R^A$ groups. In some embodiments of a compound of Formula Ic, group A is 5 membered heteroaryl which is optionally substituted by 1, 2, or 3 independently selected $R^A$ groups. In some embodiments of a compound of Formula Ic, group A is 6 membered heteroaryl which is optionally substituted by 1, 2, or 3 independently selected $R^A$ groups.

In some embodiments of a compound of Formula Ic, group A is selected from the group consisting of pyridinyl, triazinyl, pyridazinyl, pyrimidinyl, and pyrazinyl, each of which is optionally substituted by 1, 2, 3, or 4 independently selected $R^A$ groups. In some embodiments of a compound of Formula Ic, group A is selected from the group consisting of triazolyl, pyrazolyl, imidazolyl, isoxazolyl, oxazolyl, isothiazolyl, thiazolyl, furanyl, and thiophenyl, each of which is optionally substituted by 1, 2, 3, or 4 independently selected $R^A$ groups.

In some embodiments of a compound of Formula Ic, group A is triazolyl, which is optionally substituted by 1, 2, or 3 independently selected $R^A$ groups.

In some embodiments of a compound of Formula Ic, group A is triazolyl, which is optionally substituted by 1 $R^A$ group.

In some embodiments of a compound of Formula Ic, group A is a triazolyl of Formula A-Ic:

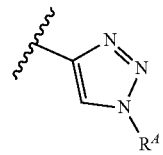

(A-1c)

In some embodiments of a compound of Formula Ic, $R^A$ is selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments of a compound of Formula Ic, $R^A$ is selected from the group consisting of $C_{1-6}$ alkyl, $C_{1-6}$ haloalkyl, cyano-$C_{1-3}$ alkyl, and HO—$C_{1-3}$ alkyl.

In some embodiments of a compound of Formula Ic, $R^A$ is $C_{1-6}$ haloalkyl. In some embodiments of a compound of Formula Ic, $R^A$ is selected from the group consisting of 2-fluoroethyl, 3-fluoropropyl, and 4-fluorobutyl. In some embodiments of a compound of Formula Ic, $R^A$ is 2-fluoroethyl. In some embodiments of a compound of Formula Ic, $R^A$ is 3-fluoropropyl. In some embodiments of a compound of Formula Ic, $R^A$ is 4-fluorobutyl.

In some embodiments, the compound of Formula I, Ia, or Ib is selected from the group consisting of:

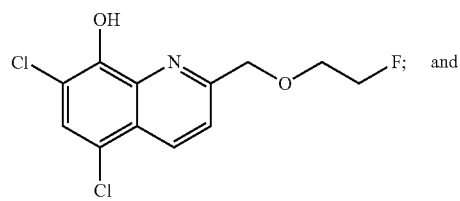

and

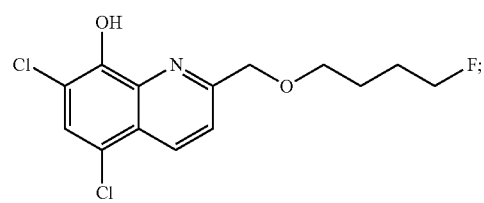

or a pharmaceutically acceptable salt of any of the aforementioned.

In some embodiments, the compound of Formula I, Ia, or Ic is selected from the group consisting of:

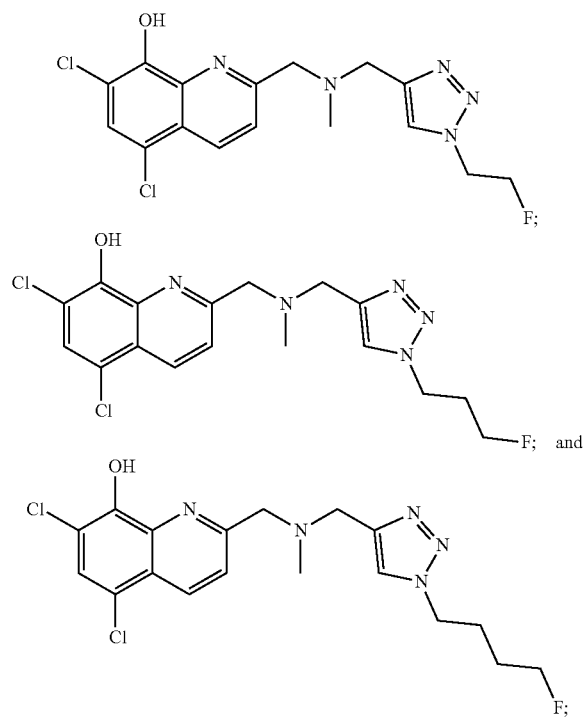

or a pharmaceutically acceptable salt thereof.

In some embodiments, a salt of a compound of Formulae I, Ia, Ib, and Ic is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formulae I, Ia, Ib, and Ic include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formulae I, Ia, Ib, and Ic include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formulae I, Ia, Ib, and Ic, or pharmaceutically acceptable salts thereof, are substantially isolated.

Labeled Compounds

Another aspect of the present application relates to labeled compounds of Formulae II, IIa, IIb, IIc, and III, that would be useful in imaging techniques, diagnosing and monitoring treatment of various diseases and conditions described herein. Such compounds are labeled in so far as each compound includes at least one radioisotope. In some embodiments, such compounds include one radioisotope.

In some embodiments, the at least one radioisotope is a positron emitter.

In some embodiments, the positron emitter is selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{110m}$In, $^{118}$Sb, $^{120}$I, $^{121}$I, $^{122}$I, and $^{124}$I.

In some embodiments, the positron emitter is $^{11}$C or $^{18}$F.

In some embodiments, the positron emitter is selected from the group consisting of $^{120}$I, $^{121}$I, $^{122}$I, and $^{124}$I.

In some embodiments, the positron emitter is $^{124}$I.

In some embodiments, the at least one radioisotope is a gamma emitter.

In some embodiments, gamma emitter is selected from the group consisting of $^{99m}$Tc, $^{125}$I, $^{131}$I, and $^{123}$I.

In some embodiments, the gamma emitter is $^{123}$I.

Accordingly, the present application provides, inter alia, a compound of Formula (II):

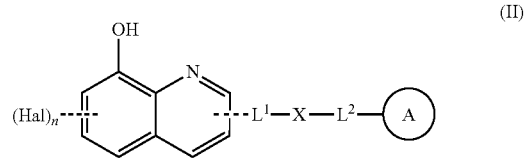

(II)

or a pharmaceutically acceptable salt thereof, wherein:

Hal is selected from the group consisting of Cl, F, Br, and I;

n is 1, 2, or 3;

X is selected from the group consisting of O, S, S(O), S(O)$_2$, C(O), and NR$^N$;

$L^1$ is selected from the group consisting of —$C_{1-6}$ alkylene-, —Y—$C_{1-6}$ alkylene-, —$C_{1-4}$ alkylene-Y—$C_{1-4}$ alkylene-, and —(O—$C_{1-4}$ alkylene)$_m$-, wherein m is an integer from 1 to 5, and wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

$L^2$ is selected from the group consisting of —$C_{1-6}$ alkylene-, —$C_{1-6}$ alkylene-Y—, —$C_{1-4}$ alkylene-Y—$C_{1-4}$ alkylene-, and —($C_{1-4}$ alkylene-O—)$_m$—, wherein m is an integer from 1 to 5, and wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

each Y is independently selected from the group consisting of O, S, S(O), S(O)$_2$, C(O), C(O)NR$^f$, NR$^f$C(O), S(O)$_2$NR$^f$, NR$^f$S(O)$_2$, and NR$^f$;

each R$^f$ is independently selected from the group consisting of H and $C_{1-3}$ alkyl;

R$^N$ is selected from the group consisting of H, $C_{1-6}$ alkyl, $C_{2-6}$ alkenyl, $C_{2-6}$ alkynyl, $C_{1-4}$ haloalkyl, $C_{3-10}$ cycloalkyl, and 4-10 membered heterocycloalkyl, wherein said $C_{1-6}$ alkyl, $C_{2-6}$ alkenyl, $C_{2-6}$ alkynyl, $C_{1-4}$ haloalkyl, $C_{3-10}$ cycloalkyl, and 4-10 membered heterocycloalkyl are each optionally substituted by 1, 2, 3, or 4 independently selected R$^g$ groups;

group A is selected from the group consisting of a 5-10 membered heteroaryl and 4-10 membered heterocycloalkyl, each of which is optionally substituted by 1, 2, 3, or 4 independently selected R$^A$ groups;

alternatively, group A is H;

with the proviso that when X is NR$^N$, $L^1$ is —$C_{1-6}$ alkylene-, $L^2$ is —$C_{1-6}$ alkylene-, and R$^N$ is $C_{1-6}$ alkyl, group A is not H;

each R$^A$ is independently selected from the group consisting of OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each R$^g$ is independently selected from the group consisting of OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and wherein the compound of Formula (II) comprises at least one radioisotope.

In some embodiments, Hal is selected from the group consisting of Cl, F, and I. In some embodiments, Hal is Cl. In some embodiments, Hal is F. In some embodiments, Hal is I. In some embodiments, both Hal groups are Cl. In some embodiments, both Hal groups are F. In some embodiments, both Hal groups are I. In some embodiments, one of the Hal groups is Cl and another Hal group is F. In some embodiments, one of the Hal groups is Cl and another Hal group is I. In some embodiments, one of the Hal groups is F and another Hal group is I. In some embodiments, Hal comprises at least one radioisotope (e.g., $^{18}$F).

In some embodiments, X is selected from the group consisting of O, S, and NR$^N$. In some embodiments, X is selected from the group consisting of O and NR$^N$. In some embodiments, X is selected from the group consisting of O and —N($C_{1-6}$ alkyl)-. In some embodiments, X is selected from the group consisting of O and —N(CH$_3$)—. In some embodiments, X is O. In some embodiments, X is NR$^N$. In some embodiments, —N($C_{1-6}$ alkyl)-. In some embodiments, —N(CH$_3$)—.

In some embodiments, $L^1$ is selected from the group consisting of —$C_{1-6}$ alkylene-, —Y—$C_{1-6}$ alkylene-, and —$C_{1-4}$ alkylene-Y—$C_{1-4}$ alkylene-, wherein said alkylene groups are each optionally substituted with 1, 2, or 3 substituents independently selected from halo, CN, OH, $C_{1-3}$ alkoxy, amino, $C_{1-3}$ alkylamino, and di($C_{1-3}$ alkyl)amino.

In some embodiments, $L^1$ is selected from the group consisting of —$C_{1-6}$ alkylene-, and —Y—$C_{1-6}$ alkylene-, wherein said alkylene groups are each optionally substituted with 1, 2, or 3 substituents independently selected from halo, CN, OH, $C_{1-3}$ alkoxy, and amino.

In some embodiments, $L^1$ is —$C_{1-6}$ alkylene-, wherein said alkylene group is optionally substituted with 1, 2, or 3 substituents independently selected from halo, CN, OH, $C_{1-3}$ alkoxy, and amino. In some embodiments, $L^1$ is methylene.

In some embodiments, $L^2$ is selected from the group consisting of —$C_{1-6}$ alkylene-, —$C_{1-6}$ alkylene-Y—, and —$C_{1-4}$ alkylene-Y—$C_{1-4}$ alkylene-, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments, $L^2$ is selected from the group consisting of —$C_{1-6}$ alkylene- and —$C_{1-6}$ alkylene-Y—, wherein said alkylene groups are each optionally substituted with 1, 2, or 3 substituents independently selected from halo, CN, OH, $C_{1-3}$ alkoxy, and amino.

In some embodiments, $L^2$ is —$C_{1-6}$ alkylene-, wherein said alkylene group is optionally substituted with 1, 2, or 3 substituents independently selected from halo, CN, OH, $C_{1-3}$ alkoxy, and amino. In some embodiments, $L^2$ is selected from the group consisting of methylene, ethylene, and butylene.

In some embodiments, Y is selected from the group consisting of O, C(O), C(O)NR$^f$, NR$^f$C(O), and NR$^f$. In some embodiments, Y is selected from the group consisting of O, C(O), —C(O)NH—, —NHC(O)—, NH, and —N(CH$_3$)—.

In some embodiments, R$^N$ is selected from the group consisting of H, $C_{1-6}$ alkyl, $C_{2-6}$ alkenyl, $C_{2-6}$ alkynyl, $C_{1-4}$ haloalkyl. In some embodiments, R$^N$ is selected from the group consisting of H and $C_{1-6}$ alkyl. In some embodiments, R$^N$ is H. In some embodiments, R$^N$ is $C_{1-6}$ alkyl. In some embodiments, R$^N$ is $C_{1-4}$ haloalkyl. In some embodiments, R$^N$ is —CH$_3$.

In some embodiments, X is selected from the group consisting of O, S, S(O), S(O)$_2$, and C(O); and group A is H. In some embodiments, X is selected from the group consisting of O and S; and group A is H. In some embodiments, X is O; and group A is H. In some aspects of these embodiments, $L^1$ is selected from the group consisting of —$C_{1-6}$ alkylene-, and —Y—$C_{1-6}$ alkylene-, wherein said alkylene groups are each optionally substituted with 1, 2, or 3 substituents independently selected from halo, CN, OH, $C_{1-3}$ alkoxy, and amino. In some aspects of these embodiments, $L^1$ is —$C_{1-6}$ alkylene-, wherein said alkylene group is optionally substituted with 1, 2, or 3 substituents independently selected from halo, CN, OH, $C_{1-3}$ alkoxy, and amino. In some aspects of these embodiments, $L^1$ is methylene. In some aspects of these embodiments, $L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino. In some aspects of these embodiments, $L^2$ is selected from the group consisting of ethylene and butylene, each of which is optionally substituted with 1, 2, or 3 substituents independently selected from the group consisting of halo, CN, OH, $C_{1-3}$ alkoxy, amino, methylamino, and dimethylamino. In some aspects of these embodiments, $L^2$ is selected from the group consisting of ethylene and butylene, each of which is optionally substituted with 1, 2, or 3 halogen substituents independently selected from Cl, F, and I. In some aspects of these embodiments, $L^2$ is selected from the group consisting of ethylene and butylene, each of which is optionally substituted with one F. In some aspects of these embodiments, $L^2$ is fluoroethylene. In some aspects of these embodiments, $L^2$ is fluorobutylene.

In some embodiments, X is $NR^N$; and group A is selected from the group consisting of a 5 or 6 membered heteroaryl and 4-10 membered heterocycloalkyl, each of which is optionally substituted by 1, 2, 3, or 4 independently selected $R^A$ groups. In some embodiments, X is $NR^N$; and group A is a 5 or 6 membered heteroaryl, which is optionally substituted by 1, 2, or 3 independently selected $R^A$ groups. In some embodiments, X is —N($C_{1-6}$ alkyl)-; and group A is a 5 or 6 membered heteroaryl, which is optionally substituted by 1, 2, or 3 independently selected $R^A$ groups. In some embodiments, X is —N($C_{1-6}$ alkyl)-; and group A is triazolyl, which is optionally substituted by 1, 2, or 3 independently selected $R^A$ groups. In some embodiments, X is —N(CH$_3$)—; and group A is triazolyl, which is optionally substituted by 1, 2, or 3 independently selected $R^A$ groups. In some embodiments, X is —N(CH$_3$)—; and group A is a triazolyl of Formula A-1:

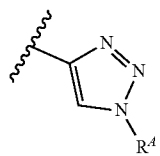

(A-1)

In some aspects of these embodiments, $L^1$ is —$C_{1-6}$ alkylene-, wherein said alkylene group is optionally substituted with 1, 2, or 3 substituents independently selected from halo, CN, OH, $C_{1-3}$ alkoxy, and amino. In some aspects of these embodiments, $L^1$ is methylene. In some aspects of these embodiments, $L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino. In some aspects of these embodiments, $L^2$ is methylene. In some aspects of these embodiments, $R^A$ is selected from the group consisting of OH, NO$_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl) amino. In some aspects of these embodiments, $R^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino. In some aspects of these embodiments, $R^A$ is $C_{1-6}$ haloalkyl. In some aspects of these embodiments, $R^A$ is selected from the group consisting of 2-fluoroethyl, 3-fluoropropyl, and 4-fluorobutyl. In some aspects of these embodiments, $R^A$ is 2-fluoroethyl. In some aspects of these embodiments, $R^A$ is 3-fluoropropyl. In some aspects of these embodiments, $R^A$ is 4-fluorobutyl.

In some embodiments, group A is H.

In some embodiments, group A is selected from the group consisting of a 5 or 6 membered heteroaryl and 4-10 membered heterocycloalkyl, each of which is optionally substituted by 1, 2, 3, or 4 independently selected $R^A$ groups.

In some embodiments, group A is 5 or 6 membered heteroaryl which is optionally substituted by 1, 2, 3, or 4 independently selected $R^A$ groups. In some embodiments, group A is 5 membered heteroaryl which is optionally substituted by 1, 2, or 3 independently selected $R^A$ groups. In some embodiments, group A is 6 membered heteroaryl which is optionally substituted by 1, 2, or 3 independently selected $R^A$ groups.

In some embodiments, group A is selected from the group consisting of pyridinyl, triazinyl, pyridazinyl, pyrimidinyl, and pyrazinyl, each of which is optionally substituted by 1, 2, 3, or 4 independently selected $R^A$ groups. In some embodiments, group A is selected from the group consisting of triazolyl, pyrazolyl, imidazolyl, isoxazolyl, oxazolyl, isothiazolyl, thiazolyl, furanyl, and thiophenyl, each of which is optionally substituted by 1, 2, 3, or 4 independently selected $R^A$ groups.

In some embodiments, group A is triazolyl, which is optionally substituted by 1, 2, 3, or 4 independently selected $R^A$ groups. In some embodiments, group A is triazolyl, which is optionally substituted by 1 $R^A$ group.

In some embodiments, group A is a triazolyl of Formula A-1:

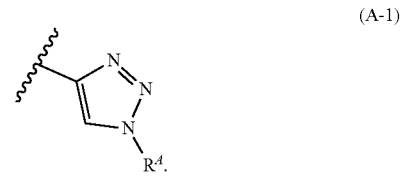

(A-1)

In some embodiments, group A is 4-10 membered heterocycloalkyl, which is optionally substituted by 1, 2, 3, or 4 independently selected $R^A$ groups In some embodiments, $R^A$ is $C_{1-6}$ haloalkyl. In some embodiments, $R^A$ is selected from the group consisting of 2-fluoroethyl, 3-fluoropropyl, and 4-fluorobutyl. In some embodiments, $R^A$ is 2-fluoroethyl. In some embodiments, $R^A$ is 3-fluoropropyl. In some embodiments, $R^A$ is 4-fluorobutyl.

In some embodiments,

Hal is selected from the group consisting of Cl, F, and I;

X is selected from the group consisting of O, S, and $NR^N$;

$L^1$ is selected from the group consisting of —$C_{1-6}$ alkylene-, —Y—$C_{1-6}$ alkylene-, and —$C_{1-4}$ alkylene-Y—$C_{1-4}$ alkylene-, wherein said alkylene groups are each optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

$L^2$ is selected from the group consisting of —$C_{1-6}$ alkylene-, —$C_{1-6}$ alkylene-Y—, and —$C_{1-4}$ alkylene-Y—$C_{1-4}$ alkylene-, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

Y is selected from the group consisting of O, C(O), C(O)NR$^f$, NR$^f$C(O), and NR$^f$;

each R$^f$ is independently selected from the group consisting of H and $C_{1-3}$ alkyl;

R$^N$ is selected from the group consisting of H, $C_{1-6}$ alkyl, $C_{2-6}$ alkenyl, $C_{2-6}$ alkynyl, and $C_{1-4}$ haloalkyl;

group A is selected from the group consisting of a 5-10 membered heteroaryl and 4-10 membered heterocycloalkyl, each of which is optionally substituted by 1, 2, 3, or 4 independently selected R$^A$ groups;

alternatively, group A is H;

with the proviso that when X is NR$^N$, $L^1$ is —$C_{1-6}$ alkylene-, $L^2$ is —$C_{1-6}$ alkylene-, and R$^N$ is $C_{1-6}$ alkyl, group A is not H; and each R$^A$ is independently selected from the group consisting of OH, NO$_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is Cl;

X is selected from the group consisting of O and NR$^N$;

$L^1$ is —$C_{1-6}$ alkylene-, wherein said alkylene group is optionally substituted with 1, 2, or 3 substituents independently selected from halo, CN, OH, $C_{1-3}$ alkoxy, and amino;

$L^2$ is —$C_{1-6}$ alkylene-, wherein said alkylene group is optionally substituted with 1, 2, or 3 substituents independently selected from halo, CN, OH, $C_{1-3}$ alkoxy, and amino;

R$^N$ is selected from the group consisting of H and $C_{1-6}$ alkyl;

group A is 5 or 6 membered heteroaryl, which is optionally substituted by 1, 2, or 3 independently selected R$^A$ groups;

alternatively, group A is H;

with the proviso that when X is NR$^N$, $L^1$ is —$C_{1-6}$ alkylene-, $L^2$ is —$C_{1-6}$ alkylene-, and R$^N$ is $C_{1-6}$ alkyl, group A is not H; and each R$^A$ is independently selected from the group consisting of OH, NO$_2$, CN, halo, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino In some embodiments, Hal is selected from the group consisting of Cl, F, and I;

X is selected from the group consisting of O, S, S(O), S(O)$_2$, and C(O);

$L^1$ is selected from the group consisting of —$C_{1-6}$ alkylene- and —Y—$C_{1-6}$ alkylene-, wherein said alkylene groups are each optionally substituted with 1, 2, or 3 substituents independently selected from halo, CN, OH, $C_{1-3}$ alkoxy, and amino;

Y is selected from the group consisting of O, C(O), —C(O)NH—, —NHC(O)—, NH, and —N(CH$_3$)—;

$L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

group A is selected from the group consisting of a 5-6 membered heteroaryl and 4-8 membered heterocycloalkyl, each of which is optionally substituted by 1, 2, 3, or 4 independently selected R$^A$ groups; and each R$^A$ is independently selected from the group consisting of OH, NO$_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is selected from the group consisting of O and S;

$L^1$ is —$C_{1-6}$ alkylene-, wherein said alkylene group is optionally substituted with 1, 2, or 3 substituents independently selected from halo, CN, OH, $C_{1-3}$ alkoxy, and amino;

$L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

group A is 5-6 membered heteroaryl, which is optionally substituted by 1, 2, or 3 independently selected R$^A$ groups; and each R$^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is NR$^N$;

$L^1$ is —$C_{1-6}$ alkylene-, wherein said alkylene group is optionally substituted with 1, 2, or 3 substituents independently selected from halo, CN, OH, $C_{1-3}$ alkoxy, and amino;

$L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

R$^N$ is selected from the group consisting of H and $C_{1-6}$ alkyl;

group A is selected from the group consisting of a 5 or 6 membered heteroaryl and 4-10 membered heterocycloalkyl, each of which is optionally substituted by 1, 2, 3, or 4 independently selected R$^A$ groups; and R$^A$ is selected from the group consisting of OH, NO$_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments,

Hal is selected from the group consisting of Cl, F, and I;

X is NR$^N$;

$L^1$ is —$C_{1-3}$ alkylene-, wherein said alkylene group is optionally substituted with 1, 2, or 3 substituents independently selected from halo, CN, OH, $C_{1-3}$ alkoxy, and amino;

$L^2$ is —$C_{1-3}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino;

R$^N$ is selected from the group consisting of H and $C_{1-3}$ alkyl;

group A is 5 or 6 membered heteroaryl, which is optionally substituted by 1, 2, or 3 independently selected R$^A$ groups; and R$^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments, the compound of Formula II is a compound of Formula IIa:

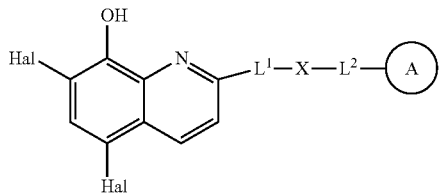

or a pharmaceutically acceptable salt thereof, wherein:

Hal is selected from the group consisting of Cl, F, Br, and I;

X is selected from the group consisting of O, S, S(O), S(O)$_2$, C(O), and NR$^N$;

L$^1$ is selected from the group consisting of —C$_{1-6}$ alkylene-, —Y—C$_{1-6}$ alkylene-, —C$_{1-4}$ alkylene-Y—C$_{1-4}$ alkylene-, and —(O—C$_{1-4}$ alkylene)$_m$-, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

L$^2$ is selected from the group consisting of —C$_{1-6}$ alkylene-, —C$_{1-6}$ alkylene-Y—, —C$_{1-4}$ alkylene-Y—C$_{1-4}$ alkylene-, or —(C$_{1-4}$ alkylene-O—)$_m$—, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

each Y is independently selected from the group consisting of O, S, S(O), S(O)$_2$, C(O), C(O)NR$^f$, NR$^f$C(O), S(O)$_2$NR$^f$, NR$^f$S(O)$_2$, and NR$^f$;

each R$^f$ is independently selected from the group consisting of H and C$_{1-3}$ alkyl;

R$^N$ is selected from the group consisting of H, C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl, wherein said C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl are each optionally substituted by 1, 2, 3, or 4 independently selected R$^g$ groups;

group A is selected from the group consisting of a 5-10 membered heteroaryl and 4-10 membered heterocycloalkyl, each of which is optionally substituted by 1, 2, 3, or 4 independently selected R$^A$ groups;

alternatively, group A is H;

with the proviso that when X is NR$^N$, L$^1$ is —C$_{1-6}$ alkylene-, L$^2$ is —C$_{1-6}$ alkylene-, and R$^N$ is C$_{1-6}$ alkyl, group A is not H;

each R$^A$ is independently selected from the group consisting of OH, NO$_2$, CN, halo, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^g$ is independently selected from the group consisting of OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and wherein the compound of Formula (IIa) comprises at least one radioisotope.

In some embodiments of a compound of Formula IIa, Hal is selected from the group consisting of Cl, F, and I. In some embodiments of a compound of Formula IIa, Hal is Cl. In some embodiments of a compound of Formula IIa, Hal is F. In some embodiments of a compound of Formula IIa, Hal is I. In some embodiments of a compound of Formula IIa, both Hal groups are Cl. In some embodiments of a compound of Formula IIa, both Hal groups are F. In some embodiments of a compound of Formula IIa, both Hal groups are I. In some embodiments of a compound of Formula IIa, one of the Hal groups is Cl and another Hal group is F. In some embodiments of a compound of Formula IIa, one of the Hal groups is Cl and another Hal group is I. In some embodiments of a compound of Formula IIa, one of the Hal groups is F and another Hal group is I. In some embodiments, Hal comprises at least one radioisotope (e.g., $^{18}$F).

In some embodiments of a compound of Formula IIa, X is selected from the group consisting of O, S, and NR$^N$. In some embodiments of a compound of Formula IIa, X is selected from the group consisting of O and NR$^N$. In some embodiments of a compound of Formula IIa, X is selected from the group consisting of O and —N(C$_{1-6}$ alkyl)-. In some embodiments of a compound of Formula IIa, X is selected from the group consisting of O and —N(CH$_3$)—. In some embodiments of a compound of Formula IIa, X is O. In some embodiments of a compound of Formula IIa, X is NR$^N$. In some embodiments of a compound of Formula IIa, —N(C$_{1-6}$ alkyl)-. In some embodiments of a compound of Formula IIa, —N(CH$_3$)—.

In some embodiments of a compound of Formula IIa, L$^1$ is selected from the group consisting of —C$_{1-6}$ alkylene-, —Y—C$_{1-6}$ alkylene-, and —C$_{1-4}$ alkylene-Y—C$_{1-4}$ alkylene-, wherein said alkylene groups are each optionally substituted with 1, 2, or 3 substituents independently selected from halo, CN, OH, C$_{1-3}$ alkoxy, amino, C$_{1-3}$ alkylamino, and di(C$_{1-3}$ alkyl)amino.

In some embodiments of a compound of Formula IIa, L$^1$ is selected from the group consisting of —C$_{1-6}$ alkylene-, and —Y—C$_{1-6}$ alkylene-, wherein said alkylene groups are each optionally substituted with 1, 2, or 3 substituents independently selected from halo, CN, OH, C$_{1-3}$ alkoxy, and amino.

In some embodiments of a compound of Formula IIa, L$^1$ is —C$_{1-6}$ alkylene-, wherein said alkylene group is optionally substituted with 1, 2, or 3 substituents independently selected from halo, CN, OH, C$_{1-3}$ alkoxy, and amino. In some embodiments of a compound of Formula IIa, L$^1$ is methylene.

In some embodiments of a compound of Formula IIa, $L^2$ is selected from the group consisting of —$C_{1-6}$ alkylene-, —$C_{1-6}$ alkylene-Y—, and —$C_{1-4}$ alkylene-Y—$C_{1-4}$ alkylene-, wherein said alkylene groups are each optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments of a compound of Formula IIa, $L^2$ is selected from the group consisting of —$C_{1-6}$ alkylene- and —$C_{1-6}$ alkylene-Y—, wherein said alkylene groups are each optionally substituted with 1, 2, or 3 substituents independently selected from halo, CN, OH, $C_{1-3}$ alkoxy, and amino.

In some embodiments of a compound of Formula IIa, $L^2$ is —$C_{1-6}$ alkylene-, wherein said alkylene group is optionally substituted with 1, 2, or 3 substituents independently selected from halo, CN, OH, $C_{1-3}$ alkoxy, and amino. In some embodiments of a compound of Formula IIa, $L^2$ is selected from the group consisting of methylene, ethylene, and butylene.

In some embodiments of a compound of Formula IIa, Y is selected from the group consisting of O, C(O), C(O)NR$^f$, NR$^f$C(O), and NR$^f$. In some embodiments of a compound of Formula IIa, Y is selected from the group consisting of O, C(O), —C(O)NH—, —NHC(O)—, NH, and —N(CH$_3$)—.

In some embodiments of a compound of Formula IIa, R$^N$ is selected from the group consisting of H, $C_{1-6}$ alkyl, $C_{2-6}$ alkenyl, $C_{2-6}$ alkynyl, $C_{1-4}$ haloalkyl. In some embodiments of a compound of Formula IIa, R$^N$ is selected from the group consisting of H and $C_{1-6}$ alkyl. In some embodiments of a compound of Formula IIa, R$^N$ is H. In some embodiments of a compound of Formula IIa, R$^N$ is $C_{1-6}$ alkyl. In some embodiments of a compound of Formula IIa, R$^N$ is $C_{1-4}$ haloalkyl. In some embodiments of a compound of Formula IIa, R$^N$ is —CH$_3$.

In some embodiments of a compound of Formula IIa, X is selected from the group consisting of O, S, S(O), S(O)$_2$, and C(O); and group A is H. In some embodiments of a compound of Formula IIa, X is selected from the group consisting of O and S; and group A is H. In some embodiments of a compound of Formula IIa, X is O; and group A is H. In some aspects of these embodiments, $L^1$ is selected from the group consisting of —$C_{1-6}$ alkylene-, and —Y—$C_{1-6}$ alkylene-, wherein said alkylene groups are each optionally substituted with 1, 2, or 3 substituents independently selected from halo, CN, OH, $C_{1-3}$ alkoxy, and amino. In some aspects of these embodiments, $L^1$ is —$C_{1-6}$ alkylene-, wherein said alkylene group is optionally substituted with 1, 2, or 3 substituents independently selected from halo, CN, OH, $C_{1-3}$ alkoxy, and amino. In some aspects of these embodiments, $L^1$ is methylene. In some aspects of these embodiments, $L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino. In some aspects of these embodiments, $L^2$ is selected from the group consisting of ethylene and butylene, each of which is optionally substituted with 1, 2, or 3 substituents independently selected from the group consisting of halo, CN, OH, $C_{1-3}$ alkoxy, amino, methylamino, and dimethylamino. In some aspects of these embodiments, $L^2$ is selected from the group consisting of ethylene and butylene, each of which is optionally substituted with 1, 2, or 3 halogen substituents independently selected from Cl, F, and I. In some aspects of these embodiments, $L^2$ is selected from the group consisting of ethylene and butylene, each of which is optionally substituted with one F. In some aspects of these embodiments, $L^2$ is fluoroethylene. In some aspects of these embodiments, $L^2$ is fluorobutylene.

In some embodiments of a compound of Formula IIa, X is NR$^N$; and group A is selected from the group consisting of a 5 or 6 membered heteroaryl and 4-10 membered heterocycloalkyl, each of which is optionally substituted by 1, 2, 3, or 4 independently selected R$^A$ groups. In some embodiments of a compound of Formula IIa, X is NR$^N$; and group A is a 5 or 6 membered heteroaryl, which is optionally substituted by 1, 2, or 3 independently selected R$^A$ groups. In some embodiments of a compound of Formula IIa, X is —N($C_{1-6}$ alkyl)-; and group A is a 5 or 6 membered heteroaryl, which is optionally substituted by 1, 2, or 3 independently selected R$^A$ groups. In some embodiments of a compound of Formula IIa, X is —N($C_{1-6}$ alkyl)-; and group A is triazolyl, which is optionally substituted by 1, 2, or 3 independently selected R$^A$ groups. In some embodiments of a compound of Formula IIa, X is —N(CH$_3$)—; and group A is triazolyl, which is optionally substituted by 1, 2, or 3 independently selected R$^A$ groups. In some embodiments of a compound of Formula IIa, X is —N(CH$_3$)—; and group A is a triazolyl of Formula A-1:

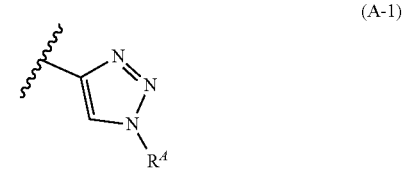

(A-1)

In some aspects of these embodiments, $L^1$ is —$C_{1-6}$ alkylene-, wherein said alkylene group is optionally substituted with 1, 2, or 3 substituents independently selected from halo, CN, OH, $C_{1-3}$ alkoxy, and amino. In some aspects of these embodiments, $L^1$ is methylene. In some aspects of these embodiments, $L^2$ is —$C_{1-6}$ alkylene-, wherein said alkylene group is optionally substituted with 1, 2, or 3 substituents independently selected from halo, CN, OH, $C_{1-3}$ alkoxy, amino, $C_{1-3}$ alkylamino, and di($C_{1-3}$ alkyl)amino. In some aspects of these embodiments, $L^2$ is methylene. In some aspects of these embodiments, R$^A$ is selected from the group consisting of OH, NO$_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino. In some aspects of these embodiments, R$^A$ is selected from the group consisting of halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino. In some aspects of these embodiments, R$^A$ is $C_{1-6}$ haloalkyl. In some aspects of these embodiments, R$^A$ is selected from the group consisting of 2-fluoroethyl, 3-fluoropropyl, and 4-fluorobutyl. In some aspects of these embodiments, R$^A$ is 2-fluoroethyl. In some aspects of these embodiments, R$^A$ is 3-fluoropropyl. In some aspects of these embodiments, R$^A$ is 4-fluorobutyl.

In some embodiments of a compound of Formula IIa, group A is H.

In some embodiments of a compound of Formula IIa, group A is selected from the group consisting of a 5 or 6 membered heteroaryl and 4-10 membered heterocycloalkyl, each of which is optionally substituted by 1, 2, 3, or 4 independently selected R$^A$ groups.

In some embodiments of a compound of Formula IIa, group A is 5 or 6 membered heteroaryl which is optionally substituted by 1, 2, 3, or 4 independently selected $R^A$ groups. In some embodiments of a compound of Formula IIa, group A is 5 membered heteroaryl which is optionally substituted by 1, 2, or 3 independently selected $R^A$ groups. In some embodiments of a compound of Formula IIa, group A is 6 membered heteroaryl which is optionally substituted by 1, 2, or 3 independently selected $R^A$ groups.

In some embodiments of a compound of Formula IIa, group A is selected from the group consisting of pyridinyl, triazinyl, pyridazinyl, pyrimidinyl, and pyrazinyl, each of which is optionally substituted by 1, 2, 3, or 4 independently selected $R^A$ groups. In some embodiments of a compound of Formula IIa, group A is selected from the group consisting of triazolyl, pyrazolyl, imidazolyl, isoxazolyl, oxazolyl, isothiazolyl, thiazolyl, furanyl, and thiophenyl, each of which is optionally substituted by 1, 2, 3, or 4 independently selected $R^A$ groups.

In some embodiments of a compound of Formula IIa, group A is triazolyl, which is optionally substituted by 1, 2, 3, or 4 independently selected $R^A$ groups. In some embodiments of a compound of Formula IIa, group A is triazolyl, which is optionally substituted by 1 $R^A$ group.

In some embodiments of a compound of Formula IIa, group A is a triazolyl of Formula A-1:

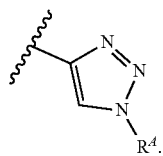

(A-1)

In some embodiments of a compound of Formula IIa, group A is 4-10 membered heterocycloalkyl, which is optionally substituted by 1, 2, 3, or 4 independently selected $R^A$ groups In some embodiments of a compound of Formula IIa, $R^A$ is $C_{1-6}$ haloalkyl. In some embodiments of a compound of Formula IIa, $R^A$ is selected from the group consisting of 2-fluoroethyl, 3-fluoropropyl, and 4-fluorobutyl. In some embodiments of a compound of Formula IIa, $R^A$ is 2-fluoroethyl. In some embodiments of a compound of Formula IIa, $R^A$ is 3-fluoropropyl. In some embodiments of a compound of Formula IIa, $R^A$ is 4-fluorobutyl.

In some embodiments, the compound of Formula IIa is a compound of Formula IIb:

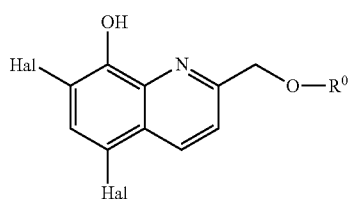

(IIb)

or a pharmaceutically acceptable salt thereof, wherein:
Hal is selected from the group consisting of Cl, F, and I; and
$R^0$ is —$C_{1-6}$ alkyl, which is optionally substituted with 1, 2, or 3 substituents independently selected from halo, CN, OH, $C_{1-3}$ alkoxy, amino, $C_{1-3}$ alkylamino, and di($C_{1-3}$ alkyl) amino;

wherein the compound of Formula (IIb) comprises at least one radioisotope.

In some embodiments of a compound of Formula IIb, Hal is Cl. In some embodiments of a compound of Formula IIb, Hal is F. In some embodiments of a compound of Formula IIb, Hal is I. In some embodiments of a compound of Formula IIb, both Hal groups are Cl. In some embodiments of a compound of Formula IIb, both Hal groups are F. In some embodiments of a compound of Formula IIb, both Hal groups are I. In some embodiments of a compound of Formula IIb, one of the Hal groups is Cl and another Hal group is F. In some embodiments of a compound of Formula IIb, one of the Hal groups is Cl and another Hal group is I. In some embodiments of a compound of Formula IIb, one of the Hal groups is F and another Hal group is I. In some embodiments, Hal comprises at least one radioisotope (e.g., $^{18}$F).

In some embodiments of a compound of Formula IIb, $R^0$ is $C_{1-6}$ haloalkyl. In some embodiments of a compound of Formula IIb, $R^0$ is $C_{1-4}$ haloalkyl.

In some embodiments of a compound of Formula IIb, $R^0$ is 2-fluoroethyl or 4-fluorobutyl. In some embodiments of a compound of Formula IIb, $R^0$ is 2-fluoroethyl. In some embodiments of a compound of Formula IIb, $R^0$ is 4-fluorobutyl.

In some embodiments of a compound of Formula IIb, one of Hal is a radioisotope.

In some embodiments of a compound of Formula IIb, Hal is selected from the group consisting of $^{18}$F, $^{75}$Br, $^{76}$Br, $^{120}$I, $^{121}$I, $^{122}$I, $^{125}$I, $^{131}$I, $^{123}$I, and $^{124}$I.

In some embodiments of a compound of Formula IIb, Hal is $^{18}$F or $^{123}$I.

In some embodiments of a compound of Formula IIb, $R^0$ comprises one radioisotope.

In some embodiments of a compound of Formula IIb, $R^0$ is selected from the group consisting of $^{18}$F, $^{75}$Br, $^{76}$Br, $^{120}$I, $^{121}$I, $^{122}$I, $^{125}$I, $^{131}$I, $^{123}$I, and $^{124}$I.

In some embodiments of a compound of Formula IIb, $R^0$ is $^{18}$F. In some embodiments of a compound of Formula IIb, $R^0$ is $^{123}$I.

In some embodiments, the compound of Formula IIa is a compound of Formula IIc:

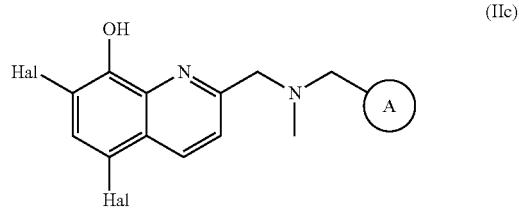

(IIc)

or a pharmaceutically acceptable salt thereof, wherein:
Hal is selected from the group consisting of Cl, F, and I;
group A is selected from the group consisting of a 5-6 membered heteroaryl and 4-10 membered heterocycloalkyl, each of which is optionally substituted by 1, 2, 3, or 4 independently selected $R^A$ groups; and
wherein the compound of Formula (IIc) comprises at least one radioisotope.

In some embodiments of a compound of Formula IIc, Hal is Cl. In some embodiments of a compound of Formula IIc, Hal is F. In some embodiments of a compound of Formula IIc, Hal is I. In some embodiments of a compound of Formula IIc, both Hal groups are Cl. In some embodiments of a compound of Formula IIc, both Hal groups are F. In some embodiments of a compound of Formula IIc, both Hal groups are I. In some embodiments of a compound of Formula IIc, one of the Hal groups is Cl and another Hal group is F. In some embodiments of a compound of Formula IIc, one of the Hal groups is Cl and another Hal group is I. In some embodiments of a compound of Formula IIc, one of the Hal groups is F and another Hal group is I.

In some embodiments of a compound of Formula IIc, group A is 5 or 6 membered heteroaryl which is optionally substituted by 1, 2, 3, or 4 independently selected $R^A$ groups. In some embodiments of a compound of Formula IIc, group A is 5 membered heteroaryl which is optionally substituted by 1, 2, or 3 independently selected $R^A$ groups. In some embodiments of a compound of Formula IIc, group A is 6 membered heteroaryl which is optionally substituted by 1, 2, or 3 independently selected $R^A$ groups.

In some embodiments of a compound of Formula IIc, group A is selected from the group consisting of pyridinyl, triazinyl, pyridazinyl, pyrimidinyl, and pyrazinyl, each of which is optionally substituted by 1, 2, 3, or 4 independently selected $R^A$ groups. In some embodiments of a compound of Formula IIc, group A is selected from the group consisting of triazolyl, pyrazolyl, imidazolyl, isoxazolyl, oxazolyl, isothiazolyl, thiazolyl, furanyl, and thiophenyl, each of which is optionally substituted by 1, 2, 3, or 4 independently selected $R^A$ groups.

In some embodiments of a compound of Formula IIc, group A is triazolyl, which is optionally substituted by 1, 2, or 3 independently selected $R^A$ groups.

In some embodiments of a compound of Formula IIc, group A is triazolyl, which is optionally substituted by 1 $R^A$ group.

In some embodiments of a compound of Formula IIc, group A is a triazolyl of Formula A-1c:

(A-1c)

In some embodiments of a compound of Formula IIc, $R^A$ is selected from the group consisting of OH, $NO_2$, CN, halo, $C_{1-6}$ alkyl, $C_{1-6}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, and di($C_{1-6}$ alkyl)amino.

In some embodiments of a compound of Formula IIc, $R^A$ is selected from the group consisting of $C_{1-6}$ alkyl, $C_{1-6}$ haloalkyl, cyano-$C_{1-3}$ alkyl, and HO—$C_{1-3}$ alkyl.

In some embodiments of a compound of Formula IIc, $R^A$ is $C_{1-6}$ haloalkyl. In some embodiments of a compound of Formula IIc, $R^A$ is selected from the group consisting of 2-fluoroethyl, 3-fluoropropyl, and 4-fluorobutyl. In some embodiments of a compound of Formula IIc, $R^A$ is 2-fluoroethyl. In some embodiments of a compound of Formula IIc, $R^A$ is 3-fluoropropyl. In some embodiments of a compound of Formula IIc, $R^A$ is 4-fluorobutyl.

In some embodiments of a compound of Formula IIc, $R^A$ comprises at least one radioisotope.

In some embodiments of a compound of Formula IIc, $R^A$ comprises one radioisotope.

In some embodiments of a compound of Formula IIc, $R^A$ comprises one or more of $^{18}F$, $^{75}Br$, $^{76}Br$, $^{120}I$, $^{121}I$, $^{122}I$, $^{125}I$, $^{131}I$, $^{123}I$, and $^{124}I$.

In some embodiments of a compound of Formula IIc, $R^A$ comprises $^{18}F$. In some embodiments of a compound of Formula IIc, $R^A$ comprises $^{123}I$.

In some embodiments, $R^N$ comprises at least one radioisotope.

In some embodiments, $R^N$ comprises one radioisotope.

In some embodiments, $R^N$ comprises $^{11}C$.

In some embodiments, $L^2$ comprises at least one radioisotope.

In some embodiments, $L^2$ comprises one radioisotope.

In some embodiments, $L^2$ comprises $^{18}F$ or $^{11}C$.

In some embodiments, $L^2$ comprises $^{18}F$.

In some embodiments, at least one of Hal groups is a radioisotope.

In some embodiments, one of Hal groups is a radioisotope.

In some embodiments, one of Hal groups is selected from the group consisting of $^{18}F$, $^{75}Br$, $^{76}Br$, $^{120}I$, $^{121}I$, $^{122}I$, $^{125}I$, $^{131}I$, $^{123}I$, and $^{124}I$.

In some embodiments, one of Hal groups is $^{18}F$ or $^{123}I$.

In some embodiments, one of Hal groups is $^{18}F$.

In some embodiments, one of Hal groups is $^{123}I$.

In some embodiments, the compound of any of Formulae II, IIa, IIb, and IIc comprises one radioisotope.

In some embodiments, the compound of Formula II, IIa, or IIb is selected from the group consisting of:

or a pharmaceutically acceptable salt thereof.

In some embodiments, the compound of Formula II, IIa, or IIc is selected from the group consisting of:

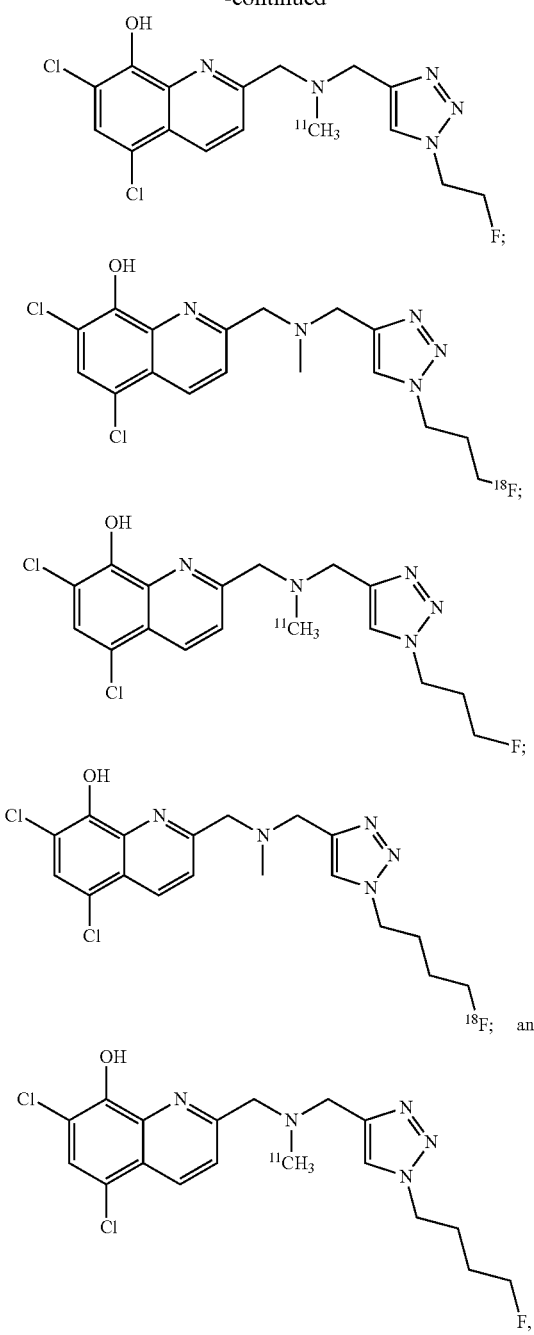

or a pharmaceutically acceptable salt thereof.
Also provided herein is a compound of Formula (III):

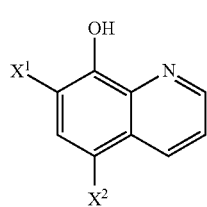

or a pharmaceutically acceptable salt thereof, wherein:
each $X^1$ and $X^2$ is independently selected from the group consisting of F, Cl, Br, and I;
wherein at least one of $X^1$ and $X^2$ comprises a radioisotope; and
wherein:
when $X^1$ is I or F, then $X^2$ is not Cl; and
when $X^1$ is I, then $X^2$ is not F.

In some embodiments, $X^1$ is F and $X^2$ is Br.
In some embodiments, $X^1$ is F and $X^2$ is I.
In some embodiments, $X^1$ is Cl and $X^2$ is F.
In some embodiments, $X^1$ is Br and $X^2$ is F.
In some embodiments, $X^1$ is F and $X^2$ is F.
In some embodiments, $X^1$ is I and $X^2$ is Br.
In some embodiments, $X^1$ is $^{18}$F and $X^2$ is Br
In some embodiments, $X^1$ is $^{18}$F and $X^2$ is I.
In some embodiments, $X^1$ is F and $X^2$ is $^{123}$I.
In some embodiments, $X^1$ is F and $X^2$ is $^{124}$I.
In some embodiments, $X^1$ is Cl and $X^2$ is $^{18}$F.
In some embodiments, $X^1$ is Br and $X^2$ is $^{18}$F.
In some embodiments, $X^1$ is $^{18}$F and $X^2$ is F.
In some embodiments, $X^1$ is F and $X^2$ is $^{18}$F.
In some embodiments, $X^1$ is $^{18}$F and $X^2$ is $^{18}$F.
In some embodiments, $X^1$ is $^{123}$I and $X^2$ is Br.
In some embodiments, $X^1$ is $^{124}$I and $X^2$ is Br.
In some embodiments, when $X^1$ is $^{123}$I or $^{18}$F, then $X^2$ is not Cl. In some embodiments, when $X^1$ is $^{123}$I, then $X^2$ is not Cl. In some embodiments, when $X^1$ is $^{18}$F, then $X^2$ is not Cl.
In some embodiments, when $X^1$ is I, then $X^2$ is not $^{18}$F.

In one embodiment, the compound of Formula III is selected from the group consisting of:

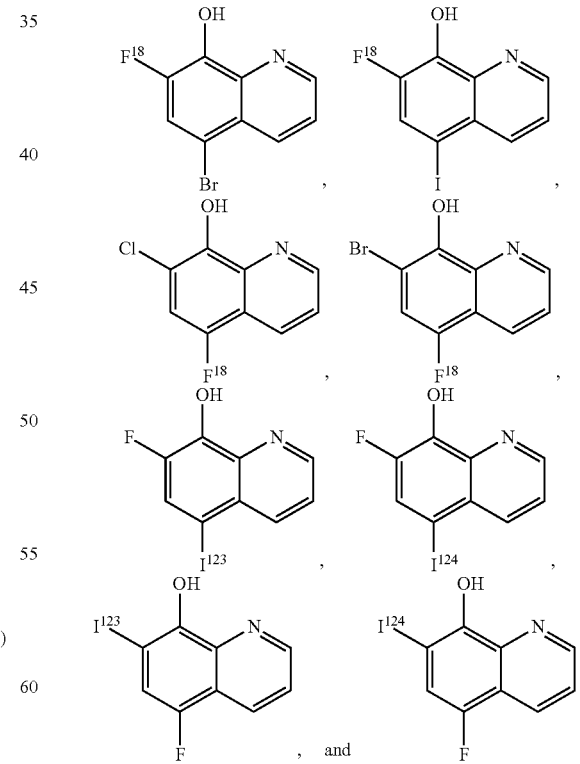

or a pharmaceutically acceptable salt thereof.
In some embodiments, compounds of Formulae II, IIa, IIb, IIc, and III can include all isotopes of atoms occurring in the intermediates or final compounds. Isotopes include those atoms having the same atomic number but different mass numbers In some embodiments, when an atom in compounds of Formulae II, IIa, IIb, IIc, and III is designated as an isotope or radioisotope (e.g., [$^{11}$C], [$^{18}$F], [$^{123}$I]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

In some embodiments, compounds of Formulae II, IIa, IIb, IIc, and III have an isotopic enrichment factor for each designated radioisotope atom of at least 3500 (52.5% radioisotope incorporation at each designated radioisotope atom), at least 4000 (60% radioisotope incorporation), at least 4500 (67.5% radioisotope incorporation), at least 5000 (75% radioisotope), at least 5500 (82.5% radioisotope incorporation), at least 6000 (90% radioisotope incorporation), at least 6333.3 (95% radioisotope incorporation), at least 6466.7 (97% radioisotope incorporation), at least 6600 (99% radioisotope incorporation), or at least 6633.3 (99.5% radioisotope incorporation).

In some embodiments, a salt of a compound of Formulae II, IIa, IIb, IIc, and III is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds Formulae II, IIa, IIb, IIc, and III include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, 3-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formulae II, IIa, IIb, IIc, and III include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formulae II, IIa, IIb, IIc, and III, or pharmaceutically acceptable salts thereof, are substantially isolated.

Pharmaceutical Compositions and Formulations

The present application also provides pharmaceutical compositions comprising an effective amount of a compound of any one of Formulae I, Ia, Ib, Ic, II, IIa, IIb, IIc, and III, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the compounds of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the present application include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, the compound any one of Formulae I, Ia, Ib, Ic, II, IIa, IIb, IIc, and III is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031.

Topical administration of the pharmaceutical compositions of the present application is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of the present application include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of the present application may also be topically applied to the lower intestinal tract by rectal suppository formulation or in a suitable enema formulation. Topically-transdermal patches and iontophoretic administration are also included in the present application.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides a method of coating an implantable medical device comprising the step of contacting said device with the coating composition described above. It will be obvious to those skilled in the art that the coating of the device will occur prior to implantation into a mammal.

According to another embodiment, the present application provides a method of impregnating an implantable drug release device comprising the step of contacting said drug release device with a compound or composition of the present application. Implantable drug release devices include, but are not limited to, biodegradable polymer capsules or bullets, non-degradable, diffusible polymer capsules and biodegradable polymer wafers.

According to another embodiment, the present application provides an implantable medical device coated with a compound or a composition comprising a compound of the present application, such that said compound is therapeutically active.

According to another embodiment, the present application provides an implantable drug release device impregnated with or containing a compound or a composition comprising a compound of the present application, such that said compound is released from said device and is therapeutically active.

Where an organ or tissue is accessible because of removal from the subject, such organ or tissue may be bathed in a medium containing a composition of the present application, a composition of the present application may be painted onto the organ, or a composition of the present application may be applied in any other convenient way.

In another embodiment, a composition of the present application further comprises a second therapeutic agent. The second therapeutic agent may be selected from any compound or therapeutic agent known to have or that demonstrates advantageous properties when administered with a compound having the same mechanism of action as a compound of any one of Formulae I, Ia, Ib, Ic, II, IIa, IIb, IIc, and III. Such agents include those indicated as being useful in combination with a compound of any one of Formulae I, Ia, Ib, Ic, II, IIa, IIb, IIc, and III, including but not limited to, an inhibitor of the acetylcholinesterase active site, for example phenserine, galantamine, or tacrine; an antioxidant, such as Vitamin E or Vitamin C; an anti-inflammatory agent such as flurbiprofen or ibuprofen optionally modified to release nitric oxide (for example NCX-2216, produced by NicOx) or an oestrogenic agent such as 17-β-oestradiol.

In some embodiments, a compound of any one of Formulae I, Ia, Ib, Ic, II, IIa, IIb, IIc, and III can be used in combination with a chemotherapeutic agent, surgical cancer treatment, or radiotherapy. In some embodiments, chemotherapeutic agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine. In some embodiments, chemotherapeutic agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethio¬phosphoramine, busulfan, carmustine, lomustine, streptozocin, dacarbazine, and temozolomide In another embodiment, the present application provides separate dosage forms of a compound of any one of Formulae I, Ia, Ib, Ic, II, IIa, IIb, IIc, and III and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the present application, a compound of any one of Formulae I, Ia, Ib, Ic, II, IIa, IIb, IIc, and III is present in an effective amount (e.g., a therapeutically effective amount).

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In some embodiments, an effective amount of a compound of any one of Formulae I, Ia, Ib, Ic, II, IIa, IIb, IIc, and III can range, for example, from about 10 mg to about 2000 mg, from about 10 mg to about 1900 mg, from about 10 mg to about 1800 mg, from about 10 mg to about 1700 mg, from about 10 mg to about 1600 mg, from about 10 mg to about 1500 mg, from about 10 mg to about 1400 mg, from about 10 mg to about 1300 mg, from about 10 mg to about 1200 mg, from about 10 mg to about 1100 mg, from about 10 mg to about 1000 mg, from 10 mg about to about 900 mg, from about 10 mg to about 800 mg, from about 10 mg to about 700 mg, from about 10 mg to about 600 mg, from about 10 mg to about 500 mg, from about 10 mg to about 400 mg, from about 10 mg to about 300 mg, from about 10 mg to about 200 mg, from about 10 mg to about 100 mg, and from about 10 mg to about 50 mg. In some aspects of these embodiments, the composition containing an effective amount of a compound of any one of Formulae I, Ia, Ib, Ic, II, IIa, IIb, IIc, and III is administered once daily. In some aspects of these embodiments, the composition containing an effective amount of a compound of any one of Formulae I, Ia, Ib, Ic, II, IIa, IIb, IIc, and III is administered twice daily. In some aspects of these embodiments, the composition containing an effective amount of a compound of any one of Formulae I, Ia, Ib, Ic, II, IIa, IIb, IIc, and III is administered thrice daily.

In some embodiments, an effective amount of a compound of any one of Formulae I, Ia, Ib, Ic, II, IIa, IIb, IIc, and III can range, for example, from about 1 mg/kg to about 500 mg/kg, from about 1 mg/kg to about 200 mg/kg, from about 1 mg/kg to about 100 mg/kg, from about 1 mg/kg to about 50 mg/kg, from about 1 mg/kg to about 40 mg/kg, from about 1 mg/kg to about 30 mg/kg, from about 1 mg/kg to about 20 mg/kg, from about 1 mg/kg to about 10 mg/kg, from about 2 mg/kg to about 400 mg/kg, from about 3 mg/kg to about 300 mg/kg, from about 4 mg/kg to about 200 mg/kg, from about 5 mg/kg to about 100 mg/kg, from about 10 mg/kg to about 500 mg/kg, from about 10 mg/kg to about 400 mg/kg, from about 10 mg/kg to about 300 mg/kg, from about 10 mg/kg to about 200 mg/kg, from about 10 mg/kg to about 100 mg/kg, and from about 10 mg/kg to about 50 mg/kg. In some aspects of these embodiments, the composition containing an effective amount of a compound of any one of Formulae I, Ia, Ib, Ic, II, IIa, IIb, IIc, and III is administered once daily. In some aspects of these embodiments, the composition containing an effective amount of a compound of any one of Formulae I, Ia, Ib, Ic, II, IIa, IIb, IIc, and III is administered twice daily. In some aspects of these embodiments, the composition containing an effective amount of a compound of any one of Formulae I, Ia, Ib, Ic, II, IIa, IIb, IIc, and III is administered thrice daily.

In some embodiments, an effective amount of a compound of any one of Formulae I, Ia, Ib, Ic, II, IIa, IIb, IIc, and III can be, for example, 1 mg/kg, 5 mg/kg, 10 mg/kg, 20 mg/kg, 30 mg/kg, 40 mg/kg, 50 mg/kg, or 100 mg/kg. In some aspects of these embodiments, the composition containing an effective amount of a compound of any one of Formulae I, Ia, Ib, Ic, II, IIa, IIb, IIc, and III is administered once daily. In some aspects of these embodiments, the composition containing an effective amount of a compound of any one of Formulae I, Ia, Ib, Ic, II, IIa, IIb, IIc, and III is administered twice daily. In some aspects of these embodiments, the composition containing an effective amount of a compound of any one of Formulae I, Ia, Ib, Ic, II, IIa, IIb, IIc, and III is administered thrice daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for Compound 1.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of the present application. When this occurs, it will allow the effective dosage of the second therapeutic agent and/or the compound of the present application to be reduced from that required in a monotherapy. This has the advantage of minimizing toxic side effects of either the second therapeutic agent of a compound of the present application, synergistic improvements in efficacy, improved ease of administration or use and/or reduced overall expense of compound preparation or formulation.

Synthesis

Compounds provided herein, including salts thereof, can be prepared using known organic synthesis techniques and can be synthesized according to any of numerous possible synthetic routes.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

The compounds of Formula I provided herein can be prepared according to Scheme 1. For example, 8-hydorxyquinoline derivative 1-1 can be first protected with a Boc group, followed by an oxidation reaction, such as $SeO_2$ oxidation, and subsequent deprotection, to yield aldehyde 1-2. When X is O, the subsequent reduction with a reducing reagent, such as $NABH_4$, can lead to oxygen-containing intermediate 1-3. When X is $NR^N$, reacting aldehyde 1-2 with a substituted amine $HNR^N$ leads to the intermediate Shiff-base, which as further reduced in-situ by using a reducing agent, such as $NaBH_4$, to yield a nitrogen-containing intermediate 2-3. The following reaction, such as alkylation reaction, with an intermediate 1-4 using an appropriate leaving group (LG) leads to the compounds of Formula I.

Scheme1

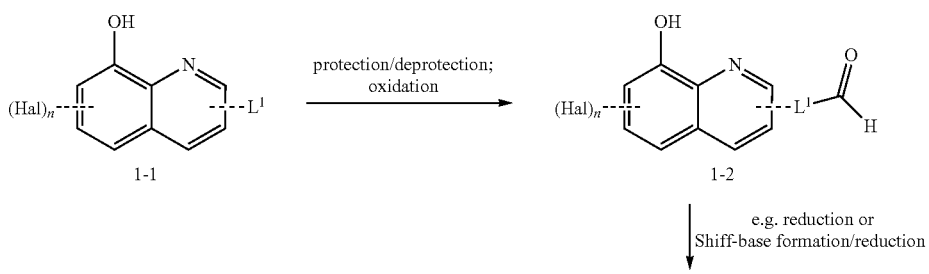

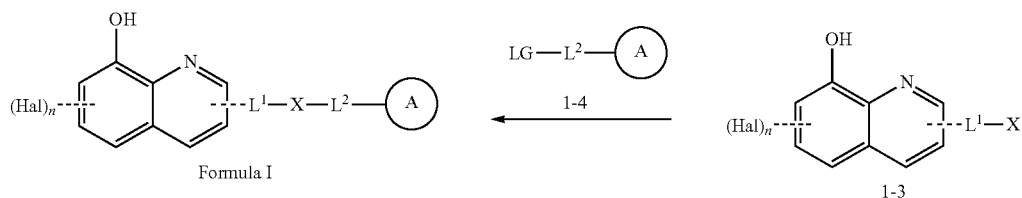

The compounds of Formula Ia can be prepared according to Scheme 2. For example, 8-hydorxyquinoline derivative 2-1 can be first protected with a Boc group, followed by an oxidation reaction, such as SeO$_2$ oxidation, and subsequent deprotection, to yield aldehyde 2-2. When X is O, the subsequent reduction with a reducing reagent, such as NABH$_4$, can lead to oxygen-containing intermediate 2-3. When X is NR$^N$, reacting aldehyde 2-2 with a substituted amine HNR$^N$ leads to the intermediate Shiff-base, which is further reduced in-situ by using a reducing agent, such as NaBH$_4$, to yield a nitrogen-containing intermediate 2-3. The following reaction, such as an alkylation reaction, with an intermediate 1-4 using an appropriate leaving group (LG) leads to the compounds of Formula Ia.

Scheme 2

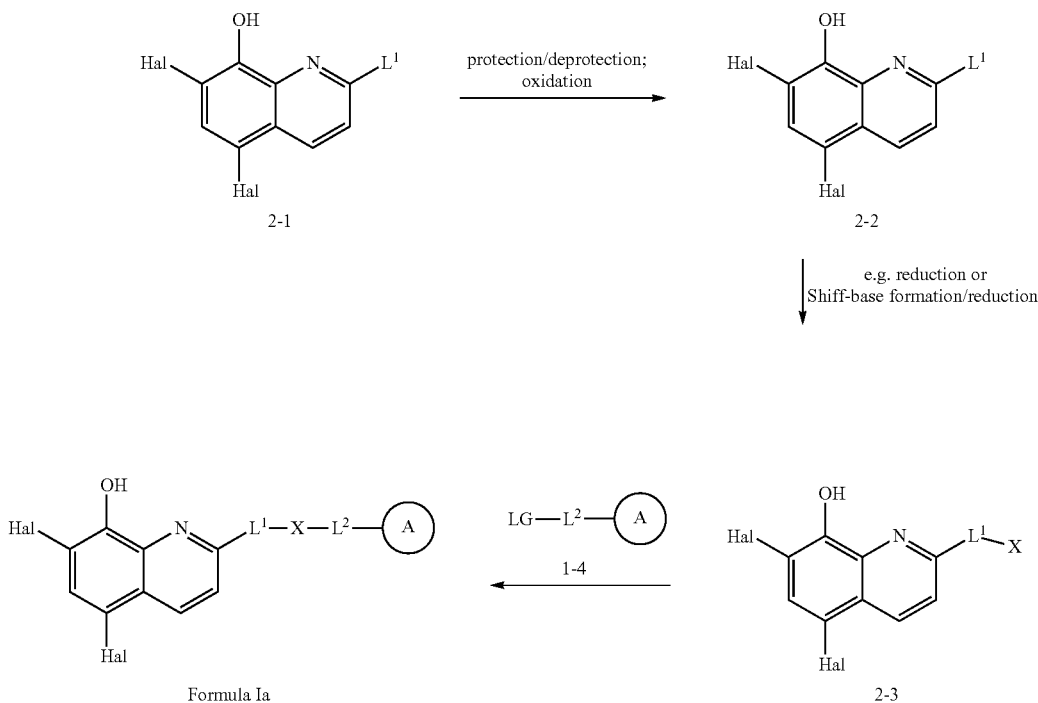

The compounds of Formula Ib can be prepared according to Scheme 3. For example, 8-hydorxyquinoline derivative 3-1 can be first protected with a Boc group, followed by an oxidation reaction, such as $SeO_2$ oxidation, and subsequent deprotection, to yield aldehyde 3-2. Aldehyde 3-2 can be further reduced by using, for example, $NaBH_4$. Subsequent alkylation reaction of 3-3 with LG-$R^0$ alkylating reagent 3-4, wherein LG is an appropriate leaving group such as tosylate, leads to compounds of Formula Ib.

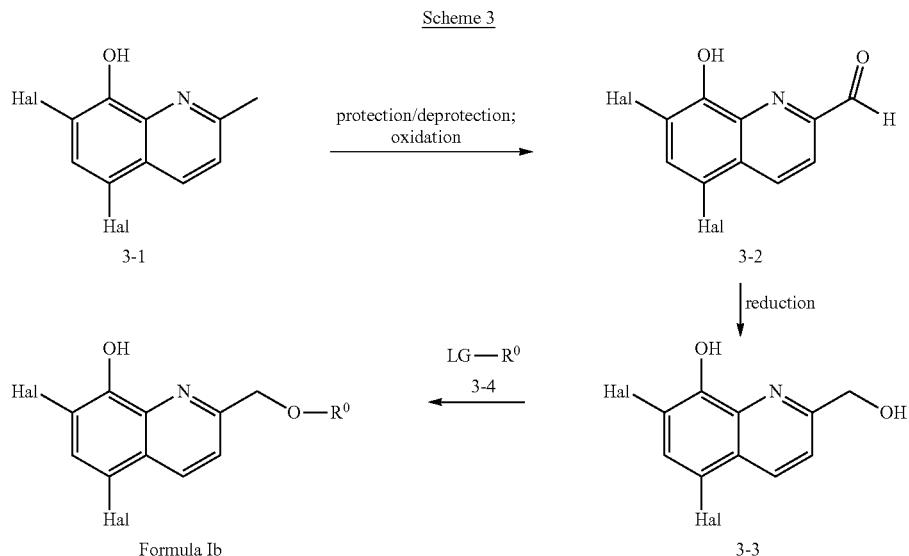

Scheme 3

The fluorinated ethers 3a-1 can be prepared from alcohols 3-3 using alkylating reagents such as fluoroalkyl tosylate, in the presence of a base such as NaH, according to Scheme 3a. The hydroxyl group of 3-3 can be protected prior to the alkylation step and deprotected after the alkylation step. The suitable protecting group is, for example, a BOC-protecting group.

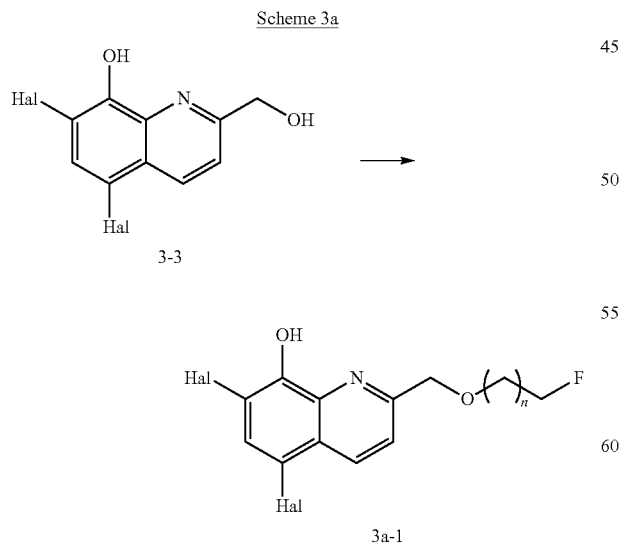

Scheme 3a n = 0-5

The compounds of Formula Ic can be prepared according to Scheme 4. For example, aldehyde 3-2 can react with an amide such as methylamine to yield the intermediate Shiff-base 4-1. Subsequent reduction of the Shiff-base 4-1 with a reducing agent such as $NaBH_4$ produces secondary amine 4-2. Alkylating the secondary amine 4-2 with an alkylating agent 4-3, wherein LG is a suitable leaving group such as halide (e.g., bromide) and RG1 is a reactive group such as alkyne, leads to a reactive intermediate 4-4. Reacting 4-4 with group 4-5, wherein RG2 is a reactive group such as azide, yields the compounds of Formula Ic.

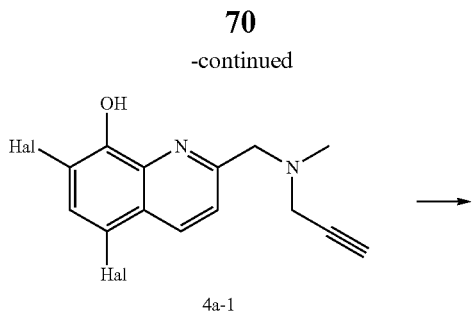

4a-1

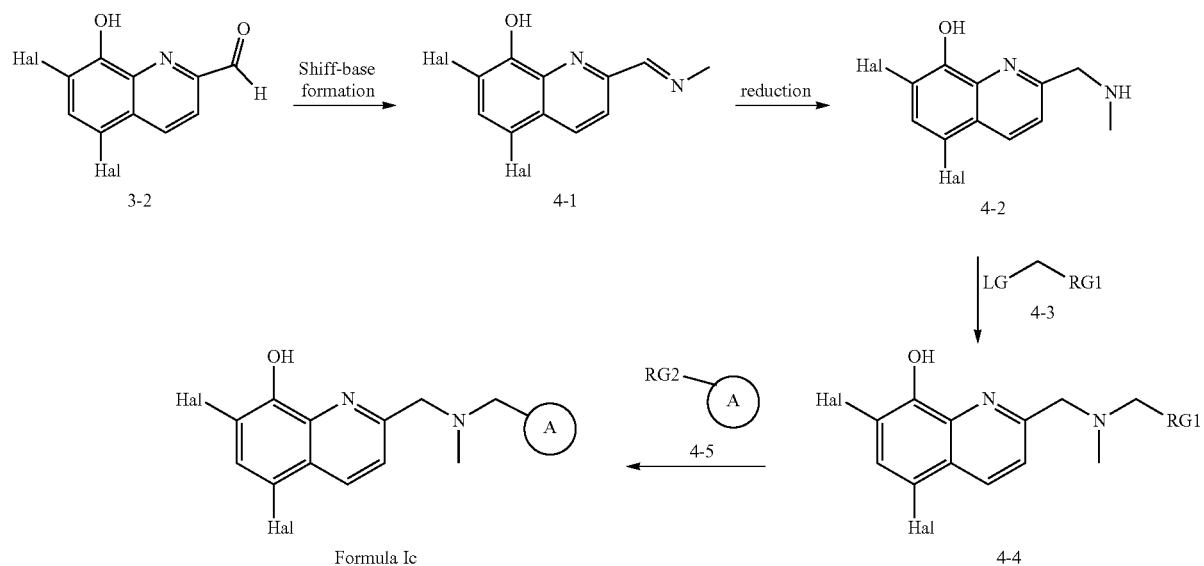

Scheme 4

Formula Ic

Triazole compounds 4a-2 can be prepared according to Scheme 4a. For example, secondary amine 4-2 can react with haloalkyne such as 3-bromopropyne, in the presence of a tertiary amine such as DIPEA, to arrive at the alkyne derivatives 4a-1. The alkynes 4a-1 can subsequently react with fluoroalkyl azide, such as fluoroethyl azide, in the presence of a suitable catalyst, such as $CuSO_4 \times 5H_2O$ and sodium ascorbate, to arrive at compounds 4a-2.

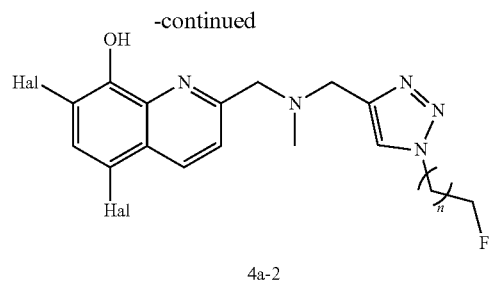

4a-2 n = 0-5

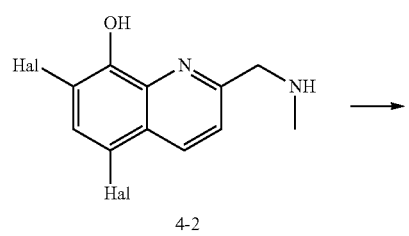

Scheme 4a 4-2

Compounds of Formulae II, IIa, IIb, and IIc can be prepared from starting materials containing at least one radioisotope according to the methods and procedures described for the compounds of Formulae I, Ia, Ib, and Ic. Synthetic methods for incorporating radioisotopes into organic compounds are well known in the art, and one of ordinary skill in the art will readily recognize the methods applicable for the compounds of Formulae II, IIa, IIb, and IIc.

In one embodiment, radiolabeling of compounds of any one the Formulae II, IIa, IIb, and IIc can be carried out using the procedures analogous to those outlined in Scheme 5.

Scheme 5

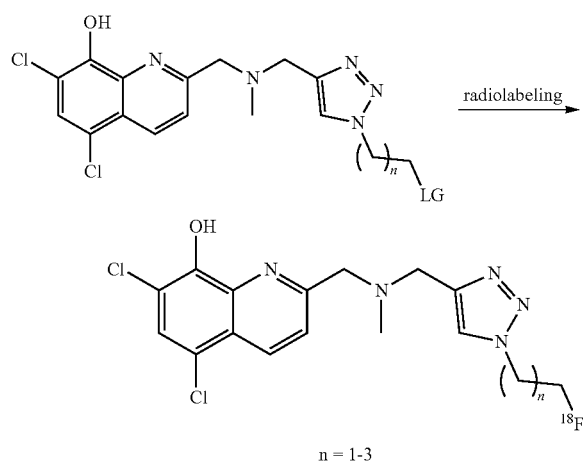

n = 1-3 wherein LG is a suitable leaving group, and the radiolabeling reagent contains $^{18}$F.

In one embodiment, radiolabeling of compounds of any one the Formulae II, IIa, IIb, and IIc can be carried out using the procedures analogous to those outlined in Scheme 6.

Scheme 6

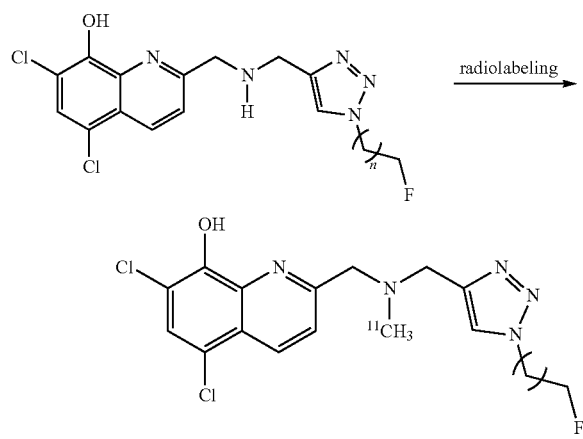

wherein the radiolabeling can be conducted using $^{11}$C-enriched methyl halide, such as methyl iodide.

In one embodiment, radiolabeling of compounds of any one the Formulae II, IIa, IIb, and IIc can be carried out using the procedures analogous to those outlined in Scheme 7.

Scheme 7

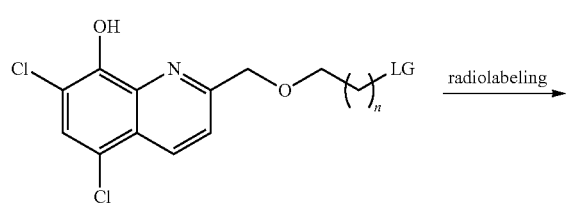

wherein LG is a suitable leaving group, and the radiolabeling reagent contains $^{18}$F.

Compounds of Formula III can be prepared from starting materials containing at least one radioisotope. Synthetic methods for incorporating radioisotopes into organic compounds are well known in the art, and one of ordinary skill in the art will readily recognize the methods applicable for the synthesis of compounds of Formula III.

In one embodiment, radiolabeling of compounds of Formula III can be carried out using the procedures analogous to those outlined in Scheme 8.

Scheme 8

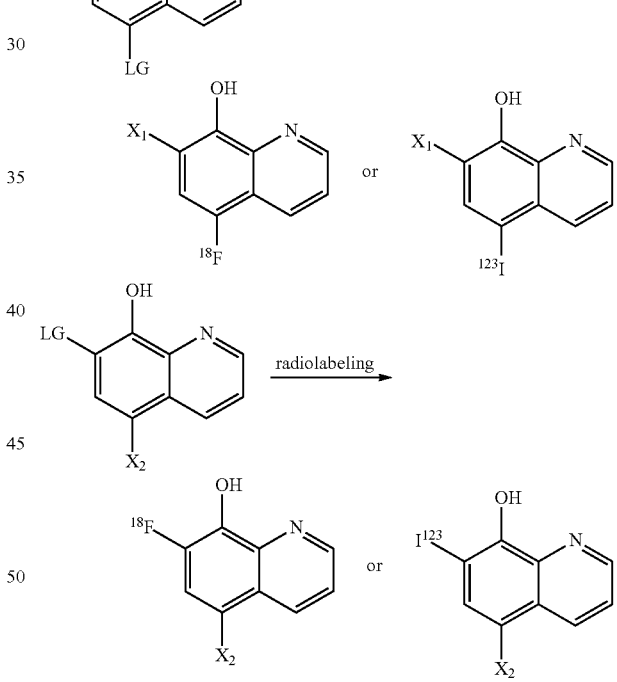

wherein LG is a suitable leaving group, and the radiolabeling reagent contains $^{18}$F or $^{123}$I.

Methods of Use

Methods of Treatment:

Provided in the present application are methods of treating a disease or disorder in a subject in need thereof. In some embodiments, the method comprises administering to the subject a therapeutically effective amount of a compound provided herein (e.g., a compound of Formula I, Ia, Ib, or Ic), or a pharmaceutically acceptable salt thereof.

In some embodiments, the present application provides a method of treating a neurological disorder in a subject in need thereof, the method comprising administering to the subject a therapeutically effective amount of a compound of any one of Formulae I, Ia, Ib, and Ic, or a pharmaceutically acceptable salt thereof.

In some embodiments, the neurological disorder is a neurodegenerative disease.

In some embodiments, the neurodegenerative disease is selected from the group consisting of Alzheimer's disease (AD), Parkinson's disease (PD), Huntington's Disease (HD), motor neurone disease (MND), and Prion disease.

In some embodiments, the neurodegenerative disease is Alzheimer's disease (AD).

In some embodiments, the neurological disorder is selected from the group consisting of cerebral amyloid angiopathy, vascular cognitive impairment (VCI), dementia, dementia with Lewy bodies, frontotemporal dementia (FTD), amyotrophic lateral sclerosis (ALS), multiple sclerosis, hippocampal sclerosis, Binswanger's disease, and Creutzfeldt-Jakob disease.

In some embodiments, the neurological disorder is selected from the group consisting of AIDS dementia and HIV-1 induced neurotoxicity; Alzheimer's disease; amylotrophic lateral sclerosis, cerebral ischaemia, cerebrovascular ischemia, brain ischemia, cerebral palsy; cerebral tumour; chemotherapy-induced brain damage; cisplatin-induced neurotoxicity, Creutzfeldt-Jacob disease and its new variant associated with "mad cow" disease; diabetic neuropathy; Down's syndrome; drowning; epilepsy and post-traumatic epilepsy; Friedreich's ataxia; frontotemporal dementia; Hallervorden-Spatz disease; Huntington's disease; Lewy body disease; stroke, ischaemic stroke; mascular degeneration; methanol-induced neurotoxicity; meningitis (aseptic and tuberculous); motor neuron disease; multiple sclerosis; multiple system atrophy; neoplasia; Parkinson's disease; perinatal asphyxia; Pick's disease; progressive supranuclear palsy; radiotherapy-induced brain damage; senile dementia; schizophrenia; depression, major depressive disorder, subharrachnoid haemorrage/cerebral vasospasm; surgical trauma, including neurosurgery; neurosurgical trauma, transient ischaemic attack (TIA); traumatic brain injury (TBI); traumatic spinal injury; vascular dementia; viral meningitis; encephalitis, and viral encephalitis.

In some embodiments, the present application provides a method of treating cancer in a subject in need thereof, the method comprising administering to the subject a therapeutically effective amount of a compound of any one of Formulae I, Ia, Ib, and Ic, or a pharmaceutically acceptable salt thereof.

In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, the cancer is prostate cancer.

In some embodiments, cancer is selected from the group selected from sarcoma, angiosarcoma, fibrosarcoma, rhabdomyosarcoma, liposarcoma, myxoma, rhabdomyoma, fibroma, lipoma, teratoma, lung cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

Methods of Diagnosis, Imaging, and Monitoring Treatment.

Provided in the present application are methods of imaging the brain of a subject in need of such imaging. In some embodiments, the method comprises administering to the subject an effective amount of a compound of any one of Formulae II, IIA, IIb, IIc, and III, or a pharmaceutically acceptable salt thereof. In further embodiments, the method comprises waiting a time sufficient to allow the compound to accumulate in the brain to be imaged. In yet further embodiments, the method comprises imaging the brain with an imaging technique.

Provided in the present application are methods of diagnosing a neurological disorder in a subject in need of such diagnosis. In some embodiments, the method comprises administering to the subject an effective amount of a compound of any one of Formulae II, IIa, IIb, IIc, and III, or a pharmaceutically acceptable salt thereof. In further embodiments, the method comprises waiting a time sufficient to allow the compound to accumulate at a tissue or cell site associated with the neurological disorder. In yet further embodiments, the method comprises imaging the cell or tissue with an imaging technique.

Provided in the present application are methods of monitoring treatment of a neurological disorder in a subject in need of such monitoring. In some embodiments, the method comprises imaging a cell or tissue with an imaging technique. In further embodiments, the method comprises administering to the subject an effective amount of a compound of any one of Formulae II, IIa, IIb, IIc, and III, or a pharmaceutically acceptable salt thereof. In further embodiments, the method comprises waiting a time sufficient to allow the compound to accumulate at a tissue or cell site associated with the neurological disorder. In further embodiments, the method comprises imaging the cell or tissue with an imaging technique after administration of a compound of any one of Formulae II, IIa, IIb, IIc, and III to the subject and waiting the time sufficient to allow the compound to accumulate at a tissue or cell site associated with the neurological disorder. In yet further embodiments, the method comprises comparing the image obtained before administration of a compound of any one of Formulae II, IIa, IIb, IIc, and III with the image obtained after administration of the compound.

In some embodiments, the present application provides a method of imaging the brain of a subject, the method comprising:
  i) administering to the subject an effective amount of a compound of any one of Formulae II, IIa, IIb, IIc, and III, or a pharmaceutically acceptable salt thereof;
  ii) waiting a time sufficient to allow the compound to accumulate in the brain to be imaged; and
  iii) imaging the brain with an imaging technique.

In some embodiments, the present application provides a method of diagnosing a neurological disorder in a subject, the method comprising:
  i) administering to the subject a compound of any one of Formulae II, IIa, IIb, IIc, and III;
  ii) waiting a time sufficient to allow the compound to accumulate at a tissue or cell site associated with the neurological disorder;
  iii) imaging the cell or tissue with an imaging technique;

In some embodiments, the method further comprises determining the diagnosis of the neurological disorder in the subject. In some embodiments, the method further comprises providing the diagnosis of the neurological disorder to the subject.

In some embodiments, the present application provides a method of monitoring treatment of a neurological disorder in a subject, the method comprising:
  i) imaging a cell or tissue with an imaging technique;
  ii) administering to the subject a compound of any one of Formulae II, IIa, IIb, IIc, and III in an effective amount of to treat the neurological disorder;
  iii) waiting a time sufficient to allow the compound to accumulate at a tissue or cell site associated with the neurological disorder;
  iv) imaging the cell or tissue with an imaging technique; and
  v) comparing the image of step i) and the image of step iv).

In some embodiments, the method further comprises determining progression or regression of a neurological disorder in a subject. In some embodiments, the method further comprises providing results of determination to the subject.

In some embodiments, the neurological disorder is a neurodegenerative disease.

In some embodiments, neurodegenerative disease is selected from any one of the neurodegenerative diseases described herein.

In some embodiments, neurodegenerative disease is Alzheimer's disease (AD).

In some embodiments, neurological disorder is selected from any one of the neurological disorders described herein.

Provided in the present application are methods of diagnosing cancer in a subject in need of such diagnosis. In some embodiments, the method comprises administering to the subject an effective amount of a compound of any one of Formulae II, IIa, IIb, IIc, and III, or a pharmaceutically acceptable salt thereof. In further embodiments, the method comprises waiting a time sufficient to allow the compound to accumulate at a tissue or cell site associated with cancer. In yet further embodiments, the method comprises imaging the cell or tissue with an imaging technique.

Provided in the present application are methods of monitoring treatment of cancer in a subject in need of such monitoring. In some embodiments, the method comprises imaging a cell or tissue with an imaging technique. In further embodiments, the method comprises administering to the subject an effective amount of a compound of any one of Formulae II, IIa, IIb, IIc, and III, or a pharmaceutically acceptable salt thereof. In further embodiments, the method comprises waiting a time sufficient to allow the compound to accumulate at a tissue or cell site associated with the cancer. In further embodiments, the method comprises imaging the cell or tissue with an imaging technique after administration of the compound of any one of Formulae II, IIa, IIb, IIc, and III to the subject and waiting the time sufficient to allow the compound to accumulate at a tissue or cell site associated with cancer. In yet further embodiments, the method comprises comparing the image obtained before administration of a compound of any one of Formulae II, IIa, IIb, IIc, and III with the image obtained after administration of the compound.

In some embodiments, the present application provides a method of diagnosing cancer in a subject, the method comprising:
  i) administering to the subject a compound of any one of Formulae II, IIa, IIb, IIc, and III;
  ii) waiting a time sufficient to allow the compound to accumulate at a tissue or cell site associated with the cancer; and
  iii) imaging the cell or tissue with an imaging technique.

In some embodiments, the method further comprises determining the diagnosis of the cancer in the subject. In some embodiments, the method further comprises providing the diagnosis of cancer to the subject.

In some embodiments, the present application provides a method of monitoring treatment of a cancer in a subject, the method comprising:
  i) imaging a cell or tissue with an imaging technique;
  ii) administering to the subject a compound of any one of Formulae II, IIa, IIb, IIc, and III in an effective amount of to treat the cancer;
  iii) waiting a time sufficient to allow the compound to accumulate at a tissue or cell site associated with the cancer;
  iv) imaging the cell or tissue with an imaging technique; and v) comparing the image of step i) and the image of step iv).

In some embodiments, the method further comprises determining progression or regression of cancer in a subject. In some embodiments, the method further comprises providing results of determination to the subject.

In some embodiments, the cancer is selected from any one of the cancers described herein.

In some embodiments, the imaging technique is selected from the group consisting of magnetic resonance imaging, optical imaging, single-photon emission computer tomography, positron emission tomography imaging, positron emission tomography with computer tomography imaging, and positron emission tomography with magnetic resonance imaging.

In some embodiments, the imaging technique is selected from the group consisting of positron emission tomography (PET) and single-photon emission computer tomography (SPECT).

In some embodiments, the imaging technique is positron emission tomography (PET).

In some embodiments, the imaging technique is single-photon emission computer tomography (SPECT).

In some embodiments, any determination of results of imaging, diagnosis, or monitoring of treatment is performed by a skilled physician, according to the relevant circumstances, including the condition to be treated, the chosen route of administration, the actual compound administered, the age, weight, and response of the individual subject, the severity of the subject's symptoms, and the like.

Definitions

At various places in the present specification, substituents of compounds of the present application are disclosed in groups or in ranges. It is specifically intended that various embodiments of the present application include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "halo" refers to F, Cl, Br, or I. In some embodiments, a halo is F, Cl, or Br. In other embodiments, halo is F, Cl, or I. In other embodiments, halo is F, I, or Br.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di $C_{n-m}$ alkylamino" refers to a group of formula —$N(alkyl)_2$, wherein each alkyl group independently has n to m carbon atoms. In some embodiments, each alkyl group has 1 to 6, 1 to 4, or 1 to 3 carbon atoms. Examples of dialkylamino groups include, but are not limited to, N,N-methylehtylamino, N,N-diethylamino, N,N-propylethylamino, N,N-butylisopropylamino, and the like.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di $C_{n-m}$ alkylcarbamyl" refers to a group of formula —C(O)—N(alkyl)$_2$, wherein each alkyl group independently has n to m carbon atoms. In some embodiments, the alkyl group has 1 to 6, 1 to 4, or 1 to 3 carbon atoms.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano" refers to a group of formula —CN.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cyclocalkyl. In some embodiments, the cycloalkyl is a $C_{3-7}$ monocyclic cyclocalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membereted heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., a triazole ring, etc.). Unless otherwise indicated, these rings can be attached to any ring member provided that the valency of the atom is not exceeded. For example, a triazole ring may be attached at any position of the ring, whereas a triazol-1-yl ring is attached at the 1-position.

As used herein, the term "oxo" refers to an oxygen atom as a divalent substituent, forming a carbonyl group when attached to a carbon (e.g., C=O), or attached to a heteroatom forming a sulfoxide or sulfone group.

As used herein, the term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

As used herein, the term "tautomer" refers to compounds which are capable of existing in a state of equilibrium between two isomeric forms. Such compounds may differ in the bond connecting two atoms or groups and the position of these atoms or groups in the compound.

As used herein, the term "isomer" refers to structural, geometric and stereo isomers. As the compound of the present application may have one or more chiral centers, it is capable of existing in enantiomeric forms.

As used herein, the term "substantially isolated" refers to the compound that is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "ionophore" refers to a molecule that transports ions across a cell membrane. In some embodiments, ionophore is a carrier ionophore (i.e., binds to a particular ion to shield its charge from the surrounding environment and transports an ion through the lipid bilayer of a cell membrane).

As used herein, the term "metal chelator" refers to compounds having two or more donor atoms capable of binding to a metal atom, preferably Cu, Zn or Fe wherein at least two of the donor atoms are capable of simultaneous binding to the metal atom and the resultant metal complex has a thermodynamic stability greater than or equal to that of the metal ion: biological ligand complex.

As used herein, the term "pharmaceutical carrier", or "pharmaceutically acceptable carrier" refers to a pharmaceutically acceptable solvent, suspending agent or vehicle for delivering the compound of the present application to the subject. The carrier may be liquid or solid and is selected with the planned manner of administration in mind. Each carrier must be pharmaceutically "acceptable" in the sense of being compatible with other ingredients of the composition and non injurious to the subject.

As used herein, the term "radioisotope" refers to an atom having an atomic mass or mass number different from the atomic mass or mass number typically found in nature (i.e., naturally occurring).

As used herein, the term "isotopically" or "radio-labeled" compound refers to a compound where one or more atoms are replaced or substituted by an atom having an atomic mass or mass number different from the atomic mass or mass number typically found in nature (i.e., naturally occurring). Example radioisotopes include, but are not limited to, $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{67}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{99m}Tc$, $^{110m}In$, $^{111}In$, $^{118}Sb$, $^{120}I$, $^{121}I$, $^{122}I$, $^{123}I$, $^{124}I$, $^{124}I$, $^{131}I$, and $^{201}Tl$.

As used herein, the term "isotopic enrichment factor" refers to the ratio between the isotopic abundance and the natural abundance of a specified isotope.

EXAMPLES

Experimental procedures for compounds of the present application are provided below.

As depicted in the Examples below, compounds are prepared according to the following general procedures. It will be appreciated that, although the general methods depict the synthesis of certain compounds provided herein, the following general methods, and other methods known to one of ordinary skill in the art, can be applied to all compounds and subclasses and species of each of these compounds, as described herein.

Analytical Methods.

Nuclear magnetic resonance (NMR) spectra were recorded using a Bruker Avance DPX-400 spectrometer operating at 400 MHz for $^1H$ NMR and at 101 MHz for $^{13}C$ NMR. Low-resolution mass spectrometry (LRMS) was performed on a Micromass ZQ quadrupole mass spectrometer, and high-resolution mass spectrometry (HRMS) was performed at the University of Wollongong, Australia using a Bruker Daltonics BioApex-II 7T FTICR spectrometer equipped with an off-axis analytical electron spray ionisation source. Flash chromatography was performed on a Reveleris® Flash Chromatography System (Grace Davison Discovery Sciences, Rowville, Australia), fitted with an ELSD (isopropanol support) and dual-wavelength UV (254 and 280 nm) detectors; solvent systems are described where appropriate. HPLC purity analysis was performed using a Waters Empower 2 system with a Waters 600 pump, Waters in-line degasser AF, Waters temperature control module II, Waters 717 autosampler and Water 2996 PDA. Either an Alltech Alltima C18 (150×4.6 mm, 5 μm pore size) or Waters XTerraRP (150×4.6 mm, 5 μm pore size) analytical column was used, with absorbance measured at 254 nm. Samples were prepared as 1 mg/mL, with a 10 μL injection. Solvent conditions were as follows:

| Entry | Time | Flow (mL/min) | % A (MeCN or MeOH) | % B ($H_2O$) | % C (100 mM $NH_4HCO_3$ pH 8 or 1% TFA) |
|---|---|---|---|---|---|
| 1 | 0 | 1.00 | 10 | 80 | 10 |
| 2 | 20 | 1.00 | 90 | 0 | 10 |
| 3 | 21 | 1.00 | 10 | 80 | 10 |

Percentage purity was calculated from the peak area under using Empower software (Waters).

Materials.

5-Fluoro-8-hydroxyquinoline was purchased from Fluorochem. 7-Fluoro-8-hydroxyquinoline was purchased from CHEMOS. N-Chlorosuccinimide, N-Bromosuccinimide, N Iodosuccinimide, aluminum trichloride and trifluoroacetic acid were purchased from Sigma Aldrich. Deuterated solvents were purchased from Cambridge Isotope Laboratories (Novachem, Collingwood, Australia). All commercial materials were used as received. Unless otherwise stated all solvents used were HPLC grade or were dried using the MBraun MB SPS-800 solvent purification system.

Examples 1-9 (Compounds 2-10)

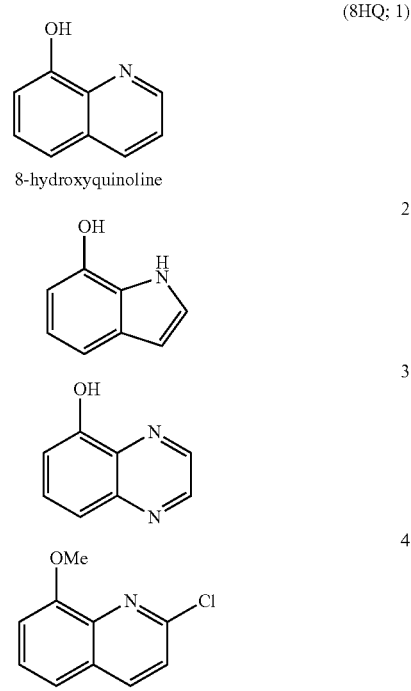

-continued

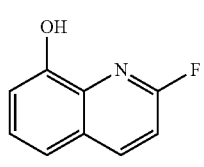
CABS13
(5)

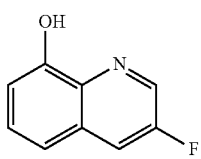
(6)

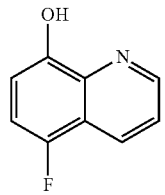
(7)

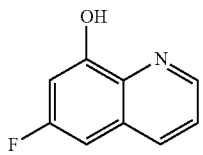
(8)

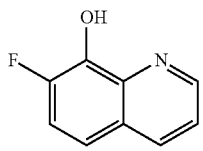
(9)

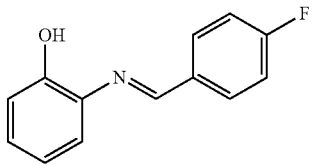
(10)

Examples 1-9 can be readily prepared according to numerous methods and procedures available to one of ordinary skill in the art. Such methods and procedures can be found, for example, in Smith et al., March's Advanced Organic Chemistry: Reactions, Mechanisms, and Structure, 6th Ed. (Wiley, 2007). Suitable starting materials and intermediates are readily available from various commercial sources.

Example 10 (Compound 12)

5-chloro-7-fluoro-8-hydroxyquinoline

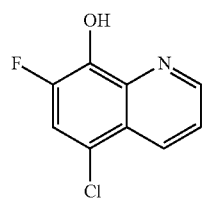 [SMILES: Oc1c(F)cc(Cl)c2cccnc12]

N-Chlorosuccinimide (120 mg, 0.90 mmol) was added to a solution of 7-fluoro-8-hydroxyquinoline (120 mg, 0.74 mmol) in DCM (5 mL). The reaction mixture was stirred and heated to 40° C. for 5 h and then cooled to rt for 2 days. The reaction was then diluted with DCM (50 ml) and washed with 15% sodium thiosulfate solution (3×10 mL). The organic layer was dried ($Na_2SO_4$) and solvent evaporated to give a brown solid. Chromatography of the residue (0→20% EtOAc/hexanes gradient) gave 52 mg of the title product. Yield: 36%. White solid. $^1$H NMR (400 MHz, $CDCl_3$): δ 8.86 (dd, J=1.2, 4.2 Hz, 1H), 8.51 (dd, J=1.6, 8.9 Hz, 1H), 7.54 (dd, J=4.4, 8.9 Hz, 1H), 7.51 (d, J=10.5 Hz, 1H) ppm. $^{13}$C NMR (400 MHz, $CDCl_3$): δ 149.50, 146.6 (d, J=246.5 Hz), 139.6 (d, J=7.9 Hz), 137.7 (d, J=10.4 Hz), 133.5 (d, J=2.3 Hz), 123.3, 121.8 (d, J=3.1 Hz), 120.5 (d, J=10.1 Hz), 118.7 (d, J=24.5 Hz) ppm. LRMS (ESI) calcd. for $C_9H_6ClFNO$ [M+H]$^+$ 198.01, found 198.10. HRMS (ESI) calcd. $C_9H_6ClFNO$ [M+H]$^+$ 198.0122, found 198.0120. HPLC purity (MeCN/$H_2O$/0.1% TFA): 99.8%, 7.5 min; HPLC purity (MeOH/$H_2O$/0.1% TFA): 99.6%, 10.4 min.

Example 11 (Compound 13)

5-bromo-7-fluoro-8-hydroxyquinoline

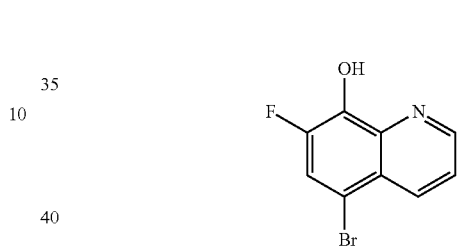

N-Bromosuccinimide (130 mg, 0.73 mmol) was added to a solution of 7-fluoro-8-hydroxyquinoline (98 mg, 0.60 mmol) in chloroform (5 mL). The reaction mixture was stirred and heated to 40° C. overnight and then diluted with DCM (50 ml) and washed with 15% sodium thiosulfate solution (3×10 mL). The organic layer was dried ($Na_2SO_4$) and solvent evaporated to give a brown solid. Chromatography of the residue (0→25% EtOAc/hexanes gradient) gave 60 mg of the title product. Yield: 41%. Pale yellow solid. $^1$H NMR (400 MHz, $CDCl_3$): δ 8.83 (dd, J=1.3, 4.3 Hz, 1H), 8.46 (dd, J=1.5, 8.6 Hz, 1H), 7.71 (d, J=10.3 Hz, 1H), 7.54 (dd, J=4.3, 8.6 Hz, 1H) ppm. $^{13}$C NMR (101 MHz, $CDCl_3$): δ 149.3, 146.7 (d, J=248.0 Hz), 139.7 (d, J=7.6 Hz), 138.2 (d, J=10.5 Hz), 135.9 (d, J=2.0 Hz), 124.4, 122.1, 121.9 (d, J=20.1 Hz), 109.3 (d, J=9.8 Hz) ppm. LRMS (ESI) cacld. $C_9H_6BrFNO$ [M+H]$^+$ 241.96, found 242.10. HRMS (ESI) $C_9H_6BrFNO$ calcd. [M+H]$^+$ 241.9617, found 241.9615. HPLC purity (MeCN/$H_2O$/0.1% TFA): 97.9%, 9.9 min; HPLC purity (MeOH/$H_2O$/0.1% TFA): 98.6%, 17.8 min.

Example 12 (Compound 14)

7-fluoro-5-iodo-8-hydroxyquinoline

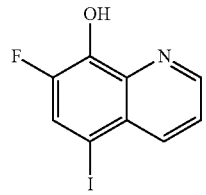

N-iodosuccinimide (166 mg, 0.74 mmol) was added to a solution of 7-fluoro-8-hydroxyquinoline (100 mg, 0.61 mmol) in chloroform (10 mL). The reaction mixture was stirred and heated to reflux overnight and then diluted with DCM (50 ml) and washed with 15% sodium thiosulfate solution (3×10 mL). The organic layer was dried ($Na_2SO_4$) and solvent evaporated to give a brown solid. Chromatography of the residue (0→20% EtOAc/hexanes gradient) gave 93 mg of the title product. Yield: 53%. Pale yellow solid. $^1$H NMR (400 MHz, $CDCl_3$): δ 8.77 (dd, J=1.3, 4.2 Hz, 1H), 8.30 (dd, J=1.4, 8.6 Hz, 1H), 7.95 (d, J=10.1 Hz, 1H), 7.51 (dd, J=4.2, 8.6 Hz, 1H) ppm. $^{13}$C NMR (101 MHz, $CDCl_3$): δ 149.2, 147.2 (d, J=246.6 Hz), 145.9, 140.4 (d, J=2.0 Hz), 139.5 (d, J=7.4 Hz), 139.1 (d, J=10.2 Hz), 128.7 (d, J=23.9 Hz), 126.9 (d, J=1.4 Hz), 122.5 (d, J=2.5 Hz), 82.7 (d, J=8.8 Hz) ppm. LRMS (ESI) cacld. $C_9H_6FINO$ [M+H]$^+$289.95, found 289.58. HRMS (ESI) cacld. $C_9H_6FINO$ [M+H]$^+$ 289.9478, found 289.9476. HPLC purity (MeCN/$H_2O$/0.1% TFA): 96.8%, 8.8 min; HPLC purity (MeOH/$H_2O$/0.1% TFA): 96.5%, 12.1 min.

Example 13 (Compound 15)

7-chloro-5-fluoro-8-hydroxyquinoline

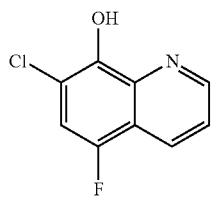

N-Chlorosuccinimide (440 mg, 3.1 mmol) and aluminum trichloride (35 mg, 0.26 mmol) was added to a solution of 5-fluoro-8-hydroxyquinoline (424 mg, 2.6 mmol) in DCM (10 mL). The reaction mixture was stirred and heated to reflux overnight and then diluted with DCM (50 ml) and washed with 15% sodium thiosulfate solution (3×10 mL). The organic layer was dried ($Na_2SO_4$) and solvent evaporated to give a brown solid. Chromatography of the residue (0→20% EtOAc/hexanes gradient) gave 122 mg of the title product. Yield: 24%. Light brown solid. $^1$H NMR (400 MHz, $CDCl_3$): δ 8.86 (dd, J=1.4, 4.2 Hz, 1H), 8.39 (dd, J=5.0, 8.4 Hz, 1H), 7.52 (dd, J=5.0, 8.4 Hz, 1H), 7.23 (d, J=9.7 Hz, 1H) ppm. $^{13}$C NMR (101 MHz, $CDCl_3$): δ 150.2 (d, J=249.3 Hz), 149.8, 145.1 (d, J=4.4 Hz), 137.9 (d, J=4.4 Hz), 130.2 (d, J=2.3 Hz), 122.0 (d, J=2.8 Hz), 118.0 (d, J=19.1 Hz), 114.4 (d, J=10.9 Hz), 112.8 (d, J=23.0 Hz) ppm. LRMS calcd. for $C_9H_6ClFNO$ [M+H]$^+$ 198.01, found 197.83. HRMS (ESI) calcd. for $C_9H_6ClFNO$ [M+H]$^+$ 198.0122, found 198.0120. HPLC purity (MeCN/$H_2O$/0.1% TFA): 98.5%, 9.8 min; HPLC purity (MeOH/$H_2O$/0.1% TFA): 99.4%, 12.4 min.

Example 14 (Compound 16)

7-bromo-5-fluoro-8-hydroxyquinoline

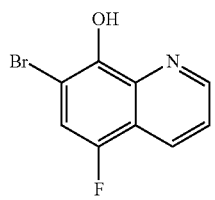 [SMILES: Oc1c(Cl)cc(F)c2cccnc12]

N-Bromosuccinimide (1.26 g, 7.1 mmol) was added to a solution of 5-fluoro-8-hydroxyquinoline (970 mg, 5.9 mmol) in chloroform (50 mL). The reaction mixture was stirred and heated to 40° C. overnight and then diluted with DCM (100 ml) and washed with 15% sodium thiosulfate solution (3×20 mL). The organic layer was dried ($Na_2SO_4$) and solvent evaporated to give a brown solid. Chromatography of the residue (0→25% EtOAc/hexanes gradient) gave 426 mg of the title product. Yield: 30%. White solid. $^1$H NMR (400 MHz, $CDCl_3$): δ 8.85 (dd, J=1.3, 4.2 Hz, 1H), 8.38 (dd, J=1.5, 8.4 Hz, 1H), 7.54 (dd, J=4.3, 8.4 Hz, 1H), 7.37 (d, J=9.4 Hz, 1H) ppm. $^{13}$C NMR 101 MHz, $CDCl_3$): δ 150.2 (d, J=251.8 Hz), 149.6, 146.4 (d, J=4.4 Hz), 137.6 (d, J=3.9 Hz), 130.2 (d, J=2.9 Hz), 122.0 (d, J=2.3 Hz), 118.3 (d, J=19.0 Hz), 101.9 (d, J=10.3 Hz) ppm. LRMS (ESI) calcd. for $C_9H_6BrFNO$ [M+H]$^+$ 241.96, found 241.72. HRMS (ESI) calcd. for $C_9H_6BrFNO$ [M+H]$^+$ 241.9617, found 241.9621. HPLC purity (MeCN/$H_2O$/0.1% TFA): 96.5%, 11.6 min; HPLC purity (MeOH/$H_2O$/0.1% TFA): 96.6%, 14.7 min.

Example 15 (Compound 17)

5-fluoro-7-iodo-8-hydroxyquinoline

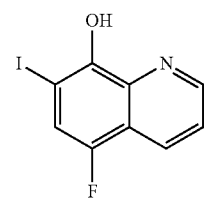 [SMILES: Oc1c(I)cc(F)c2cccnc12]

N-iodosuccinimide (166 mg, 0.74 mmol) was added to a solution of 5-fluoro-8-hydroxyquinoline (100 mg, 0.61 mmol) in chloroform (5 mL). The reaction mixture was stirred and heated to 50° C. overnight and then diluted with DCM (50 ml) and washed with 15% sodium thiosulfate solution (3×10 mL). The organic layer was dried ($Na_2SO_4$) and solvent evaporated to give a brown solid. Chromatography of the residue (0→20% EtOAc/hexanes gradient) gave 85 mg of the title product. Yield: 48%. Off white needles. $^1$H NMR (400 MHz, $CDCl_3$): δ 8.82 (dd, J=1.7, 4.4 Hz, 1H), 8.37 (dd, J=8.4, 1.6 Hz, 1H), 7.54 (dd, J=8.4, 4.3 Hz, 1H), 7.51 (d, J=9.3 Hz, 1H) ppm. $^{13}$C NMR (101 MHz, CDCl$_3$): δ 150.2 (d, J=251.2 Hz), 149.6 (d, J=3.8 Hz), 149.4, 136.5 (d, J=3.7 Hz), 130.3 (d, J=2.9 Hz), 122.2 (d, J=2.2 Hz), 119.6 (d, J=23.0 Hz), 118.9 (d, J=18.7 Hz), 73.7 (d, J=9.0 Hz) ppm. LRMS (ESI) calcd. for C$_9$H$_6$FlNO [M+H]$^+$ 289.95, found 289.66. HRMS (ESI) calcd. for C$_9$H$_6$FlNO [M+H]$^+$ 289.9478, found 289.9486. HPLC purity (MeCN/H$_2$O/0.1% TFA): 95.9%, 13.8 min; HPLC purity (MeOH/H$_2$O/0.1% TFA): 96.1%, 17.0 min.

Example 16 (Compound 23)

5,7-dichloro-2-((2-fluoroethoxy)methyl)quinolin-8-ol

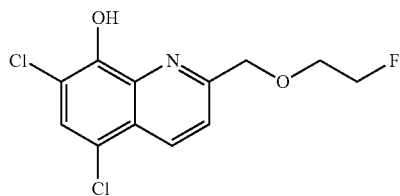 [SMILES: Oc1c(Cl)cc(Cl)c2ccc(COCCF)nc12]

Step 1. tert-butyl (5,7-dichloro-2-methylquinolin-8-yl) carbonate

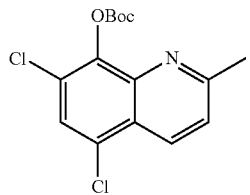

A mixture of 5,7-dichloro-2-methylquinolin-8-ol (10.0 g, 43.8 mmol), Boc$_2$O (19.1 g, 2.0 equiv.), Et$_3$N (9.14 mL, 1.5 equiv.) and DMAP (107 mg, 0.02 equiv.) in THF (50 mL) was heated with stirring to 80° C. for 12 h under Argon. The mixture was then cooled to room temperature, and concentrated in vacuo. The crude was washed with water to yield the desired product (13.0 g, 39.6 mmol) as a white solid in 90% yield and used in the subsequent step without further purification.

Step 2. tert-butyl (5,7-dichloro-2-formylquinoline-8-yl) carbonate

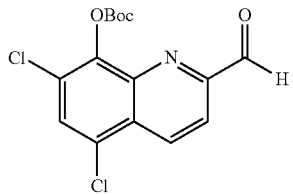

A mixture of tert-butyl (5,7-dichloro-2-methylquinolin-8-yl) carbonate (12 g, 36.6 mmol), SeO$_2$ (8.1 g, 2.0 equiv.) in 1,4-dioxane (30 mL) was heated with stirring to 80° C. for 12 h. The progress of the reaction was monitored by NMR (SeO$_2$ was needed to be filtered off from NMR sample). When the reaction was complete, the mixture was filtered over a prepacked short column (1 inch silica and 1 inch celite) by reduced pressure using 500 mL DCM. It was known that tert-butyl (5,7-dichloro-2-formylquinolin-8-yl) carbonate was not stable on prolonged silica contact. The filtrate was concentrated and dried over high-vac to get yellow solid and used in the next step without further purification.

Step 3. 5,7-dichloro-2-(hydroxymethyl)quinolin-8-ol

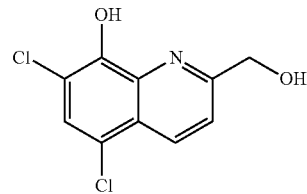 [SMILES: OCc1ccc2c(Cl)cc(Cl)c(O)c2n1]

A mixture of tert-butyl (5,7-dichloro-2-formylquinolin-8-yl) carbonate (1.0 g, 2.9 mmol), NaBH$_4$ (332 mg, 3 equiv.) in ethanol (30 mL) was reacted at r.t. for 12 h. Saturated solution of ammonium chloride (15 mL) was added to quench the reaction. Water (50 mL) was then added and the mixture was extracted with DCM (3×30 mL). The combined extracts were washed with brine, dried with sodium sulfate, and purified by flash column chromatography (20% EtOAc in Hexanes) on silica to afforded a white solid, which was then dissolved in the mixture of DCM (10 mL) and TFA (2.5 mL), stirred for 2 h until reaction was complete. Saturate NaHCO$_3$ solution (20 mL) was then added slowly until the precipitate formed. The precipitate was filtered, washed with water and dried to yield the desired product (570 mg, 80%) as a white solid and this product was used in the next step without further purification.

Step 4. 5,7-dichloro-2-((2-fluoroethoxy)methyl)quinolin-8-ol

A mixture of 5,7-dichloro-2-(hydroxymethyl)quinolin-8-ol (200 mg, 819 μmol) and NaH (131 mg, 4.0 equiv.) in DMF (3 mL) was stirred at r.t. for 30 min. Then the fluoroethyl tosylate (1.0 equiv.) in DMF (2 mL) solution was added slowly into the mixture and the resultant mixture was stirred for another 3 h. The progress of the reaction was monitored by TLC. When the reaction was complete, saturated solution of ammonium chloride (5 mL) was added to quench the unreacted NaH. Water (20 mL) was then added and the mixture was extracted with DCM (3×10 mL). The combined extracts were washed with brine, dried with sodium sulfate, and purified by flash column chromatography (EtOAc) on silica to afford 5,7-dichloro-2-((2-fluoroethoxy)methyl)quinolin-8-ol (38 mg, 16%) as a white solid. $^1$H NMR (400 MHz, DMSO-d$_6$) δ 8.53 (d, J=8.7 Hz, 1H), 7.81 (d, J=11.1 Hz, 2H), 4.88 (s, 2H), 4.71-4.67 (m, 1H), 4.59-4.55 (m, 1H), 3.91-3.85 (m, 1H), 3.82-3.76 (m, 1H); $^{13}$C NMR (101 MHz, DMSO-d$_6$) δ 158.92, 148.74, 138.19, 133.70, 127.49, 124.06, 121.22, 119.13, 115.86, 83.82, 82.18, 73.12, 69.93, 69.74.

Example 17 (Compound 24)

5,7-dichloro-2-((4-fluorobutoxy)methyl)quinolin-8-ol

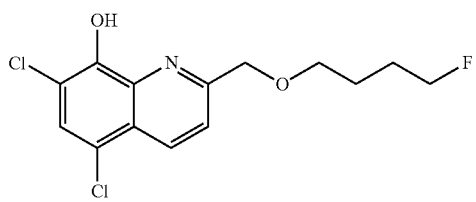 [SMILES: Oc1c(Cl)cc(Cl)c2ccc(COCCCCF)nc12]

The title compound was prepared using procedures analogous to those described for Example 23 using fluorobutyl tosylate to replace fluoroethyl tosylate in Step 4 as white solid (45 mg, 18%). $^1$H NMR (400 MHz, DMSO-$d_6$) δ 8.53 (d, J=8.7 Hz, 1H), 7.79 (s, 1H), 7.48 (d, J=7.9 Hz, 1H), 4.80 (s, 2H), 3.68 (t, J=6.5 Hz, 2H), 3.59 (t, J=6.2 Hz, 3H), 1.83 (d, J=7.3 Hz, 2H), 1.76-1.69 (m, 2H); $^{13}$C NMR (101 MHz, DMSO-$d_6$) δ 148.71, 138.17, 133.63, 128.05, 127.41, 125.48, 121.18, 119.12, 115.80, 72.96, 69.70, 45.28, 44.61, 29.42, 29.04, 26.59.

Example 18 (Compound 28)

5,7-dichloro-2-((((1-(2-fluoroethyl)-1H-1,2,3-triazol-4-yl)methyl)(methyl)amino)methyl)quinolin-8-ol

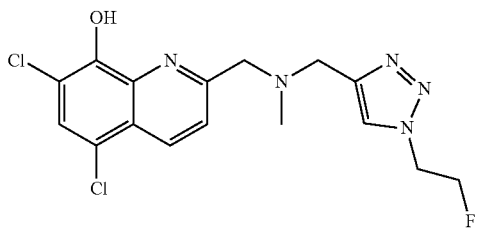 [SMILES: CN(Cc1cn(CCF)nn1)Cc1ccc2c(Cl)cc(Cl)c(O)c2n1]

Step 1. (E)-5,7-dichloro-2-((methylimino)methyl)quinolin-8-ol

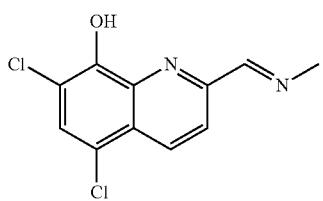 [SMILES: C/N=C/c1ccc2c(Cl)cc(Cl)c(O)c2n1]

To a tert-butyl (5,7-dichloro-2-formylquinolin-8-yl) carbonate (Prepared in Example 23; Step 2; 2.0 g, 5.8 mmol) solution in THF (100 mL), the methylamine gas was bubbled slowly for 2 h until the precipitate formed. The formed precipitate was filtered, washed with THF and dried to yield the desired product (1.5 g, 5.8 mmol) as a white yellow solid in 99% yield which was used in the next step without further purification.

Step 2. 5,7-dichloro-2-((methylamino)methyl)quinolin-8-ol

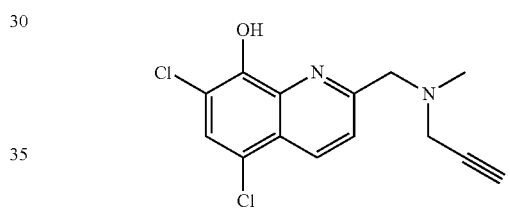

A mixture of (E)-5,7-dichloro-2-((methylimino)methyl)quinolin-8-ol (1.5 g, 5.8 mmol), NaBH$_4$ (1.1 g, 5 equiv.) in ethanol (50 mL) was reacted at r.t. for 12 h. When the reaction was complete, the mixture was adjusted the pH to 3 with 0.1 N HCl, and then adjusted the pH to 7 with saturated ammonia water until the precipitate formed. The precipitate was filtered, washed with water and dried to yield the desired product (870 mg, 3.4 mmol) as a gray solid in 58% yield which was used in the next step without further purification.

Step 3. 5,7-dichloro-2-((methyl(prop-2-yn-1-yl)amino)methyl)quinolin-8-ol

To the mixture DMF (25 mL) solution of 5,7-dichloro-2-((methylamino)methyl)quinolin-8-ol (2.0 g, 7.8 mmol) and DIPEA (2.6 mL, 2 equiv.), the 3-bromopropyne (1.7 mL, 2 equiv.) in DMF (5 mL) was added slowly via syringe at 50° C. The mixture was stirred at 50° C. for another 5 min until the reaction was complete. Water (100 mL) was then added and the mixture was extracted with DCM (3×100 mL). The combined extracts were washed with brine, dried with sodium sulfate, and purified by rapid filtration over silica pad and recrystallization to afford the desired product (759 mg, 33%) as a gray solid which was used in the next step without further purification.

Step 4. 5,7-dichloro-2-((((1-(2-fluoroethyl)-1H-1,2,3-triazol-4-yl)methyl)(methyl)amino)methyl)quinolin-8-ol A mixture of 5,7-dichloro-2-((methyl(prop-2-yn-1-yl)amino)methyl)quinolin-8-ol (147 mg, 0.5 mmol), CuSO$_4$.5H$_2$O (13 mg, 0.1 equiv.), sodium ascorbate (20 mg, 0.2 equiv.), and fluoroethyl azide (2 equiv.) in THF-H$_2$O (9:1, 2 mL) was stirred at r.t. for 30 min. Water (5 mL) was then added and the mixture was extracted with DCM (3×3 mL). The combined extracts were washed with brine, dried with sodium sulfate, and purified by flash column chromatography (DCM-MeOH 15:1) on silica to afforded the desired product (86 mg, 45%) as a gray solid. $^1$H NMR (400 MHz, DMSO-$d_6$) δ 10.91 (s, 1H), 8.56 (d, J=8.1 Hz, 1H), 8.37 (s, 1H), 7.88 (s, 1H), 7.72 (d, J=7.4 Hz, 1H), 4.82 (d, J=30.8 Hz, 2H), 4.61 (s, 2H), 4.41 (d, J=5.9 Hz, 2H), 3.32 (d, J=6.0 Hz, 1H), 2.93 (s, 3H), 1.97 (s, 1H); $^{13}$C NMR (101 MHz, DMSO-$d_6$) δ 151.49, 148.49, 137.20, 136.20, 134.56, 127.85, 124.18, 122.20, 119.16, 115.89, 57.79, 49.86, 47.72, 46.97, 28.89.

Example 19 (Compound 29)

5,7-dichloro-2-((((1-(3-fluoropropyl)-1H-1,2,3-triazol-4-yl)methyl)(methyl)amino)methyl)quinolin-8-ol

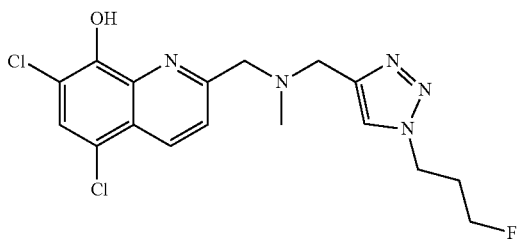 [SMILES: CN(Cc1cn(CCCF)nn1)Cc1ccc2c(Cl)cc(Cl)c(O)c2n1]

The title compound was prepared using procedures analogous to those described for Example 28 using fluoropropyl azide to replace fluoroethyl azide in Step 4 as gray solid (97 mg, 49%). $^1$H NMR (400 MHz, DMSO-$d_6$) δ 10.95 (s, 1H), 8.63 (d, J=8.7 Hz, 1H), 8.42 (s, 1H), 7.95 (s, 1H), 7.79 (d, J=8.7 Hz, 1H), 4.89 (d, J=31.4 Hz, 2H), 4.67 (s, 2H), 4.49 (t, J=6.9 Hz, 2H), 3.38 (s, 2H), 3.00 (s, 3H), 2.04 (s, 2H); $^{13}$C NMR (101 MHz, DMSO-$d_6$) δ 151.48, 148.95, 137.38, 136.18, 134.40, 128.20, 127.63, 124.05, 122.09, 119.04, 115.88, 57.70, 49.82, 47.73, 46.96, 41.00, 40.88.

Example 20 (Compound 30)

5,7-dichloro-2-((((1-(4-fluorobutyl)-1H-1,2,3-triazol-4-yl)methyl)(methyl)amino)methyl)quinolin-8-ol

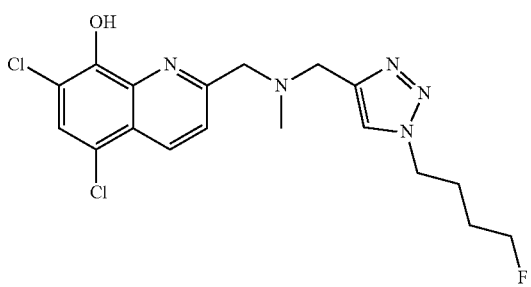 [SMILES: CN(Cc1cn(CCCCF)nn1)Cc1ccc2c(Cl)cc(Cl)c(O)c2n1]

The title compound was prepared using procedures analogous to those described for Example 28 using fluorobutyl azide to replace fluoroethyl azide in Step 4 as gray solid (80 mg, 39%). $^1$H NMR (400 MHz, DMSO-$d_6$) δ 10.86 (s, 1H), 8.57 (d, J=8.8 Hz, 1H), 8.35 (d, J=8.9 Hz, 1H), 7.88 (d, J=17.4 Hz, 1H), 7.76-7.68 (m, 1H), 4.82 (d, J=29.6 Hz, 2H), 4.62 (s, 2H), 4.39 (t, J=6.8 Hz, 2H), 3.28 (s, 3H), 2.94 (d, J=8.8 Hz, 3H), 1.76 (dd, J=15.4, 7.7 Hz, 2H), 1.50-1.38 (m, 1H); $^{13}$C NMR (101 MHz, DMSO-$d_6$) δ 148.84, 141.64, 137.41, 134.39, 128.28, 127.37, 124.03, 121.95, 119.03, 116.92, 115.83, 57.81, 49.96, 49.00, 26.88, 25.19.

Example A: Ionophore Activity of Synthesized Compounds

Ionophore Assay:

SH-SY5Y cells (American Type Culture Collection, CRL-2266), were cultured in DMEM containing Glutamax (Invitrogen) supplemented with 1 mM sodium pyruvate (Sigma) and 10% fetal calf serum (Sigma). Cells were maintained at 37° C. with 5% $CO_2$ and passaged every 3-4 days. Compounds (10 mM) were solubilized in DMSO (Sigma). CQ and PBT2 were used as positive controls. Cells were treated with growth media supplemented with each compound (20 μM) or vehicle for 6 hours. Cells were harvested and metal levels were measured with Inductively-Coupled Plasma Mass Spectrometry (Varian), as previously described. (See, e.g., Cherny, R. A. et al., (2001) Treatment with a copper-zinc chelator markedly and rapidly inhibits beta-amyloid accumulation in Alzheimer's disease transgenic mice, Neuron 30, 665) K was used as an internal standard and Cu, Zn and Fe levels expressed relative to vehicle treated control cells. Data represents the mean and S.E.M. of at least 9 replicates from 3 experiments. A oneway ANVOA with Fisher's LSD test was used to determine statistical differences relative to control (Prism 6, Graphpad).

FIG. 1 describes ionophore assay of 8HQ derivatives (8HQ and compounds 2-10). Dashed line indicates control level. SH-SY5Y cells treated were treated with each compound (20 μM) for 6 hours and cellular metal levels were measured with ICP-MS.

Figure 2:
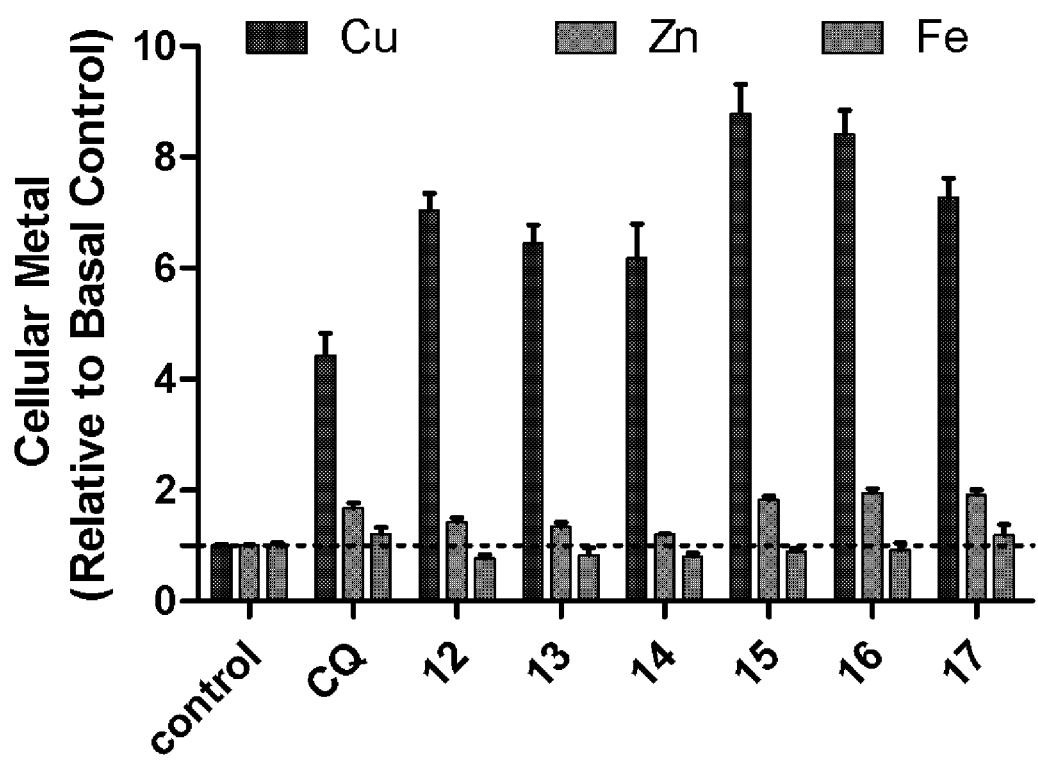
FIG. 2 shows an ionophore activity of 8HQ derivatives: Compounds 12-17.

FIG. 2 describes ionophore activity of CQ derivatives (CQ and compounds 12-17). SH-SY5Y cells treated were treated with each compound (20 μM) for 6 hours and cellular metal levels were measured with ICP-MS. Dashed line indicates control level.

Figure 3:
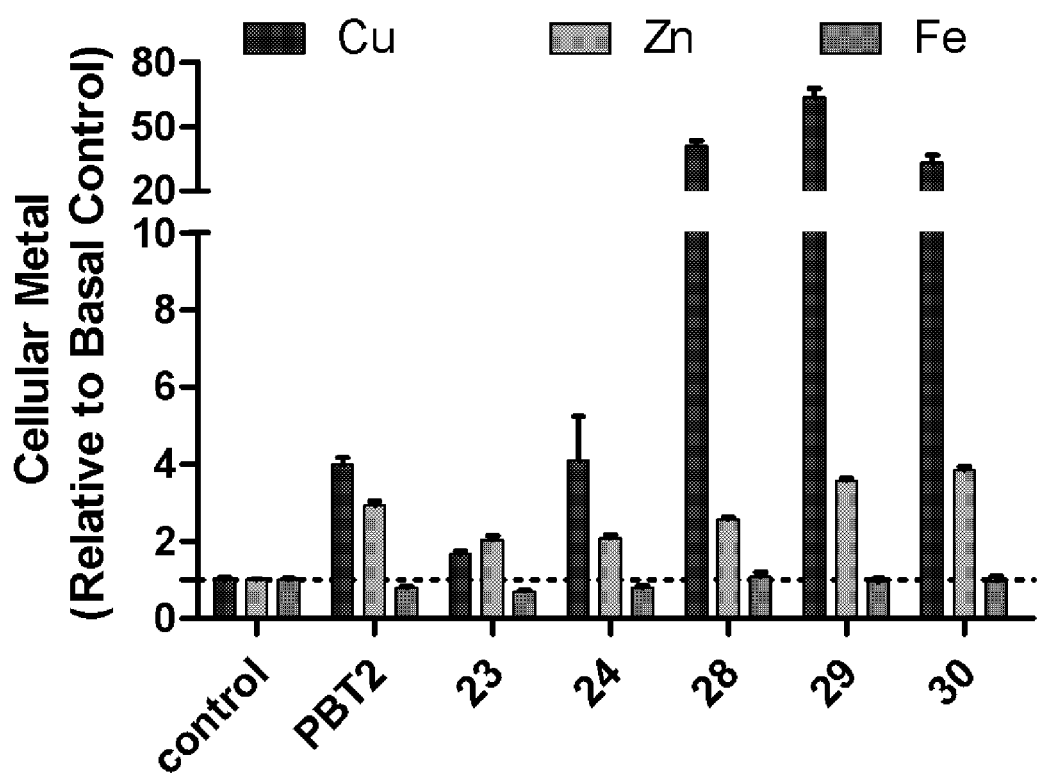
FIG. 3 shows an ionophore activity of 8HQ derivatives: Compounds 23, 24, 28-30.

FIG. 3 describes ionophore activity of PBT2 derivatives (PBT2 and compounds 23, 24, 28, 29, 30). SH-SY5Y cells treated were treated with each compound (20 μM) for 6 hours and cellular metal levels were measured with ICP-MS. Dashed line indicates control level.

Example B: Aβ Reversal Assays

Aβ Aggregation Assay:

4,4(')-dianilino-1,1(')-binaphthyl-5,5(')-disulfonate (bis-ANS, Sigma) was used to assess whether compounds could reverse the aggregation of soluble Aβ oligomers. (See, e.g., LeVine, H., 3rd, (2002) 4,4(')-Dianilino-1,1(')-binaphthyl-5,5(')-disulfonate: report on non-beta-sheet conformers of Alzheimer's peptide beta(1-40), Arch Biochem Biophys 404, 106; Chen, W. T. et al., (2011) Distinct effects of $Zn^{2+}$, $Cu^{2+}$, $Fe^{3+}$, and $Al^{3+}$ on amyloid-beta stability, oligomerization, and aggregation: amyloid-beta destabilization promotes annular protofibril formation, J Biol Chem 286, 9646) Human Aβ1-42 (China Peptide) was dissolved in DMSO (Sigma) to a stock concentration of 1.5 mM. Aβ (15 μM) oligomers were induced with $ZnSO_4$ (15 μM) at 26° C. for 30 min in a buffer (pH 7.4) containing Tris (50 mM), NaCl (150 mM) and bis-ANS (10 μM). Compounds (0.1 to 120 μM) dissolved in DMSO (Sigma) were added for 30 min. CQ and PBT2 were used as positive controls. Endpoint fluorescence (excitation=390 nm, emission=490 nm) was measured with a Flex Station (Molecular Devices) fluorescent plate reader. At each concentration, Aβ fluorescence was normalized to background fluorescence and then expressed as a percentage of vehicle treated control samples. The effective concentration that reversed Aβ aggregation by 50% relative to control (EC$_{50}$) was determined with non-linear regression analysis (Prism 6, Graphpad). Data represents the mean of at least 9 replicates from 3 experiments.

TABLE 1

Reversal of aggregation of soluble Aβ oligomers by fluorinated 8-hydroxyquinoline derivatives[a]

| Compound No. | EC$_{50}$ (μM) |
|---|---|
| 5 | >120 |
| 6 | 43.5 |
| 7 | 21.5 |
| 8 | 37.5 |
| 9 | 14.0 |
| 10 | 15.4 |
| Clioquinol (CQ) | 1.8 |
| 12 | 4.9 |
| 13 | 3.5 |
| 14 | 2.3 |
| 15 | 5.2 |
| 16 | 3.7 |
| 17 | 2.5 |
| PBT2 | 2.0 |
| 23 | 2.4 |
| 24 | 2.0 |
| 28 | 2.3 |
| 29 | 4.5 |
| 30 | 2.8 |

[a]Aggregation of Aβ oligomers was assessed fluorometrically with bis-ANS.
EC$_{50}$ was determined with non-linear regression analysis (Prism 6, Graphpad). CQ and PBT2 were used as positive controls. Data represent mean of at least three independent experiments.

The compounds of the present application showed superior binding affinity, metal selectivity and Cu and Zn ionophore activity over the agents CQ and PBT2.

Evaluation of fluorine substituents around the hydroxyquinoline revealed that compound 5 and compound 6 were inferior to 8HQ in terms of Cu uptake while compounds 7-9 showed equal or superior Cu uptake (FIG. 1). Neuronal Zn uptake was largely unaffected. Replacement of labile iodine on CQ with other halides, such as fluoride, chloride or bromide, was carried out at various positions to improve the stability of the molecule due to higher C—X (X=F, Cl or Br) bond energies (Chart 3). Among six analogs screened, compounds 15-17 showed improved ionophore ability of both Cu and Zn (FIG. 2).

Compounds 28-30 showed exceptional Cu uptake (10-fold increase for compound 28, 16-fold increase for compound 29 and 8-fold increase for compound 30) than that of PBT2. For Zn neuronal uptake, compounds 28-30 showed comparable results as PBT2 (FIG. 3).

Compounds 6-10 showed improved anti Aβ aggregation activities compared to compound 5. Compounds 12-14 and compounds 15-17 have EC$_{50}$ values in the range of 2.3-5.2 μM. Compounds 23, 24 and 28-30 (EC$_{50}$=2.0-4.5 μM) are also excellent candidates.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula I:

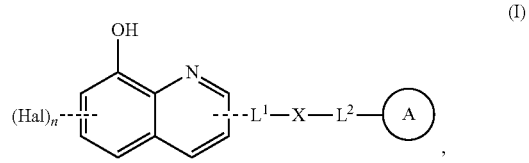

(I)

or a pharmaceutically acceptable salt thereof, wherein:

Hal is selected from the group consisting of Cl, F, Br, and I;

n is 1, 2, or 3;

X is selected from the group consisting of O, S, S(O), S(O)$_2$, C(O), and NR$^N$;

L$^1$ is selected from the group consisting of —C$_{1-6}$ alkylene-, —Y—C$_{1-6}$ alkylene-, —C$_{1-4}$ alkylene-Y—C$_{1-4}$ alkylene-, and —(O—C$_{1-4}$ alkylene)$_m$-, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

L$^2$ is selected from the group consisting of —C$_{1-6}$ alkylene-, —C$_{1-6}$ alkylene-Y—, —C$_{1-4}$ alkylene-Y—C$_{1-4}$ alkylene-, and —(C$_{1-4}$ alkylene-O—)$_m$—, wherein m is an integer from 1 to 5, and wherein said alkylene groups are each optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

each Y is independently selected from the group consisting of O, S, S(O), S(O)$_2$, C(O), C(O)NR$^f$, NR$^f$C(O), S(O)$_2$NR$^f$, NR$^f$S(O)$_2$, and NR$^f$;

each R$^f$ is independently selected from the group consisting of H and C$_{1-3}$ alkyl;

R$^N$ is selected from the group consisting of H, C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl, wherein said C$_{1-6}$ alkyl, C$_{2-6}$ alkenyl, C$_{2-6}$ alkynyl, C$_{1-4}$ haloalkyl, C$_{3-10}$ cycloalkyl, and 4-10 membered heterocycloalkyl are each optionally substituted by 1, 2, 3, or 4 independently selected R$^g$ groups;

group A is selected from the group consisting of a 5-10 membered heteroaryl and 4-10 membered heterocycloalkyl, each of which is optionally substituted by 1, 2, 3, or 4 independently selected R$^A$ groups;

alternatively, group A is H;

with the proviso that when X is NR$^N$, L$^1$ is —C$_{1-6}$ alkylene-, L$^2$ is —C$_{1-6}$ alkylene-, and R$^N$ is C$_{1-6}$ alkyl, group A is not H;

each R$^A$ is independently selected from the group consisting of OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C₁₋₆ alkylaminosulfonyl, di(C₁₋₆ alkyl)aminosulfonyl, aminosulfonylamino, C₁₋₆ alkylaminosulfonylamino, di(C₁₋₆ alkyl)aminosulfonylamino, aminocarbonylamino, C₁₋₆ alkylaminocarbonylamino, and di(C₁₋₆ alkyl)aminocarbonylamino; and each R^g is independently selected from the group consisting of OH, NO₂, CN, halo, C₁₋₆ alkyl, C₂₋₆ alkenyl, C₂₋₆ alkynyl, C₁₋₄ haloalkyl, C₁₋₆ alkoxy, C₁₋₆ haloalkoxy, cyano-C₁₋₃ alkyl, HO—C₁₋₃ alkyl, amino, C₁₋₆ alkylamino, di(C₁₋₆ alkyl)amino, thio, C₁₋₆ alkylthio, C₁₋₆ alkylsulfinyl, C₁₋₆ alkylsulfonyl, carbamyl, C₁₋₆ alkylcarbamyl, di(C₁₋₆ alkyl)carbamyl, carboxy, C₁₋₆ alkylcarbonyl, C₁₋₆ alkoxycarbonyl, C₁₋₆ alkylcarbonylamino, C₁₋₆ alkylsulfonylamino, aminosulfonyl, C₁₋₆ alkylaminosulfonyl, di(C₁₋₆ alkyl)aminosulfonyl, aminosulfonylamino, C₁₋₆ alkylaminosulfonylamino, di(C₁₋₆ alkyl)aminosulfonylamino, aminocarbonylamino, C₁₋₆ alkylaminocarbonylamino, and di(C₁₋₆ alkyl)aminocarbonylamino wherein the compound comprises at least one radioisotope.

2. The compound of claim 1, wherein the compound of Formula (I) is a compound of Formula (Ia):

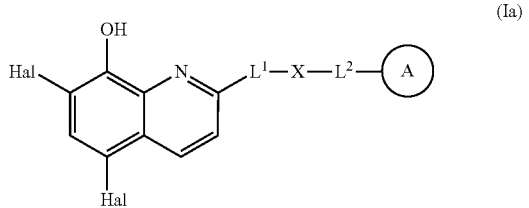

or a pharmaceutically acceptable salt thereof.

3. The compound of claim 1, wherein:

Hal is selected from the group consisting of: Cl, F, and I;

X is selected from the group consisting of O and NR^N;

L¹ is —C₁₋₆ alkylene-, wherein said alkylene group is optionally substituted with 1, 2, or 3 substituents independently selected from halo, CN, OH, C₁₋₃ alkoxy, and amino;

L² is —C₁₋₆ alkylene-, wherein said alkylene group is optionally substituted with 1, 2, or 3 substituents independently selected from halo, CN, OH, C₁₋₃ alkoxy, and amino;

R^N is selected from the group consisting of H and C₁₋₆ alkyl;

group A is 5 or 6 membered heteroaryl, which is optionally substituted by 1, 2, or 3 independently selected R^A groups;

alternatively, group A is H;

with the proviso that when X is NR^N, L¹ is —C₁₋₆ alkylene-, L² is —C₁₋₆ alkylene-, and R^N is C₁₋₆ alkyl, group A is not H; and each R^A is independently selected from the group consisting of OH, NO₂, CN, halo, C₁₋₆ alkyl, C₂₋₆ alkenyl, C₂₋₆ alkynyl, C₁₋₆ haloalkyl, C₁₋₆ alkoxy, C₁₋₆ haloalkoxy, cyano-C₁₋₃ alkyl, HO—C₁₋₃ alkyl, amino, C₁₋₆ alkylamino, and di(C₁₋₆ alkyl)amino.

4. The compound of claim 1, wherein the compound of Formula (Ia) is a compound of Formula (Ib):

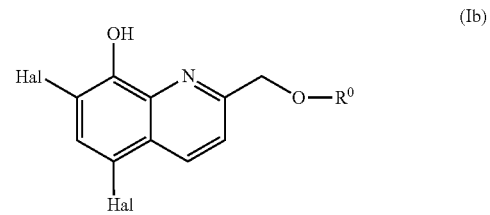

or a pharmaceutically acceptable salt thereof, wherein:

Hal is selected from the group consisting of Cl, F, and I; and

R⁰ is —C₁₋₆ alkyl, which is optionally substituted with 1, 2, or 3 substituents independently selected from halo, CN, OH, C₁₋₃ alkoxy, amino, C₁₋₃ alkylamino, and di(C₁₋₃ alkyl)amino.

5. The compound of claim 1, wherein the compound of Formula Ia is a compound of Formula Ic:

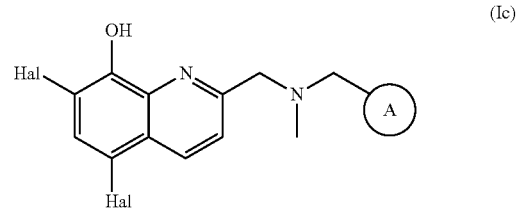

or a pharmaceutically acceptable salt thereof, wherein:

Hal is selected from the group consisting of Cl, F, and I; and group A is selected from the group consisting of a 5-6 membered heteroaryl and 4-10 membered heterocycloalkyl, each of which is optionally substituted by 1, 2, 3, or 4 independently selected R^A groups.

6. The compound of claim 1, wherein group A is a triazolyl of Formula A-1c:

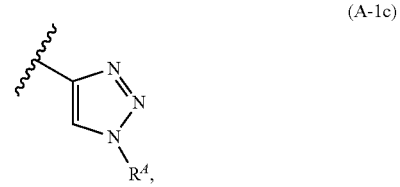

wherein R^A is selected from the group consisting of C₁₋₆ alkyl, C₁₋₆ haloalkyl, cyano-C₁₋₃ alkyl, and HO—C₁₋₃ alkyl.

7. The compound of claim 1, wherein the compound of Formula (I) is selected from the group consisting of:

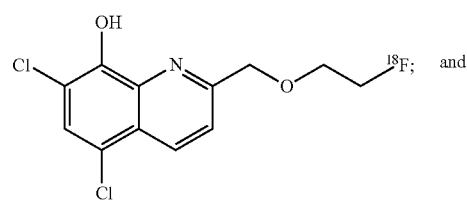

and

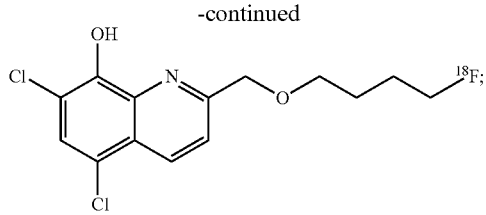

or a pharmaceutically acceptable salt thereof.

8. A pharmaceutical composition comprising a compound of claim 1, or a pharmaceutically acceptable salt thereof, and at least one pharmaceutically acceptable carrier.

9. A method of treating a disease of condition selected from a neurological disorder and a cancer in a subject in need thereof, the method comprising administering to the subject a therapeutically effective amount of a compound of claim 1, or a pharmaceutically acceptable salt thereof.

10. The compound of claim 1, wherein the compound is selected from the group consisting of:

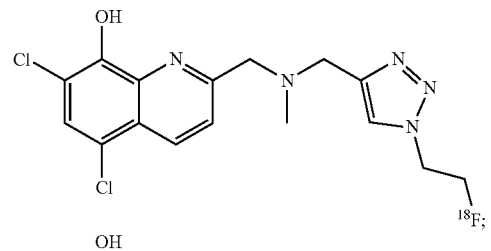

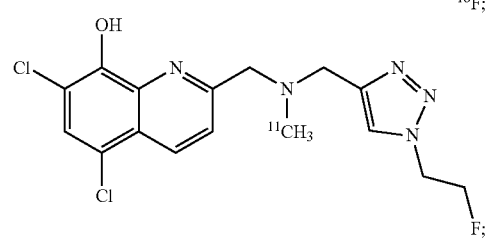

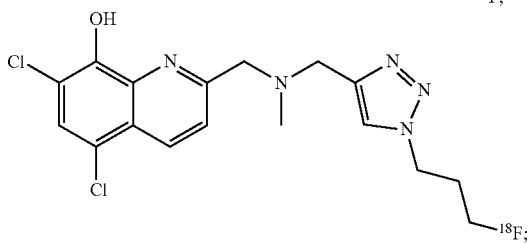

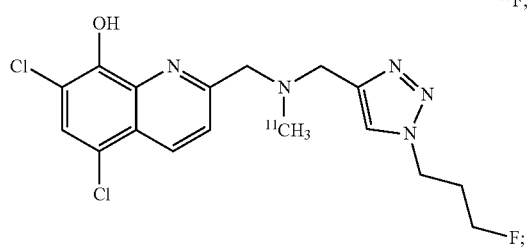

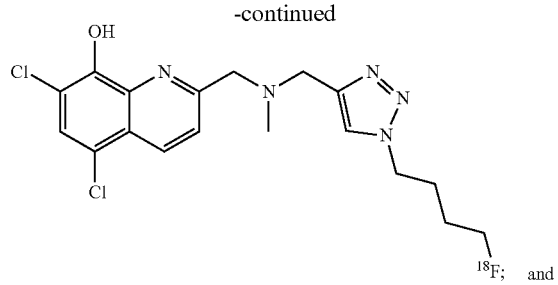

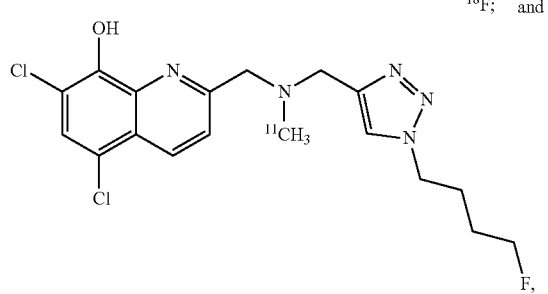

or a pharmaceutically acceptable salt thereof.

11. A method of imaging the brain of a subject, the method comprising:
   i) administering to the subject an effective amount of a compound claim 1, or a pharmaceutically acceptable salt thereof;
   ii) waiting a time sufficient to allow the compound to accumulate in the brain to be imaged; and
   iii) imaging the brain with an imaging technique.

12. A method of diagnosing a disorder selected from a neurological disorder and a cancer in a subject, the method comprising:
   i) administering to the subject a compound of claim 1, or a pharmaceutically acceptable salt thereof;
   ii) waiting a time sufficient to allow the compound to accumulate at a tissue or cell site associated with the disorder; and
   iii) imaging the cell or tissue with an imaging technique.

13. A method of monitoring treatment of a disorder selected from a neurological disorder and a cancer in a subject, the method comprising:
   i) imaging a cell or tissue with an imaging technique;
   ii) administering to the subject a compound of claim 1, or a pharmaceutically acceptable salt thereof, in an effective amount of to treat the disorder;
   iii) waiting a time sufficient to allow the compound to accumulate at a tissue or cell site associated with the disorder;
   iv) imaging the cell or tissue with an imaging technique; and
   v) comparing the image of step i) and the image of step iv).

* * * * *

UNITED STATES PATENT AND TRADEMARK OFFICE
CERTIFICATE OF CORRECTION

PATENT NO. : 10,781,178 B2
APPLICATION NO. : 15/751778
DATED : September 22, 2020
INVENTOR(S) : Neil Vasdev and Huan Steven Liang Page 1 of 1

It is certified that error appears in the above-identified patent and that said Letters Patent is hereby corrected as shown below:

In the Claims

Column 100, Line 28, Claim 11, after "compound" insert -- of --

Signed and Sealed this
Second Day of February, 2021

Drew Hirshfeld
*Performing the Functions and Duties of the
Under Secretary of Commerce for Intellectual Property and
Director of the United States Patent and Trademark Office*